(12) United States Patent
O'Neill et al.

(10) Patent No.: US 12,311,114 B2
(45) Date of Patent: May 27, 2025

(54) METHOD AND APPARATUS FOR TREATING A NEUROLOGICAL DISORDER

(71) Applicant: NEUROMOD DEVICES LIMITED, Dublin (IE)

(72) Inventors: Ross O'Neill, Dublin (IE); Stephen Hughes, Dublin (IE); Shona D'Arcy, Dublin (IE); Caroline Hamilton, Dublin (IE); Brendan Conlon, Wicklow (IE)

(73) Assignee: Neuromod Devices Limited, Dublin (IE)

( * ) Notice: Subject to any disclaimer, the term of this patent is extended or adjusted under 35 U.S.C. 154(b) by 948 days.

(21) Appl. No.: 17/131,436

(22) Filed: Dec. 22, 2020

(65) Prior Publication Data
US 2021/0138186 A1    May 13, 2021

Related U.S. Application Data

(63) Continuation of application No. 14/915,559, filed as application No. PCT/EP2014/068256 on Aug. 28, (Continued)

(30) Foreign Application Priority Data

Aug. 30, 2013  (EP) .................................... 13182487
Nov. 17, 2015  (EP) .................................... 15195055
Nov. 17, 2015  (IE) .................................... 2015/0407

(51) Int. Cl.
A61M 21/02   (2006.01)
A61M 21/00   (2006.01)
(Continued)

(52) U.S. Cl.
CPC ..... *A61M 21/02* (2013.01); *A61M 2021/0022* (2013.01); *A61M 2021/0027* (2013.01); (Continued)

(58) Field of Classification Search
CPC .......... A61M 21/02; A61M 2021/0022; A61M 2021/0027; A61M 2021/0072;
(Continued)

(56) References Cited

U.S. PATENT DOCUMENTS 5,788,656 A    8/1998  Mino
6,047,074 A    4/2000  Zoels et al.
(Continued)

FOREIGN PATENT DOCUMENTS

DE  102011100065 A1   10/2012
EP      2658492 A2    11/2013
(Continued)

OTHER PUBLICATIONS

Audionotch Team; The audionotch tinnitus treatmentblog: mutebutton tinnitus; 9 pages retrieved from the internet (https://www.audionotch.com/blog/2015/06/16/mutebutton-tinnitus/) on Mar. 2021.
(Continued)

*Primary Examiner* — Thaddeus B Cox
*Assistant Examiner* — Joshua Daryl D Lannu
(74) *Attorney, Agent, or Firm* — Shay Glenn LLP

(57) ABSTRACT

A method of reducing anxiety in a subject. In some embodiments, the method includes the steps of: providing an audio input to the subject, the audio input including a sequence of tones in a frequency range comprising about 100 Hz to about 8000 Hz and having intensities adapted to audiometric parameters of the subject; producing a plurality of actuation signals correlated with the audio input; delivering an actuation signal of the plurality of actuation signals to each of a plurality of electrodes in contact with a tissue surface of the subject's body to provide tactile stimuli to the tissue surface; and reducing anxiety in the subject.

28 Claims, 23 Drawing Sheets

Related U.S. Application Data 2014, now Pat. No. 10,987,249, which is a continuation of application No. 15/777,166, filed as application No. PCT/EP2016/078077 on Nov. 17, 2016, and a continuation-in-part of application No. 15/777,184, filed as application No. PCT/EP2016/077781 on Nov. 17, 2016, now Pat. No. 11,245,996.

(51) Int. Cl.
    *A61N 1/04*     (2006.01)
    *A61N 1/05*     (2006.01)
    *A61N 1/36*     (2006.01)

(52) U.S. Cl.
    CPC ............... *A61M 2021/0072* (2013.01); *A61M 2210/0643* (2013.01); *A61N 1/0548* (2013.01)

(58) Field of Classification Search
    CPC .. A61M 2210/0643; A61M 2210/0662; A61N 1/0548; A61N 1/0456; A61N 1/0476; A61N 1/0484; A61N 1/3603; A61N 1/36025
    See application file for complete search history.

(56) References Cited

U.S. PATENT DOCUMENTS

| | | | |
|---|---|---|---|
| 6,048,305 | A | 4/2000 | Bauman et al. |
| 6,198,971 | B1 | 3/2001 | Leysieffer |
| 6,205,473 | B1 | 3/2001 | Thomasson et al. |
| 6,259,951 | B1 | 7/2001 | Kuzma et al. |
| 6,409,655 | B1 | 6/2002 | Wilson et al. |
| 6,430,443 | B1 | 8/2002 | Karell |
| 6,430,450 | B1 | 8/2002 | Bach y Rita et al. |
| 6,682,472 | B1 | 1/2004 | Davis |
| 6,990,377 | B2 | 1/2006 | Gliner et al. |
| 7,439,630 | B2 | 10/2008 | Peacock |
| 7,613,519 | B2 | 11/2009 | De Ridder |
| 7,856,264 | B2 | 12/2010 | Firlik et al. |
| 8,176,317 | B2 | 5/2012 | Thomasson et al. |
| 8,273,034 | B2 | 9/2012 | Fogel et al. |
| 8,463,378 | B2 | 6/2013 | Tass |
| 8,666,501 | B2 | 3/2014 | Kilgard et al. |
| 8,874,220 | B2 | 10/2014 | Draghici et al. |
| 8,885,861 | B2 | 11/2014 | Beck et al. |
| 9,089,703 | B2 | 7/2015 | Rodriguez et al. |
| 9,089,707 | B2 | 7/2015 | Kilgard et al. |
| 9,124,979 | B2 | 9/2015 | O'Grady et al. |
| 9,242,067 | B2 | 1/2016 | Shore et al. |
| 9,522,085 | B2 | 12/2016 | Kilgard et al. |
| 10,265,527 | B2 | 4/2019 | Lim et al. |
| 10,701,498 | B2 | 6/2020 | Lim et al. |
| 10,893,371 | B2 | 1/2021 | Hughes et al. |
| 2001/0031996 | A1 | 10/2001 | Leysieffer |
| 2002/0035309 | A1 | 3/2002 | Leysieffer |
| 2002/0090100 | A1 | 7/2002 | Thiede et al. |
| 2005/0043646 | A1 | 2/2005 | Viirre et al. |
| 2005/0201574 | A1 | 9/2005 | Lenhardt |
| 2005/0240253 | A1 | 10/2005 | Tyler et al. |
| 2006/0031423 | A1 | 2/2006 | Mosbarger et al. |
| 2007/0027504 | A1 | 2/2007 | Barrett et al. |
| 2007/0133832 | A1 | 6/2007 | DiGiovanni et al. |
| 2007/0156063 | A1 | 7/2007 | Zoth et al. |
| 2007/0270920 | A1 | 11/2007 | Turner et al. |
| 2008/0021517 | A1 | 1/2008 | Dietrich |
| 2008/0137873 | A1 | 6/2008 | Goldstein |
| 2009/0270673 | A1 | 10/2009 | Abolfathi et al. |
| 2009/0306741 | A1 | 12/2009 | Hogle et al. |
| 2010/0042739 | A1 | 2/2010 | Clarke et al. |
| 2010/0121411 | A1 | 5/2010 | Hochmair et al. |
| 2011/0040205 | A1 | 2/2011 | Parra et al. |
| 2011/0054241 | A1 | 3/2011 | Jensen |
| 2011/0172725 | A1 | 7/2011 | Wells et al. |
| 2012/0203301 | A1 | 8/2012 | Cameron et al. |
| 2013/0184552 | A1 | 7/2013 | Westermann et al. |
| 2014/0135886 | A1 | 5/2014 | Cook et al. |
| 2014/0142669 | A1 | 5/2014 | Cook et al. |
| 2015/0245151 | A1 | 8/2015 | Nötzel et al. |
| 2015/0290454 | A1* | 10/2015 | Tyler .................. G06F 3/012 607/134 |
| 2016/0038712 | A1 | 2/2016 | Finsterle |
| 2017/0042739 | A1 | 2/2017 | O'Neill et al. |
| 2017/0224990 | A1* | 8/2017 | Goldwasser ......... A61N 1/0476 |

FOREIGN PATENT DOCUMENTS

| | | | |
|---|---|---|---|
| EP | 2968010 | A1 | 1/2016 |
| EP | 3170479 | A1 | 5/2017 |
| EP | 3376954 | A1 | 9/2018 |
| EP | 3377012 | A1 | 9/2018 |
| WO | WO2002/080817 | A1 | 10/2002 |
| WO | WO2006/047264 | A1 | 5/2006 |
| WO | WO2006/130909 | A1 | 12/2006 |
| WO | WO2009/061520 | A1 | 5/2009 |
| WO | WO2010/028152 | A2 | 3/2010 |
| WO | WO2014/145914 | A1 | 9/2014 |
| WO | WO2017/085227 | A1 | 5/2017 |

OTHER PUBLICATIONS

Conlon et al.; Bimodal neuromodulation combining sound and tongue stimulation reduces tinnitus symptoms in a large randomized clinical study; Science Translational Medicine; 12(564); 16 pages; eabb2830; Oct. 2020.

D'Arcy et al.; Bi-modal stimulation in the treatment of tinnitus: a study protocol for an exploratory trial to optimise stimulation parameters and patient subtyping; BMJ Open; 7(10); 10 pages; DOI:10.1136/bmjopen-2017-018465; Oct. 2017.

De Ridder et al.; Safety and efficacy of vagus nerve stimulation paired with tones for the treatment of tinnitus: a case series; Neuromodulation: Technology at the Neural Interface; 17(2); pp. 170-179; Feb. 2014.

Dehmel et al.; Noise overexposure alters long-term somatosensory-auditory processing in the dorsal cochlear nucleus-possible basis for tinnitus-related hyperactivity ?; Journal of Neuriscience; 32(5); pp. 1660-1671; Feb. 2012.

Geffen et al.; Sex differences in the perception of tactile simultaneity; Cortex; 36(3); pp. 323-335; Jan. 2000.

Gilligan; Mutebutton; (Screenshot); 2 pages; retrived from the internet at Vimeo (https://vimeo.com/16020279) available as of Mar. 25, 2021.

Hamilton et al.; An investigation of feasibility and safety of bi-modal stimulation for the treatment of tinnitus: an open-label pilot study; Neuromodulation: Technology at the Neural Interface; 19(8); pp. 832-837; Dec. 2016.

Hesser et al.; The effect of waiting: a meta-analysis of wait-list control groups in trials for tinnitus distress; journal of Psychosomatic Research; 70(4); pp. 378-384; Apr. 2011.

Jastraboff et al.; Neurophysiological model of tinnitus: dependence of the minimal masking level on treatment outcome; Hearing research; 80(2); pp. 216-232; Nov. 1994.

Kaczmarek et al.; Maximal dynamic range electrotactile stimulation; Miomedical Engineering, IEEE Transactions on Biomedical Engineering; 39(7); pp. 701-715; Jul. 1992.

Koehler et al.; Stimulus timing-dependent plasticity in dorsal cochlear nucleus is altered in tinnitus Journal of Neuroscience; 33(50); pp. 19647-19656; Dec. 2013.

Lozano et al.; Electrotacile stimulation on the tongue: intensity perception, discrimination, and cross-modality estimation; Somatosensory and Motor Research; 26(2-3); pp. 50-63; 22 pages (Author Manuscript); Jan. 2009.

Markovitz et al.; Investigating a new neuromodulation treatment for brain disorders using synchronized activation of multimodal pathways; Scientific Reports; 5(1); pp. 1-12; DOI:10.1038/srep09462; Mar. 2015.

Meikle et al; The tinnitus functional index: development of a new clinical measure for chronic intrusive tinnitus; Ear and Hearing; 33(2); pp. 153-176; Mar. 2012.

(56) References Cited

OTHER PUBLICATIONS

Salvi et al.; Pharmacological treatments for tinnitus: new and old; Drugs of the Future; 34(5); pp. 381-400; 35 pages; (Author Manuscript); (year of pub. sufficiently earlier than effective US filing date and any foreign priority date) 2009.
Spiegel et al.; Multisensory attention training for treatment of tinnitus; Scientific Reports; 5(10802); pp. 1-11; May 2015.
Stevens; On the psychophysical law; Psychological review; 64(3); pp. 153-181; May 1957.
U.S Department of Health, Education, and Walfare; Hearing levels of adults by age and sex: United States, Series 11, No. 11; 1960-1962; 40 pages; retrieved from the internet (https://www.cdc.gov/nchs/data/series/sr_11/sr11_011acc.pdf) on Mar. 25, 2021.
Wikipedia; Sound from ultrasound; 11 pages; retrieved from the internet (https://en.wikipedia.org/wiki/Sound_from_ultrasound) on Mar. 25, 2021.
Zeman et al.; Tinnitus handicap inventory for evaluating treatment effects: which changes are clinically relevant ?; Otolaryngology-Head and Neck Surgery; 145(2); pp. 282-287; Aug. 2011.
Hughes et al.; U.S. Appl. No. 15/777,184 entitled An apparatus and method for treating a neurological disorders of the auditory system, filed May 17, 2018.

\* cited by examiner

AVERAGE SYMPTOM SCORES OVER 10 WEEKS OF TREATMENT FOR MML AND TLM (UNITS IN dB HL) AND THI

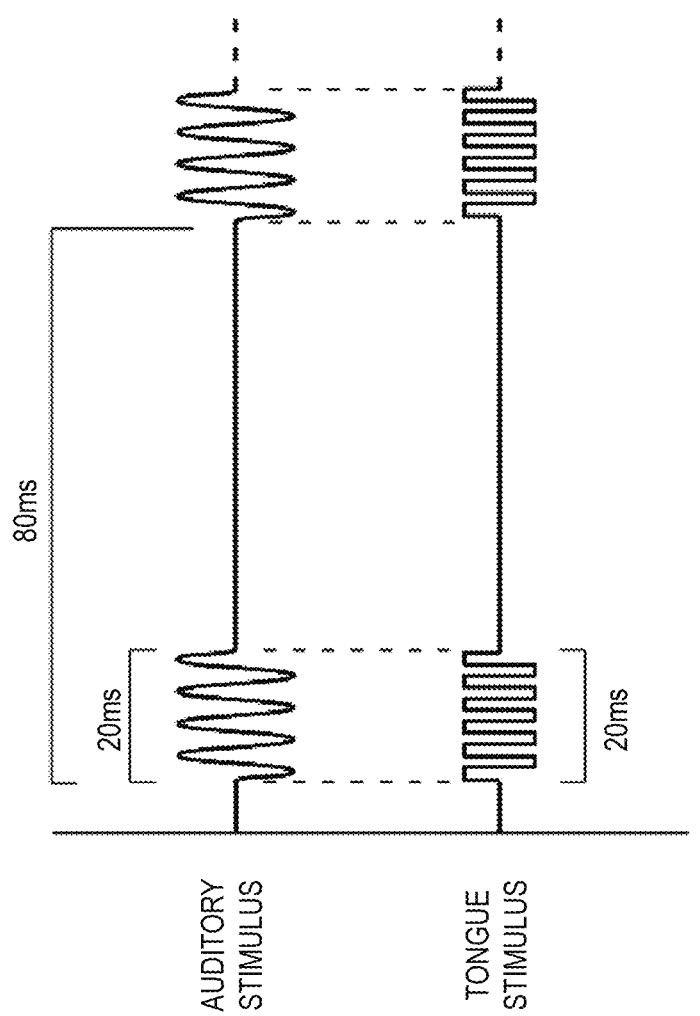

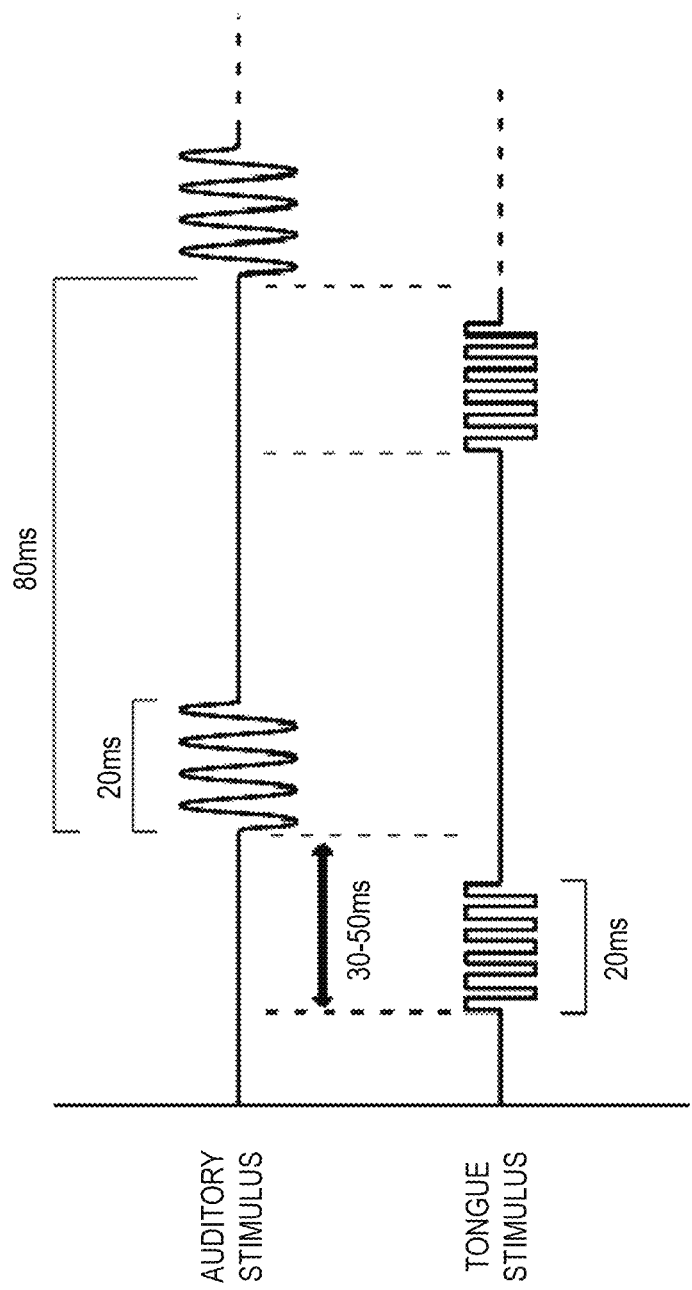

| | Change in STAI by treatment ARMS | | | | | | | |
|---|---|---|---|---|---|---|---|---|
| | Mean | SD | n | 1 vs 2 | 1 vs 3 | 2 vs 3 | within | Baseline score | Baseline SD | Baseline n |
| Arm 1 | -7.59091 | 12.0846 | 88 | 0.068 | 0.3313 | 0.4341 | <0.0001 | 75.84545 | 17.14653 | 110 |
| Arm 2 | -4.18085 | 12.97057 | 94 | | | | 0.0024 | 72.96262 | 16.73203 | 107 |
| Arm 3 | -5.71591 | 13.41208 | 88 | | | | 0.0001 | 74.20183 | 16.89608 | 109 |

METHOD AND APPARATUS FOR TREATING A NEUROLOGICAL DISORDER

CROSS REFERENCE TO RELATED APPLICATIONS

This application is a continuation-in-part of U.S. application Ser. No. 14/915,559, filed Feb. 29, 2016, which is a national phase of PCT/EP2014/068256, filed Aug. 28, 2014, claiming priority to European Patent Application No. 13182487.2, filed Aug. 30, 2013, and is a continuation-in-part of U.S. application Ser. No. 15/777,166, filed May 17, 2018, which is a national phase of PCT/EP2016/077781, filed Nov. 15, 2016, claiming priority to European Patent Application No. 15195055.7, filed Nov. 17, 2015, and Irish Application No. 2015/0407, filed Nov. 17, 2015, and is a continuation-in-part of U.S. application Ser. No. 15/777, 184, filed May 17, 2018, which is a national phase of PCT/EP2016/078077, filed Nov. 17, 2016, claiming priority to European Application No. 15195055.7, filed Nov. 17, 2015, and Irish Application No. 2015/0407, filed Nov. 17, 2015, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates to the delivery of a bimodal stimulus to a subject suffering from a neurological disorder, such as, e.g., tinnitus, anxiety, and depression.

BACKGROUND

Subjective tinnitus is an intrusive and debilitating condition, most commonly described as 'ringing in the ears' that significantly affects up to 5% of the global population. Many tinnitus sufferers report feeling distressed by their symptoms and report a resulting diminishment in their quality of life and that of their families Patients find further frustration in a perceived lack of treatment options. Currently available treatments (discussed below) are limited, with the vast majority of patients being told there are no treatment options and that they should 'learn to live with their tinnitus'. This has resulted in widespread disillusionment with the clinical professions and pent up market demand for a viable treatment alternative. Leading tinnitus experts have acknowledged that current treatments are ineffective and that there is a remaining unmet clinical need. They have also stressed that a treatment that produced even a small but significant effect would have an enormous therapeutic impact on this huge and growing underserviced market.

Both pharmacologic and non-pharmacologic treatments are currently used to manage the symptoms of tinnitus. These range from off-label drugs, such as Serc, through different forms of psychological counselling, including Tinnitus Retraining Therapy (TRT) and Cognitive Behavioral Therapy (CBT), to medical devices, such as Hearing Aids, Noise-maskers and Electrical Stimulators. Current therapies tend to provide only temporary symptomatic relief and are generally chosen based on the severity of the condition. The benefit and limitations of these treatments have been the subject of a number of review articles. Pharmacological treatments include; antidepressants, vasodilators, intravenous lidocaine, barbiturates, antihistamines, beta histamine, and benzodiazepines. However, it is preferable pharmacological treatments are used to treat coexisting symptoms such as depression and anxiety. Generally, the ineffectiveness of pharmacological treatments has been recognized and documented by leading tinnitus experts.

Tinnitus has a diverse range of etiologies but it is commonly accompanied by a high-frequency hearing loss, or sensorineural hearing loss (SNHL). There is a growing body of scientific evidence that hearing loss causes increased neural spontaneous and stimulus-driven excitability in the auditory brainstem and cortex, and that this increased activity is linked with the perception of the illusory sounds of tinnitus. Two recognized modalities may be stimulated in order to suppress this neuropathological hyperactivity:

Auditory Stimulation
Somatosensory Stimulation

EP2 842 530 A1 and EP2 658 491 A1 both combine auditory and somatosensory stimulation in the treatment of tinnitus. In applying multi-modal neuromodulation, it is theorized that stimulating the neural pathways of patients through both the somatic and auditory senses with the same information, may give increased benefit to the patient over time, as it may facilitate the brain to learn which part of the perceived sound is real, and which part is illusory (the pathological tinnitus). US2014/275737A1 discloses timed stimulation of both somatosensory system and auditory system to alter an individual's brain activity through spike timing dependent plasticity thereby reducing or removing tinnitus. Stimuli are generated and applied in an alternative mechanism to that disclosed in the present application. However, there is a need to provide an improved device which offers significant advantages in terms of performance and usability when compared with the prior art and the commercially available tinnitus treatments described above. The present invention solves this problem through an alternative transformation between the auditory and somatosensory stimulation.

U.S. Pat. No. 10,265,527 describes the use of multimodal stimulation from an auditory and a non-auditory neuronal pathway to treat tinnitus. While this patent mentions other neurological conditions, such as obsessive-compulsive disorder, depression, or stress, it does not describe any stimulation parameters that would reduce anxiety, or improve sleep, beyond any anxiety reduction or sleep improvement that is caused by a reduction in tinnitus.

There is a recognized relationship between tinnitus and anxiety. While a reduction in tinnitus symptoms can lead to a reduction in anxiety, the prior art has not described a multimodal stimulation therapy that reduces anxiety beyond the changes in anxiety that would be expected from a reduction in tinnitus.

SUMMARY OF THE DISCLOSURE

One aspect of the invention provides a method of reducing anxiety in a subject. In some embodiments, the method includes the steps of: providing an audio input to the subject, the audio input having a sequence of tones in a frequency range comprising about 100 Hz to about 8000 Hz and having intensities adapted to audiometric parameters of the subject; producing a plurality of actuation signals correlated with the audio input; delivering an actuation signal of the plurality of actuation signals to each of a plurality of electrodes in contact with a tissue surface of the subject's body to provide tactile stimuli to the tissue surface; and reducing anxiety in the subject. The tissue surface may be, e.g., a tissue surface of the subject's head. The tissue surface may be the subject's tongue.

In some embodiments, the sequence of tones includes at least one tone that has a frequency of about 100 Hz, at least one other tone in the sequence of tones has a frequency of about 500 Hz, and other tones in the plurality of tones have frequencies in a range of about 100 Hz to about 500 Hz.

In some embodiments, the tones are separated by an inter-tone time of about 80 milliseconds to about 2 seconds. In some such embodiments, each tone in the sequence of tones is presented about every 80 milliseconds. In other such embodiments, each tone in the sequence of tones is presented about every 2 seconds.

In some embodiments, each tone in the sequence of tones has duration of about 15 milliseconds to about 500 milliseconds. In some such embodiments, each tone in the sequence of tones has a duration of about 15 milliseconds. In other such embodiments, each tone in the sequence of tones has a duration of about 500 milliseconds.

In some embodiments, each tone in the sequence of tones fades out as the tone ends.

In some embodiments, the audio input also includes noise. In some such embodiments, the noise includes broadband noise having a range of about 100 Hz to about 8000 Hz. In other such embodiments, the noise includes low frequency noise having a range of about 100 Hz to about 500 Hz.

In some embodiments, each actuation signal includes a pulse train. In some such embodiments, the pulse train has a duration of about 12-15 milliseconds. In other such embodiments, each pulse in the pulse train has a duration of about 5-210 microseconds.

Some embodiments include the optional further step of adjusting the actuation signals to a level of sensory perception of the subject.

In some embodiments, the electrodes are disposed in a fixed array. In such embodiments, the step of delivering an actuation signal may include the step of delivering an actuation signal to an electrode at a position in the array corresponding to a frequency of the correlated audio input.

In some embodiments, each electrode in the plurality of electrodes corresponds to a frequency bin within the frequency range of the audio input, and the step of delivering an actuation signal includes the step of delivering each actuation signal to an electrode having a frequency bin corresponding to a frequency of the correlated audio input simultaneous with providing the correlated audio input to the subject at such frequency. In some such embodiments, the step of delivering an actuation signal may also include the step of delivering the actuation signal simultaneously to two electrodes of the plurality of electrodes, each having a frequency bin corresponding to the frequency of the correlated audio input and simultaneous with providing the correlated audio input to the subject at the frequency. In such embodiments, at least some of the plurality of electrodes may optionally be disposed in a fixed array, wherein the two electrodes of the plurality of electrodes are symmetrically disposed in corresponding opposite sides of the fixed array.

In some embodiments, the step of delivering an actuation signal includes the step of beginning to deliver the actuation signal to each electrode after a delay relative to an onset of the correlated audio input to the subject. In some such embodiments, the delay is the same throughout the sequence of tones. In other such embodiments, the delay varies from 30 milliseconds to 950 milliseconds, from 30 milliseconds to 50 milliseconds, or from 550 milliseconds to 950 milliseconds. In any of these embodiments, the plurality of actuation signals may have intensities based on a threshold of sensory perception of the subject.

Another aspect of the invention provides a method of reducing anxiety in a subject independent of a reduction in tinnitus in the subject. In some embodiments, the method includes the steps of: providing an audio input to the subject; producing a plurality of actuation signals correlated with the audio input; delivering an actuation signal of the plurality of actuation signals to each of a plurality of electrodes in contact with a tissue surface of the subject's head to provide tactile stimuli to the tissue surface; and reducing anxiety in the subject to a degree greater than a reduction in anxiety related to any reduction of tinnitus in the subject.

In some embodiments, the audio input includes a sequence of tones in which at least one tone has a frequency of about 100 Hz, at least one tone has a frequency of about 500 Hz, and other tones have frequencies in a range of about 100 Hz to about 500 Hz.

In some embodiments, the audio input includes a sequence of tones such that the tones are separated by an inter-tone time of about 80 milliseconds to about 2 seconds. In some such embodiments, each tone in the sequence of tones is presented about every 80 milliseconds. In other such embodiments, each tone in the sequence of tones is presented about every 2 seconds.

In some embodiments, the audio input includes a sequence of tones in which each tone has duration of about 15 milliseconds to about 500 milliseconds. In some such embodiments, each tone in the sequence of tones has a duration of about 15 milliseconds. In other such embodiments, each tone in the sequence of tones has a duration of about 500 milliseconds.

In some embodiments, the audio input includes a sequence of tones in which each tone in the sequence of tones fades out as the tone ends.

In some embodiments, the audio input includes a sequence of tones and noise. In some such embodiments, the noise includes broadband noise having a range of about 100 Hz to about 8000 Hz. In other such embodiments, the noise includes low frequency noise having a range of about 100 Hz to about 500 Hz.

In some embodiments, each actuation signal includes a pulse train. In some such embodiments, the pulse train has a duration of about 12-15 milliseconds. In other such embodiments, each pulse in the pulse train has a duration of about 5-210 microseconds.

Some embodiments include the optional further step of adjusting the actuation signals to a level of sensory perception of the subject.

In some embodiments, the electrodes are disposed in a fixed array. In such embodiments, the step of delivering an actuation signal may include the step of delivering an actuation signal to an electrode at a position in the array corresponding to a frequency of the correlated audio input.

In some embodiments, each electrode in the plurality of electrodes corresponds to a frequency bin within the frequency range of the audio input, and the step of delivering an actuation signal includes the step of delivering each actuation signal to an electrode having a frequency bin corresponding to a frequency of the correlated audio input simultaneous with providing the correlated audio input to the subject at such frequency. In some such embodiments, the step of delivering an actuation signal may also include the step of delivering the actuation signal simultaneously to two electrodes of the plurality of electrodes, each having a frequency bin corresponding to the frequency of the correlated audio input and simultaneous with providing the correlated audio input to the subject at the frequency. In such embodiments, at least some of the plurality of electrodes may optionally be disposed in a fixed array, wherein the two electrodes of the plurality of electrodes are symmetrically disposed in corresponding opposite sides of the fixed array.

In some embodiments, the step of delivering an actuation signal includes the step of beginning to deliver the actuation signal to each electrode after a delay relative to an onset of the correlated audio input to the subject. In some such embodiments, the delay is the same throughout the sequence of tones. In other such embodiments, the delay varies from 30 milliseconds to 950 milliseconds, from 30 milliseconds to 50 milliseconds, or from 550 milliseconds to 950 milliseconds. In any of these embodiments, the plurality of actuation signals may have intensities based on a threshold of sensory perception of the subject.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 28A-C shows the stimulus protocols for PS1, PS2, and PS3, respectively, from the TENT-A1 study

DETAILED DESCRIPTION

Figure 1:
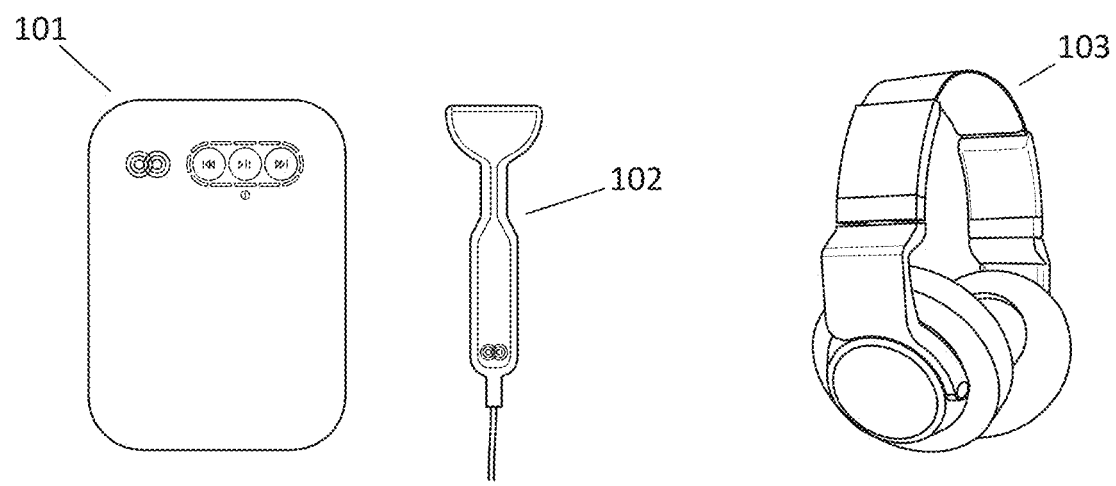
FIG. 1 is a system in accordance with the present invention.

The aspects of the technology mentioned above, as well as additional aspects, will now be described in greater detail. The aspects may be used individually, all together or in any combination of two or more, as the technology is not limited in this respect. The present invention combines auditory and somatosensory bimodal stimulation to improve the symptoms of a neurological disorder of the auditory system. Neurological disorders of the auditory system include for example tinnitus, hyperacusis, misophonia or phonophobia. For convenience only, tinnitus is referred to in the examples below, however it will be appreciated that the systems described may be extended to any of the disorders. A sample system in accordance with the invention and as shown in FIG. 1, including a stimulus generation unit 101 or controller and a somatosensory stimulation unit 102. The controller receives an audio signal as an input and generates a plurality of actuation signals representative of the audio signal. This plurality of actuation signals are delivered to the somatosensory stimulation unit 102. Controller 101 also generates a corresponding binaural modified audio signal for delivery to a subject being treated. Delivery of the modified audio signal is carried out using headphones or audio transducers 103 as shown in FIG. 1. While shown as part of the system in FIG. 1, this is as an example only and the system may be supplied without the headphones. While these headphones are shown as over the ear headphones it will be appreciated that any other audio delivery mechanism may be used for example loudspeakers located proximal to the patient, bone conduction transducers, cochlear implants, in ear audio transducers such as in-ear headphones or hearing aids, sound-from-ultrasound technology or over-ear audio transducers. The headphones shown in FIG. 1, in an embodiment, are arranged to deliver stereo audio having a −3 dB frequency response of 20 Hz to 20 kHz, and a dynamic range of >90 dB. The auditory and somatosensory stimulation are delivered substantially simultaneously to a patient. This simultaneous delivery introduces a fixed delay between audio and somatosensory (up to +/−50 ms). Alternatively, a random variation in delay between audio and somatosensory stimuli (up to +/−50 ms) with a rectangular probability density function, or up to a standard deviation of 20 ms for a Gaussian probability density function) may be introduced to cover a wide range of latencies over the course of a treatment session.

Somatosensory Stimulation Unit

The somatosensory stimulation unit in a preferred embodiment is an intra oral device (IOD). The IOD of FIG. 1 is dimensioned to be located on the tip (dorsal anterior region) of the tongue of the subject undergoing treatment. It will be appreciated however, that the somatosensory device may also be dimensioned to be located on any part of the subject wherein a relevant nerve for the treatment of the neurological disorder can be stimulated. For example, the somatosensory device may be configured and arranged to stimulate one or more nerves transcutaneously by, e.g., being positioned on the cheek (to stimulate the maxillary branch of the trigeminal nerve), on the jaw (to stimulate the mandibular branch of trigeminal the nerve), on the forehead (to stimulate the ophthalmic branch of the trigeminal nerve), on the neck (to stimulate the sub-mandibular branch of the trigeminal nerve), on the ear or pinna (to stimulate the vagus nerve), on the lips (to stimulate the mandibular branch of the trigeminal nerve), on the shoulders and/or neck (to stimulate the accessory nerve and/or the cervical spine nerves C1 and C2). The somatosensory device may also be configured and arranged to stimulate one or more nerves transmucosally by, e.g., being positioned on the dorsal-anterior region of the tongue (to stimulate the lingual mandibular branch of the trigeminal nerve), on the ventral-anterior region of the tongue (to stimulate the hypoglossal nerve), on the gums (to stimulate the maxillary branch of trigeminal nerve). The somatosensory unit may be configured and arranged to stimulate one or more nerves without physically contacting the nerves (e.g., using electromagnetic stimulation such as repetitive transcranial magnetic stimulation (rTMS)) at any of the transcutaneous and transmucosal sites listed above or by stimulating the trigeminal nuclei, cochlear nuclei or auditory cortex. The somatosensory device may also be implantable at any of the transcutaneous or transmucosal sites listed above, or in a position to stimulate the cochlear/auditory nerve, the cochlear nuclei, the trigeminal nuclei, the auditory cortex, or the vagus nerve.

In the embodiment shown in FIG. 1, the somatosensory stimulation unit is an intra oral device (IOD). The configuration shown in FIG. 1 relates to a first embodiment wherein the stimulus generation unit is located remote from the IOD at the control unit 101. In the examples below, this configuration is referred to as MB1. In an alternative configuration, referred to as MB2, the stimulus generation unit may be located local to the IOD 102, for example using a microcontroller or other programmable device to generate the stimuli.

Figure 2:
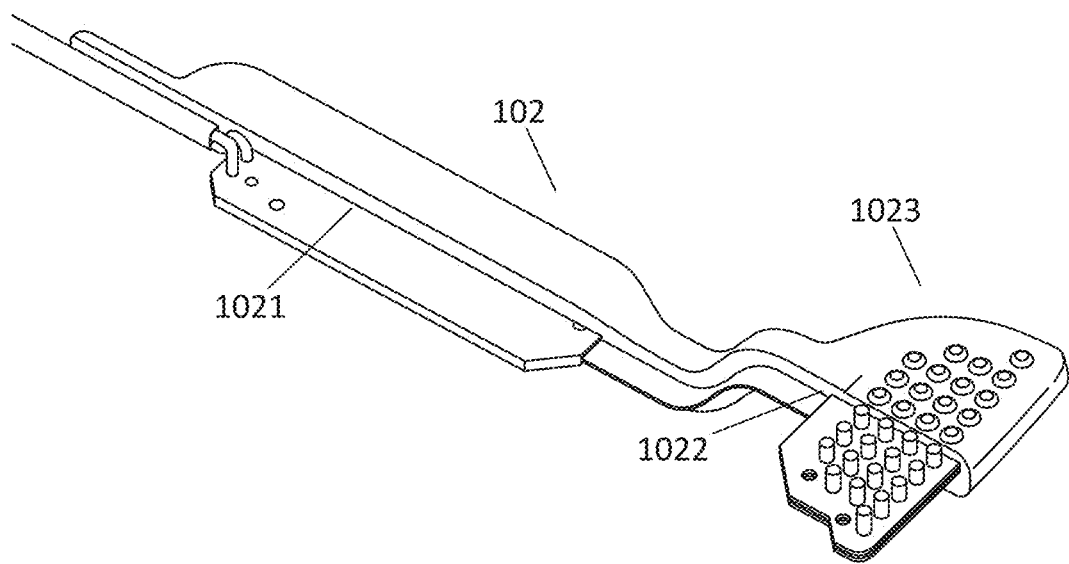
FIG. 2 is an intra-oral device in accordance with an aspect of the present invention

The IOD or somatosensory stimulation unit includes an array of stimulators 1022 each of which can be independently actuated to apply a somatosensory stimulation to a subject synchronously with the modified audio signal. In the MB1 configuration where the IOD is controlled by the controller 101 it will be appreciated that a comparator is required for each stimulator in the array in order to drive each stimulator or electrode. These comparators may be located on the circuit board in the controller 101. In the MB2 configuration, the microcontroller is configurable to drive the electrodes or stimulators directly, said microcontroller and support components may be located on printed circuit board 1021. This configuration minimizes the component count and thus the cost. The PCB 1021 and the array 1022 as shown in FIG. 2 are encapsulated within a molded unit 1023. In an embodiment, the molded unit is over molded. Such a molding process is suitable for an injection molding process, thus minimizing the cost of the IOD. It will be appreciated that to seal the IOD, a Parylene C coating for example may be applied to the PCB before over molding to seal it. Parylene is a hydrophobic polymer microfilm applied by chemical vapor deposition. Parylene dimers are vaporized and converted to a monomer at 690° C. It is then introduced to a vacuum chamber where it forms a polymer coating at room temperature. Applying a Parylene C layer of 12-15 µm seals the IOD and mitigates the risks associated with saliva ingression to the PCBA, leaching toxins, egressing back out, and being ingested by the subject.

Figure 3:
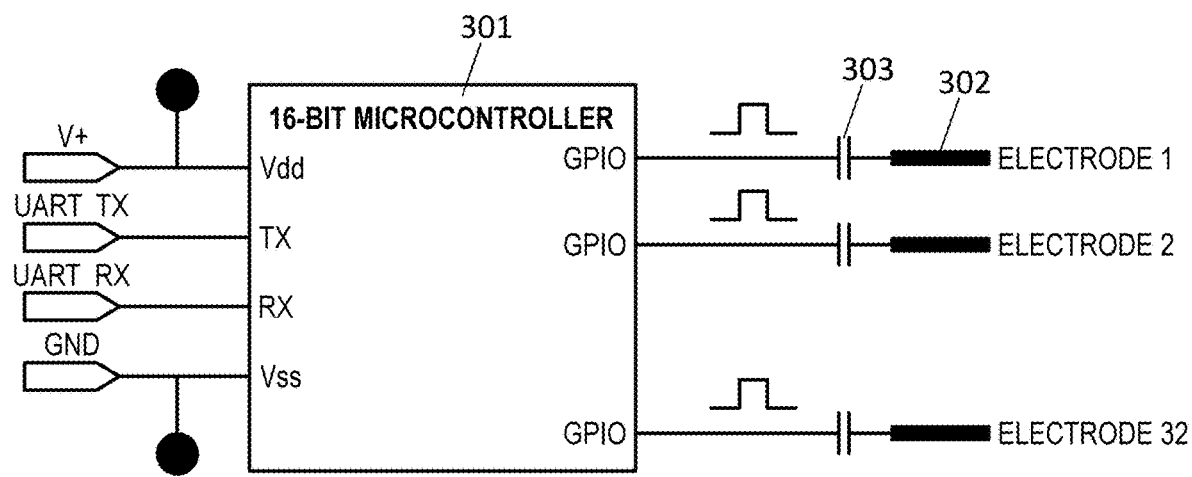
FIG. 3 is a microcontroller configuration in accordance with an embodiment of the present invention.

To generate a strong percept or sensation using the IOD array stimulation in the MB2 configuration, a peak driving voltage of at least 5V may be required. An exemplary microcontroller arrangement is shown in FIG. 3. The microcontroller 301 is a 16 bit microcontroller, however, it may also be an 8 bit or 32 bit microcontroller, an FPGA, custom chip or the like. The microcontroller includes a plurality of inputs and a plurality of outputs 302 arranged to drive each individual electrode in the stimulator array. Each line driving the electrodes has a capacitive element 303 thereon to prevent direct currents from flowing through the subject.

In the MB1 configuration the power supply provided to the voltage input of the IOD is provided by the controller or stimulus generation unit remote from the array. In the alternative MB2 configuration if the IOD is powered by the controller, no additional regulation circuitry is required within the IOD itself and accordingly, the component cost and requirement for the IOD is reduced. A local decoupling capacitance (not shown) may be provided on the MCU supply rail to supply worst cast transients due to electrode drive switching. In the configuration proposed, the MCU 301 drives each electrode by way of the series capacitor 303 on the drive line from the GPIO to the electrode. This configuration facilitates a subset of electrodes to be active at any given instance in time, thereby allowing all other electrodes to act as a stimulus current return path.

The IOD may be detachable from the controller or may be integral thereto. A Universal Serial Bus, USB, optionally with custom overmolding, or other connector may be provided for connecting to the controller. This other connector may prevent connection to non-medical equipment. The top surface of the electrode array within the encapsulation 1023 that makes contact with the mucosal membrane is masked so an electrode-membrane interface is unaffected by the coating process. It will be appreciated that the masking material must be biocompatible. Parylene C as described above is chemically inert and biocompatible.

While described herein as intraoral, it will be appreciated that a suitable array may comprise two or more arrays. These arrays can be contained in separate devices and for example may be located across the back of the neck, or split between one side of the face (jaw) and the opposing side of the face. In an additional embodiment, the somatosensory stimulation unit also comprises a second array comprising at least two stimulators (not shown in the figures). These stimulators are in an arrangement, arranged relative to the array of stimulators and configured to deliver a pseudo stimulus to the subject. This pseudo-stimulus includes additional stimulus channels which are configurable to provide a sensation of an effect to the patient but which are not part of the therapeutic stimulus. The purpose of these is in cases where the main stimulus delivered by the first array is not perceptible, or weakly perceptible. The pseudo stimulus can be activated to improve or increase the sensation perceived by the patient. Further, this facility assists in clinical trials where a "fake" treatment is required. This pseudo stimulus may be implemented with a single stimulus or two stimuli channels, however any number of stimuli channels may be facilitated. In a configuration the pseudo stimulus is asynchronous to any auditory stimulus. Further it may have a low duty cycle relative to the therapeutic stimulus. Furthermore, the pseudo stimulus may be blocking in nature.

In an alternative embodiment, said pseudo stimulus can be elicited through the IOD 102 without any additional stimulators. This is achieved by multiplexing in time the pseudo stimulus with the treatment stimulus. In this scenario a mark:space ratio of at most 10% would be required to impart significant stimulus percept to the subject, while delivering the treatment stimulus for at least 90% of the treatment session duration. Some considerations in the design of a suitable audio signal for auditory stimulation of a subject are as laid out in Table 1 below.

In a first example (MB1), two audio tracks were chosen, namely "Forest Raindrops" by Relax With Nature as the foreground, broadband sound and Erik Satie, "Gnossiennes" and "Gymnopodies" performed by Reinbert de Leeuw. The mixing was performed as follows: Both audio tracks are extracted to 16 bit 44.1 kHz way files and normalized to −0.1 dB. Waves L3 compressor may be used on both, with a threshold setting of −12 dB, no dither, other settings default. The amplitude of the Satie was reduced by 18 dB, extra reverb applied (to enhance the illusion of the music coming from the distance) and was then mixed with the Forest Raindrops with an overall gain of −1 dB to avoid saturation during the mixing. The resulting mix was truncated to 30 minutes, and a short lead in crescendo and lead out decrescendo, before being exported as a 16 bit 44.1 kHz .wav file.

In an alternative example (MB2) the two soundtracks chosen included "Forest Raindrops" by Relax With Nature as the foreground, broadband sound and Erik Satie, "Gnossiennes" and "Gymnopodies" performed by Therese Fahy (the applicant commissioned Therese Fahy to perform these works, which were recorded in RTE Radio Studio 1 on the 7th and 8th January 2015, on a Steinway Grand piano). The mixing was performed as follows: Both audio tracks were extracted to 16 bit 44.1 kHz way files and normalized to −1 dB (to pre-compensate for the overall gain reduction of −1 dB applied in the first configuration's audio mixing). Waves L3 compressor was used on both, with a threshold setting of −12 dB, no dither, other settings default.

TABLE 1

| Audio stimulation design constraint | Rationale |
| --- | --- |
| The audio stimulus should be spectrally broad | To stimulate as many of the afflicted auditory pathways as possible |
| The audio stimulus should contain a high density of fine-grained temporal sounds | So that the auditory processing structures can make frequent correlations between the sound and the electro-tactile stimulation (ETS). |
| The fine-grained sounds within the audio stimulus should be randomly spread in the temporal and spectral domains, | This will ensure that the spatial and temporal characteristics of the somatosensory stimulation (derived from the audio) will be also random, thereby facilitating a neuromodulation-only mode of action. |
| The audio stimulus should promote a sense of relaxation in patients | To maximize patient's comfort<br>To reduce patient's stress levels<br>To maximize patient's tolerance of the treatment |
| The audio stimulus should eliminate repetition within the period of a standard treatment session (30 minutes) | To minimize boredom, thereby increasing the patient's tolerance of the treatment<br>To increase patient's attentiveness during the treatment |
| The audio stimulus should have limited dynamic range, limited close to what the dynamic range of ETS perception on the tongue is. | So that the mapping to the ETS pattern results in a relatively consistent stimulus intensity.<br>To maximize the periods during which the affected auditory structures are stimulated, especially in patients that have significant hearing loss in certain bands.<br>There is no basis to believe that wide dynamic range would have any additional benefit to the patient. |
| The audio stimulus should contain a musical sound track mixed with the broad band foreground, such that it sounds to the patient that the source of the music is originating from a spatial location that is far away. For example, the broadband noise may include a mixture of speech. | To increase patient's attentiveness during the treatment, thereby helping to promote neuroplasticity<br>To help promote relaxation in the patient |
| The audio stimulus should be filtered to compensate for their hearing loss, or band-boost filtered at a frequency that is close to the patient's hearing profile roll-off frequency, or to their tinnitus match frequency if their hearing is normal | To boost the stimulus, and resulting neuromodulation in the region of the patient's hearing deficit, or at a frequency that most closely matches their tinnitus dominant frequency. |
| The audio stimulus should be stereo | To maximize patient's comfort by simulating a sense of space (mono audio through headphones can make the sound appear as though it emanates from a single, central point)<br>To facilitate adequate auditory stimulation for patients that have an asymmetrical hearing loss or tinnitus loudness. |

Four versions of the soundtrack were created:
With the Satie mixed at an amplitude of −12 dB
With the Satie mixed at an amplitude of −15 dB
With the Satie mixed at an amplitude of −18 dB
With no musical component in the mix The resulting mixes were truncated to 31.5 minutes, and a short lead in crescendo and lead out decrescendo, before being exported as a 16 bit 44.1 kHz .wav files.

The files above are examples only and it will be appreciated that other combinations of audio stimuli could also be implemented as long as they meet the design criteria set out above. The system as described above may also have the facility to select one of a multiple of files. These files may be selectable by the subject.

Following the determination of the audio input, an additional audio stimulus filtering is implemented. Most tinnitus patients suffer from a hearing loss at one or more frequencies, with the tinnitus most commonly associated with the side ipsilateral to their hearing loss. In order to ensure there was additional auditory stimulation in the frequency bands of highest hearing loss and/or their tinnitus match frequency, a boost filter is implemented to facilitate compensation for the relevant frequency bands.

The constraints of the filtering include:
To have the center frequency configurable by the clinician when the device is being fitted to the patient, where the set of available configuration frequencies is also covered by a standard high-frequency audiometer (250, 500, 750, 1000, 1500, 2000, 3000, 4000, 6000, 8000, 10000, 12500 Hz etc.)
To boost the gain of the audio by 12 dB at the center frequency (so that a standard bi-quad filter implementation could be used)
To have a fixed boost bandwidth (in proportion to the center frequency), of half the center frequency.

Accordingly, a set of filters is configurable. To meet the set of constraints above the filters are configurable as follows (this example represents the MB2 configuration) in Table 2. The audio stimulus filtering in the MB1 configuration is the same, except the 10 kHz and 12.5 kHz bands were not utilized, because at the time only a standard audiometer was used (audiological assessments conducted up to and including 8 kHz). The filters are examples only, and in this case designed for ease of implementation and low processing power to implement. These filters spectrally modify the audio input to compensate for a deficit in the hearing profile. For example applying a band boost filter with center frequency correlated to fall-off frequency as determined by the patient's audiogram will compensate for the deficit. A band boost filter may be calibrated in accordance with the steepest roll off of the audiogram of the patient with the half power bandwidth of the band boost filter between 0.5 and 1.5 octaves normalized to the center frequency, and with a boost magnitude of at least 12 dB.

TABLE 2

| Filter Number | Center Frequency [Hz] +/− 2% | −3 dB Bandwidth [Hz] | Boost Ratio |
| --- | --- | --- | --- |
| 1 | 250 | 125 | +12 dB |
| 2 | 500 | 250 | +12 dB |
| 3 | 750 | 375 | +12 dB |
| 4 | 1000 | 500 | +12 dB |
| 5 | 1500 | 750 | +12 dB |
| 6 | 2000 | 1000 | +12 dB |
| 7 | 3000 | 1500 | +12 dB |

TABLE 2-continued

| Filter Number | Center Frequency [Hz] +/− 2% | −3 dB Bandwidth [Hz] | Boost Ratio |
| --- | --- | --- | --- |
| 8 | 4000 | 2000 | +12 dB |
| 9 | 6000 | 3000 | +12 dB |
| 10 | 8000 | 4000 | +12 dB |
| 11 | 10,000 | 5000 | +12 dB |
| 12 | 12,500 | 6250 | +12 dB |

Alternatively, the filter may be a boost filter calibrated based on the inverse of the audiogram of the subject in the ipsilateral ear and the filter may be configured to compensate for deficits of at least 30 dB and operable in the range 500 Hz to 16 kHz. It will be appreciated that other filter implementations can be implemented that are better at compensating for the subject's hearing loss.

Method of Auditory Stimulation

It will be appreciated that the use of high-fidelity over-ear headphones coupled with the necessary signal processing is a suitable method of auditory stimulus delivery in accordance with the present invention, because of the widespread tolerance by the users/patients to them and the high degree of comfort they afford to the patient.

In particular situations, it may be preferable to use other transducers, including hearing aids, proximal loudspeakers, and cochlear implants. For example, if the patient has a middle ear disease or other condition that results in a significant conductive hearing loss, a bone conduction transducer may be an acceptable alternative. In this situation, the inner ear mechanisms (including the cochlear function) may be relatively unaffected, and so auditory stimulation via bone conduction transducers would enable such patients to benefit from the treatment. In an alternative scenario, for example, wireless headphones are unsuitable where the patient suffers from electromagnetic hypersensitivity (EHS), proximal loudspeakers or wired headphones may be used. Sufferers of electromagnetic hypersensitivity (EHS) tend to be particularly affected by the knowledge that they are in close proximity to RF sources. In an alternative scenario, for example where the patient has difficulty finding a location that is suitably quiet, in-ear sound-isolating earphones such as Shure SE215 or over ear noise cancelling headphones may be used. It will be appreciated that some patients are significantly affected by tinnitus levels that are less that 10 dB HL, and where there is the requirement that their tinnitus is not over masked during treatment, the background noise levels may need to be 20 dBA or less. Many patients live in environments that have consistent noise levels well above this level. In an alternative scenario, for example, where the patient has profound SNHL in ears that are also affected by tinnitus, cochlear implants may provide an alternative. This is noted where the hearing loss is sensorineural and profound, such as in cases of congenital deafness, acoustic or vibration transducers may provide no stimulus to the auditory pathways. In such cases, cochlear implants may provide the only means of stimulation the auditory branch of the VIII nerve. In an alternative, where the patient has a phobia of wearing headphones, or the patient has a dermatological condition that prevents the use of contact devices around the ear or head, proximal loudspeakers may be used.

Of the many methods of delivering somatosensory stimulation to the V cranial (trigeminal) nerve, electrical stimulation (commonly referred to as electro-tactile stimulation, ETS) is implemented in accordance with the present invention for the following reasons:

It is highly versatile

A high degree of control of the nerve depolarizations is possible, by controlling the timing, amplitude, topography and delivery mode (voltage vs. current mode) of the electrical stimulus.

Devices that transduce somatosensory stimulation electrically can be manufactured cost effectively (as compared with electro-mechanical methods of transduction for example)

Other methods of somatosensory stimulation can also be used, for example

Vibration transduction (e.g., via an array of vibrating pins)

Force transduction (e.g., via an array of force-controlled pins, akin to an electronic Braille display)

Such methods can be used to in situations where electrical stimulation is not feasible, for example:

During research investigations where the effects of stimulation need to be evaluated simultaneous to fMRI.

In situations where it cannot be ascertained if the level of electrical stimulation is too high (over stimulation), or too low (sub-threshold stimulation). This is especially pertinent if the mechanism of action (MOA) is primarily at sub-cortical levels, where the optimum level of electrical stimulus may in fact be lower than that which is perceptible (since perception occurs at the cortical level). It is also pertinent where the frequency of the electrical stimulus is so high that it keeps the target nerve fibers in a constant state of depolarization (yet still elicits a percept due to the paraesthesia effect), or where the amplitude of the electrical stimulus is so high that the field intensity under electrodes adjacent to the active electrode that non-targeted nerve fibers are being depolarized.

Mechanical stimulation can be easily set to a level that is neither too high, nor too low, as the qualitative level of perception the patient reports will be commensurate with the degree of nerve impulses passing through the sub-cortical structures.

In accordance with the embodiments of the present invention, the somatosensory stimulation is applied to the anterio-dorsal surface of the tongue. It will be appreciated that the tongue is a mucosal surface that is coated with a replenishing electrolyte (saliva) that enhances transcutaneous electrical stimulation. Furthermore, the anterio-dorsal surface of the tongue possesses one of the highest somatic nerve densities in the human body and as a result has a disproportionately large representation in the somatosensory homunculus. Unlike with many currently existing neuromodulation technologies for treating neurological conditions (e.g., vagus nerve stimulation for the treatment of Tinnitus, (De Ridder, Dirk, et al. "Safety and efficacy of vagus nerve stimulation paired with tones for the treatment of tinnitus: a case series." *Neuromodulation: Technology at the Neural Interface* 17.2 (2014): 170-179), the tongue can be stimulated without any surgical intervention.

The lingual branch of the trigeminal nerve innervates the anterior surface of the tongue. Studies have demonstrated that there are important anatomical and functional links between the trigeminal nerve and central auditory structures, such as the cochlear nuclei. However, while described herein with reference to the anterio-dorsal surface of the tongue, other sites of stimulation could be used, in particular sites that allow transcutaneous stimulation of various branches of the trigeminal nerve, vagus nerve, or C1/C2 nerves.

One of the key parameters with respect to implementing bi-modal neuromodulation systems is that of the signal bandwidth represented. For example, the information rate of the auditory stimulus can be set very high, since the human hearing apparatus is capable of decoding very complex sounds.

Perceptual encoding of complex auditory signals can only achieve high fidelity with 64 kbits/s or higher for 16 bit dynamic range, 12 kHz bandwidth (24.050 kHz sample rate and covering an 8 octave range from about 50 Hz to 12 kHz), even when utilizing the most advanced perceptual encoding algorithms (e.g., AAC, Vorbis/OGG).

As will be described later, the perceptual encoding dynamic range for amplitude via electro-stimulation on the tongue is approximately 9 levels including zero (which can be represented digitally with 4 bits of information), and the frequency range of operation limited to between 500 Hz and 8 kHz (a range that spans 4 octaves).

Therefore, a minimum 8 kBits/s (==64 kBits*(4/16)bits* (4/8) octaves) of equivalent information would need to be encoded into the somatosensory domain for high-information stimulation.

Audio to Somatosensory Mapping

Figure 17:
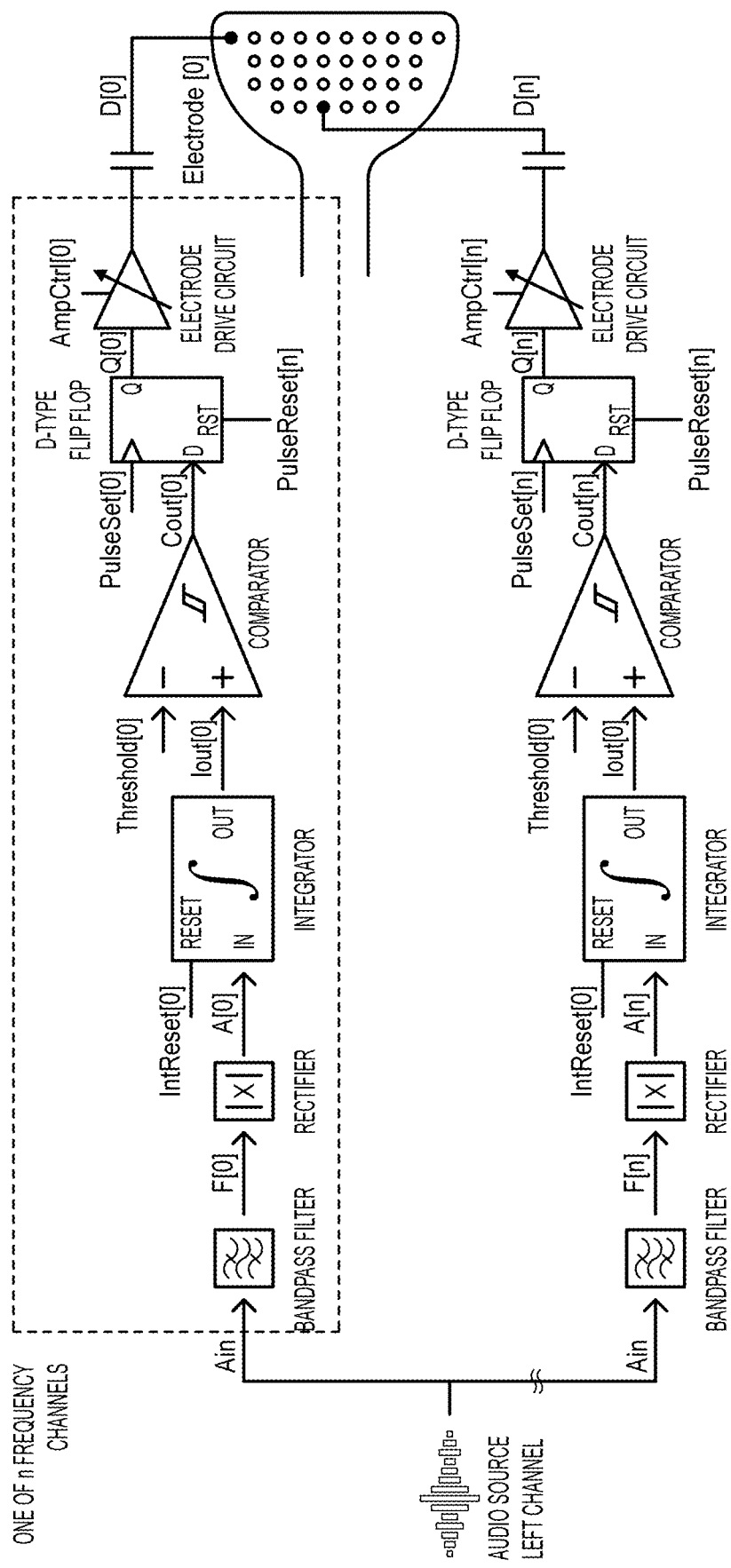
FIG. 17 is a schematic of an alternative audio to somatosensory mapping.
Figure 18:
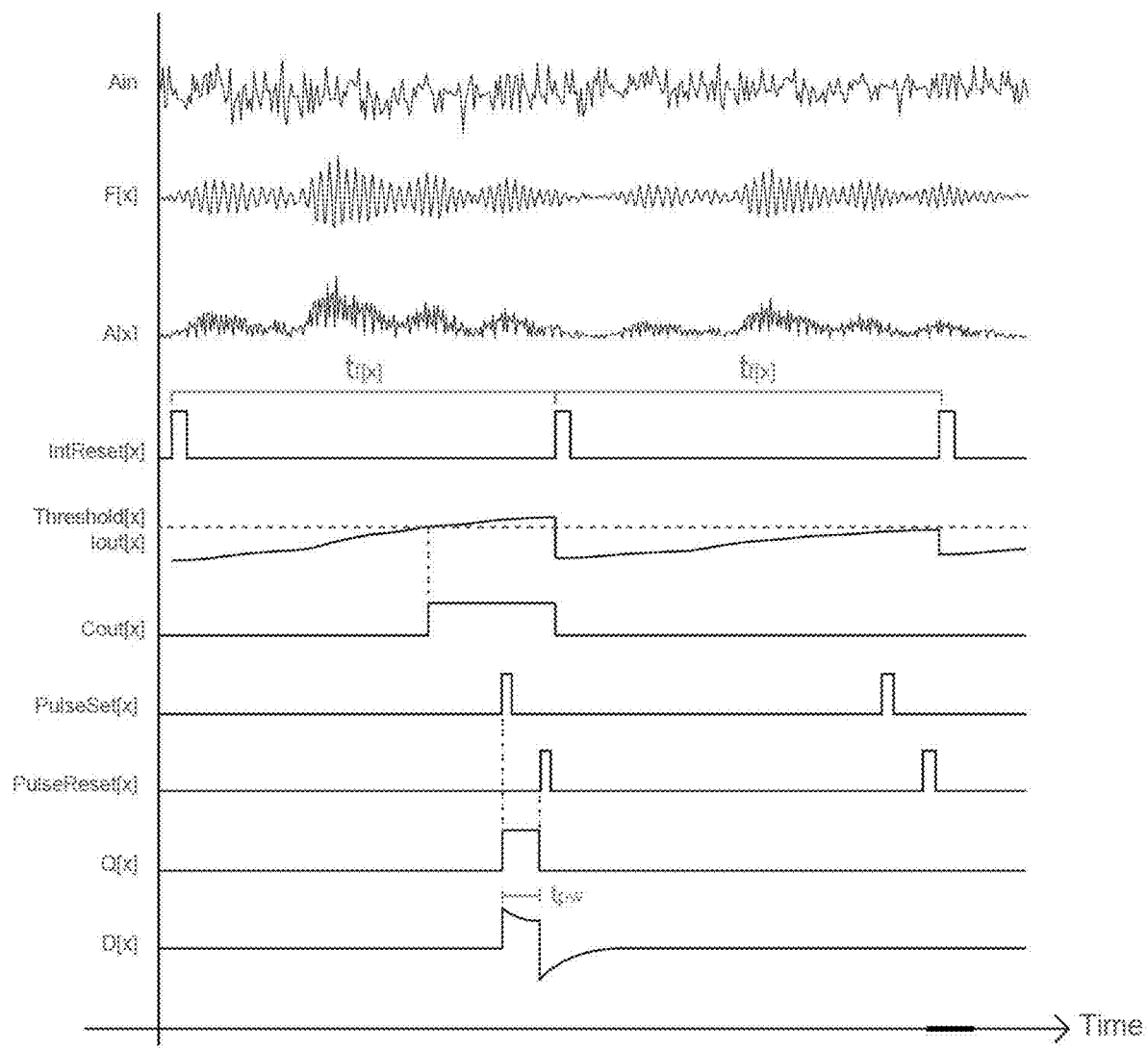
FIG. 18 is a timing diagram of alternative audio to somatosensory mapping.

Several types of mapping between the audio and somatosensory stimulus are possible, some of which are described in the Table 3 and as shown in FIGS. 17 and 18.

The MB1 and MB2 use spectral transformations with high temporal and low frequency resolution, because of the limited frequency resolution required (critical bands according to the Bark scale, see below) and the resulting efficiency of implementation.

It will be appreciated that both temporal and spectral mapping of the audio to somatosensory stimulation maximizes the probability of high efficacy.

Spectral Mapping

The spectral information can be mapped to somatosensory information in several ways, including:

Pulse position coding of the ETS signals

Pulse amplitude coding of the ETS signals

Tonotopical mapping—one electrode assigned to each frequency region

The MB1 and MB2 use a tonotopical mapping, akin to that which occurs in the cochlea (where differing frequencies cause a tonotopic spread of hair cell stimulation).

In this regard, the auditory stimulus is analyzed as a discrete number of frequency bins, and each frequency bin is assigned to one of a multitude of electrodes in the array, covering the range of frequencies that are typically affected in age related and noise induced hearing loss (as research shows that in most cases subjective tonal tinnitus occurs in a frequency band close to the dip frequency (noise induced hearing loss) or roll-off frequency (for age-related or ototoxicity related sensorineural hearing loss) of the patient.

Spatial Arrangement of Electrodes

Two separate spatial arrangements of the electrodes are considered, each with advantages over the other as outlined in Table 4. For the MB1, as used in the clinical investigations in 2012, the single array approach is used. The single array approach is also useable for the MB2 configuration, however the MB2 can also be configured to utilize the split-array configuration.

TABLE 3

| Mapping Type | Temporal Resolution | Frequency Resolution | Description | Example |
| --- | --- | --- | --- | --- |
| Threshold Detection | Very High | None | Mapping specific temporal events in the audio stimulus to somatosensory events, with no consideration of spectral information. Note: This mapping is amenable to a single electrode (monaural) or dual electrode (split array) arrangement. | Analyzing the energy of the auditory signal over temporally short periods and triggering somatosensory events based on the magnitude of the energy within each period. |
| Spectral | Low | High | Mapping spectral information directly to somatosensory events, with significant blurring of the temporal information | Analyzing the spectral content of the auditory stimulus over temporally long periods, and triggering somatosensory events based on threshold detection of energy at particular frequencies. |
| Spectral | High | Low | Mapping spectral information directly to somatosensory events, while maintaining temporal resolution but limited frequency resolution | Dividing the auditory stimulus into short analysis frames, and estimating the spectral content within each frame and triggering somatosensory events based on threshold detection of energy at particular frequencies within each analysis frame. |
| Spectral | High | High | Mapping spectral information directly to somatosensory events, while maintaining temporal resolution and frequency resolution | Dividing the auditory stimulus into variable length overlapping analysis frames, and estimating the spectral content within each frame (similar to performing a wavelet transform) and triggering somatosensory events based on threshold detection of energy at particular frequencies within each analysis frame. This mapping is covered in an alternative configuration. |

TABLE 4

| | Single array | Split array |
| --- | --- | --- |
| Mechanism of Action (MOA): | Primarily cortical levels | Cortical and sub-cortical levels |
| Advantages: | Electrodes can be used to represent twice as many frequency bands<br>The issue of centering the array is not as critical as in the case for the split array because the in the latter case it is required that the somatosensory stimulation operates on the ipsilateral side only | May be more effective at promoting neuroplastic changes in sub-cortical structures, because the auditory stimulus for each side is matched to the ipsilateral somatosensory stimulus |
| Disadvantages: | May not be as effective at promoting neuroplasticity in sub-cortical structures, because there will be a mismatch between the auditory stimulus and the somatosensory stimulus on the ipsilateral side. | Only half as many frequency bands can be presented with a given number of electrodes<br>Centering the array, such that stimuli affect the ipsilateral side only, poses design challenges in certain embodiments (such as tongue stimulation) |

Somatosensory Stimulation—Spectral Encoding

Given that there is a finite number of electrodes possible in the hardware design, the spectral encoding is such that each electrode maps to a particular frequency bin. The choice of an appropriate division and range that these frequency bins cover is of critical importance to the design of the system.

Four possible choices for the spacing of the frequency bins are considered:
Linear
Logarithmic (base2)
Perceptual (such as a Mel scale)
Bark scale (based on critical bands)

Linear Spectral Encoding

Spectral encoding using linear scale is not optimal because no part of the human auditory system, either in pitch or amplitude, operates on a linear scale (our perception of both pitch and loudness are both on logarithmic scales). A linear scale is very inefficient at representing pitches that extend across such a significant range of our hearing, and as a result would result in highly disproportionate weighting to the higher frequencies in our hearing range than the lower frequencies.

Logarithmic (Base2) Spectral Encoding

A logarithmic (base2) scale is more suitable than a linear scale, especially where the audio stimulus comprises of harmonic music. However, it does not match the physiology of the cochlea very well (as per the Place theory), especially at higher frequencies (where perceptual scales are more appropriate). One advantage however is that chords or harmonics in any musical components would align with patterns of electrodes, whereas with the perceptual scale (such as Mel or Bark scale) only dissonant chords would align with patterns of electrodes.

Perceptual (Mel Scale) Spectral Encoding

One of the most popular perceptual scales to represent the human frequency range is the Mel scale (a scale where pitches are perceptually equidistant from each other) (Stevens, Stanley S. "On the psychophysical law." Psychological review 64.3 (1957): 153;

Stevens, Stanley S., and John Volkmann "The relation of pitch to frequency: A revised scale." The American Journal of Psychology (1940): 329-353). It is based on psychoacoustic experiments on humans, where the resulting steps in the scale are judged equidistant in pitch. It is not linear with respect to log (base2) scale, and as such, the harmonics within simplex or complex tones will not align with frequency bins that are spaced according to the Mel scale, especially at the higher frequencies.

Bark Scale (Psychoacoustic Critical Bands)

A less popular perceptual scale to represent the human frequency range is the Bark scale (a scale where pitches are perceptually equidistant from each other) (Zwicker, Eberhard. "Subdivision of the audible frequency range into critical bands (Frequenzgruppen)." *The Journal of the Acoustical Society of America* (2) (1961): 248). Like the Mel scale, it is based on psychoacoustic experiments on humans, where the resulting steps in the scale are judged equidistant in pitch. However, unlike the Mel scale, it is divided neatly into the critical bands of human hearing (the critical band is the band of audio frequencies within which a second tone will interfere with the perception of the first tone by auditory masking).

In accordance with the embodiments described herein, the MB1 and MB2 embodiments base frequency binning on the Bark scale critical bands when there are limited electrodes available (as in the split array design), and a log (base2) scale when there is less of a limitation on the number of electrodes (as in the single array design).

Somatosensory Stimulus Spectral Bin Limits

In order to make the most efficient use of available resources (in terms of the complexity of the system, the number of available electrodes etc.), the range, or limits, over which the frequency bins are spread required consideration.

Starting at the top frequency, when testing is carried out above 8 kHz, cases of individuals with tinnitus without hearing loss are quite rare (Salvi, R. J., Lobarinas, E. & Sun, W., (2009), "Pharmacological Treatments for Tinnitus: New and Old", Drugs of the Future, 34, 381-400). Accordingly, for both the MB1 and MB2 configurations the upper bound was limited to 8 kHz. The lower frequency was chosen as the 1 percentile corner frequency of the population that suffer from sensorineural hearing loss (Congenital, NIHL, presbycusis, ototoxic induced hearing loss etc.), which is approximately 500 Hz (Congenital cytomegalovirus (CMV) infection & hearing deficit (Fowler, Boppana) 2005, Fowler; CMV A Major Cause of Hearing Loss in Children (2008), http://www.cdc.gov/nchs/data/series/sr_11/sr11_011 acc.pdf (page 7, FIG. 5)).

Arrangement of the Frequency Bins

For a split-array stimulator (split down the medial line of the tongue), and in accordance with the embodiments described herein a minimum of 16×2 electrodes is required (32 electrodes). With the constraints above (covering all critical bands in the range 500 Hz to 8 kHz), the following frequency bins are required (as per the bark scale) [Hz]:

570 700 840 1000 1170 1370 1600 1850 2150 2500 2900 3400 4000 4800 5800 7000

Figure 4:
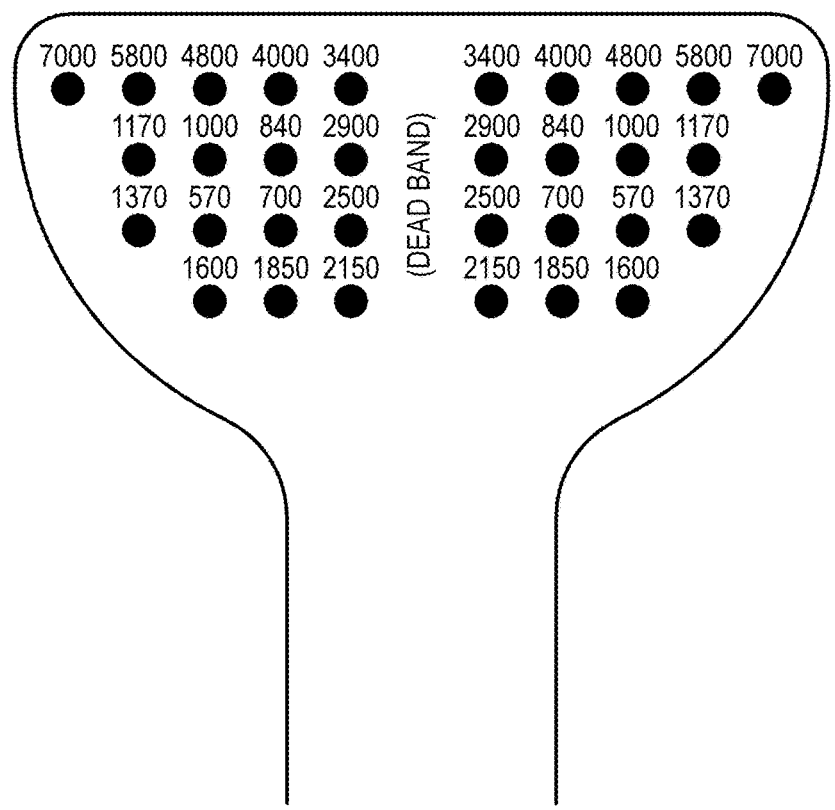
FIG. 4 is a sample layout of a split array in accordance with the present invention.

An electrode array of size 32 electrodes was chosen for the MB1 design to be able to accommodate the split-array design. A deadband may be included between the right side and the left side stimulators. This is illustrated in FIG. 4.

The dorsal anterior region of the tongue, where spatial resolution and sensitivity are at their highest, can easily accommodate the 32 electrodes on a grid spacing of 2 mm.

For a single array design, in order to make use of all 32 electrodes, the frequency bin spacing is decreased such that there are 8 bands per octave, thereby dividing the required frequency range into 32 logarithmically evenly-spaced bands across the full frequency range of interest (500 Hz to 8 kHz). Frequency bins are separable equidistant on a log (base 2) scale to maintain a consonant harmonic relationship between the frequency bins. Within these constraints (8 kHz top frequency, and 8 bins per octave, and approximately 500 Hz for the lowest frequency bin), the following frequency bins are required [Hz]:

545 595 648 707 771 841 917 1000 1091 1189 1297 1414 1542 1682 1834 2000 2181 2378 2594 2828 3084 3364 3668 4000 4362 4757 5187 5657 6169 6727 7336 8000

Figure 5:
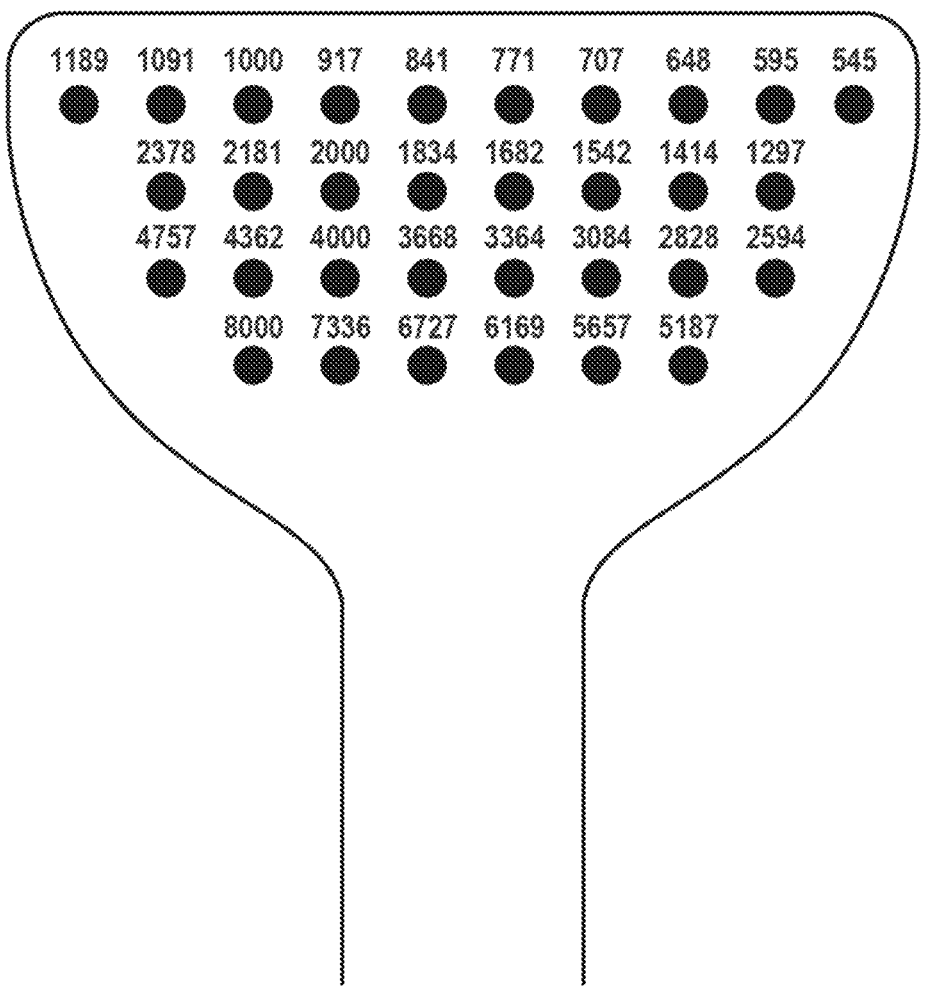
FIG. 5 is a sample layout of a single array in accordance with the present invention.

These frequencies are mapped as shown in FIG. 5 (viewed from the electrode side of the IOD) and are both suitable mappings used in both MB1 and MB2 configurations. As shown the frequencies that are most typically affected in patients with hearing loss related tinnitus (the highest frequencies) are situated on the two bottom rows—this corresponds to the region that is closest to the tip of the tongue and as such is the area of highest somatosensory nerve fiber innervation density.

An alternative arrangement in which the bins are arranged spirally could be used in an alternative embodiment of the device as illustrated in FIG. 4.

Neuromodulation, Perception and Paraesthesia

Somatosensory stimulation may be a trans-mucosal or trans-cutaneous electro-tactile stimulus (ETS). From a neuromodulation point of view, and where the mechanism of action (MOA) is based in sub-cortical regions of the brain, the act of depolarizing somatosensory nerve fibers may be sufficient for the device to be effective, since the depolarizing of the nerve fibers should result in neural spikes reaching one or more of the subcortical structures in the brain. However, depolarizing somatosensory nerve fibers is not always sufficient to illicit a percept and therefore it cannot be assumed that a percept is essential for the stimulation to be effective.

On the other hand, where the MOA is primarily at the cortical levels (e.g., from a perceptual perspective), then it is almost certainly essential that the patient perceives the stimulus for the treatment to be effective.

Even if the MOA is only at sub-cortical levels, it will be appreciated that it is important that the patient can perceive the stimulation for example, so that the patient is aware that the device is operational. If there is no percept, the patient is less likely to comply with the treatment. Feedback from patients that participated in the 2012 trial (using the MB1 device) revealed that a strong percept was important so that they could 'feel the treatment working'. In a further example, the feedback is important to ensure that the electrodes are making the necessary contact with the patient's tongue. Patient feedback about the perceived strength and location of the stimulus is the only way to know that the electrodes are positioned correctly and hence the only way to ensure compliance with the treatment regime. In a further example, this feedback is used to enhance the placebo effect. Even though the placebo effect is not the principal mechanism of action of the device, it is likely to enhance the device's effectiveness for some patients.

The two principal mechanisms of perception from electro-tactile stimulation are:
1. Direct stimulation of nerve fibers innervating the nociceptors and mechanoreceptors, eliciting either vibration, pressure or pain sensations.
2. Overstimulating of nerve fibers thereby maintaining them in a constant, or near constant, state of depolarization resulting in a paraesthesia effect (the sensation arising due to the inhibition of the basal neural pulse train, commonly known as "pins and needles").

It is very difficult to estimate the perceived stimulus intensity from theory alone, since the mechanisms of perception of ETS vary according to so many parameters (amplitude, pulse width, pulse repetition rate, etc., see below for details). Even though there is significant data already available in the literature, it is essential that the values of the parameters relating to perceived stimulus intensity levels are based on in-vivo testing.

In implementing embodiments of the present invention in-vivo testing was performed using the MB1 configuration prior to use in a 2012 clinical investigation, and data was gathered electronically during them. Further in-vivo tests were also performed on the MB2 configuration as part of the design and clinical validation processes.

Somatosensory Stimulation Amplitude Control

Global amplitude control is essential in order to accommodate the natural variation in physiological, physical, and genetic factors affecting the sensitivity, conductivity and perceptual characteristics of the patient population including
   The age of the subject
   The dryness of the mucosal surface the electrodes make contact with
   The concentration of ions in the mucosal surface fluid
   Genetic and physical variations, such as relative thickness of the epithelium layer.
   Medium term and long term adaptation In order to compensate for the sensitivity variation, it is therefore necessary to include a method of stimulation amplitude control so that the intensity of stimulation can be adjusted per patient. The amplitude may be under direct control of the patient to they adjust the intensity to a comfortable level, for example by adjusting the controls on the Control Device, 101.

In a preferred embodiment, the system described herein also includes stimulation amplitude control so that the intensity of stimulation can be adjusted per patient. There are several methods by which the perceptual stimulus intensity can be varied, by controlling the values of stimulus parameters including:
1. The energy of the individual stimulus pulses either by varying the
   a. Voltage/current magnitude of the pulses
   b. Width of the pulses
   c. Polarity of the pulses (anodic versus cathodic)
2. The number of consecutive pulses within the multisensory window of simultaneity (typically no more than 50 ms for auditory-somatosensory).

Of the remaining methods of intensity control (pulse width/pulse amplitude and number of consecutive pulses), it is the number of pulses that is used to vary the amplitude of the stimulus at a high temporal resolution, to increase the effective bandwidth of the stimulus.

MB1 Configuration Amplitude Control

In the current MB1 configuration, a design decision to implement this global stimulation amplitude control was to vary the voltage of the electro tactile pulses. This limits the cost and complexity of the device by requiring only the control of the supply voltage to the ETS drive circuits.

The minimum number of steps required for global stimulus amplitude control is dictated by two parameters:
   The just-noticeable difference for amplitude discrimination of electrical stimulation on the dorsal anterior region of the tongue in humans
   The standard deviation of perceptual intensity due to electrical stimulation on the dorsal anterior region of the tongue across the patient population The overall dynamic range for electric tactile stimulation of the dorsal anterior region of the tongue has been found to be 17.39 dB (SD=2.3 dB), where the dynamic range is defined as the difference between the intensity at the threshold of discomfort and the intensity at the threshold of perception. The corresponding JND within this range was found to be 12.5% of the dynamic range on average, such that 8 different amplitude levels could be discriminated between the threshold of perception and the threshold of discomfort (~2.4 dB per step), but as low as 1.5 dB per step for certain parts of the perceptual range.

In addition, the range of perception threshold varied by 10 dB across all 8 subjects in the experiments. Taking the lower step size of 1.5 dB, and dividing it into the total required range (17.39 dB+10 dB) results in a minimum of 18 steps required.

Accordingly, there are 18 global stimulus amplitude levels in the MB1 design, approximately linearly spaced in terms of energy delivery, but with the lowest non-zero level at a raised pedestal (because lower energy levels were below the threshold of perception for all 5 subjects tested during in-house psychophysics experiments on the MB1 device).

The pulses on the MB1 were constant width (17.7 us), and the voltage varied according to the amplitude setting (under the control of the patient), i.e., basing the stimulus drive circuit on voltage-mode control. The voltage levels utilized, along with the resulting volt-second product (potential to depolarize) are detailed in the table below.

MB2 Configuration Amplitude Control

In the current MB2 configuration, electronic design and economic constraints lead to a pivot in the method for adjusting global amplitude, where the global amplitude is controlled primarily by varying the pulse widths (and maintaining pulse voltage amplitude over a more restricted range).

This change to the somatosensory electrode drive circuit is due to the necessity to migrate the electrode drive circuit from the Control Device to the Intra-Oral Device. This necessity stems from the fact that the passive IOD in the MB1 required a 32-core cable from it to the Control Device. The cost of this cable and associated connectors is very high, and the reliability and flexibility of the arrangement is less than optimal. Moving the electronic drive circuit from the Control Device to the IOD in the MB2 design results in a lower cost and higher reliability product.

Due to practical constraints, the MB2 is based on a low cost microcontroller unit (MCU), with its outputs capacitive coupled directly to the electrodes. This electronic drive circuit change requires that the drive voltage level in the MB2 be limited to between 4.35V (so a low cost boost converter can be used from a 4.2V Lithium Polymer battery), and 5.85V (just below the absolute maximum supply voltage limit of the MCU), whereas in the MB1 it is adjustable from 3V to 11V. This requires that the range of pulse widths in the MB2 design be increased to compensate for the change in range of the pulse voltage. In particular, to maintain equivalency between the stimulation in the MB2 relative to the MB1 configuration it needs to be assured that the pulse energy levels, at maximum stimulus amplitude settings, subjectively yield at least the same perceptual intensity, and that the lower stimulus levels subjectively yield at least as low a perceptual intensity.

Design of the ETS Stimulus Patterns for the MB2 Configuration

Given the constraints above, there are two potential candidates for the ETS pulse profiles:
1. Use one pulse slot per electrode per frame, and vary the pulse width of the pulses as a function of the global stimulus amplitude AND the dynamic amplitude level
2. Use 8 pulse slots per electrode per frame, as in the MB1 configuration, and vary the pulse width according to the global pulse width setting.

In the case of option 1, the maximum pulse width would be
23.2196 ms/32 electrodes=725.6 us That is far too long for the current hardware to support, since there is a physical limit on the size of the electrode series DC blocking capacitors (currently the limit is about 100 nF). Pulse widths longer than 100 us will result in the 100 nF series capacitor being more than 20% discharged by the end of the pulse, and so 100 us is a realistic upper limit for the pulse width. Also, longer pulses will increase the risk of irritation and sensitization to the mucosal surface due to electrolysis by-products under the electrodes, because the longer the first phase of the pulse the less the by-products of the electrolysis reaction will be reversed by the 2nd phase (opposite polarity phase) of the pulse.

Additionally, from an energy perspective, a 100 us pulse should deliver significantly more energy (neglecting the effect of the DC blocking capacitors) than the 17.6 us pulses used in the MB1 configuration.

Going for option 2) above, it is required to squeeze 8 pulse slots for each of the 32 electrodes into the frame period.

The requirement is to set the lowest (non-zero) pulse width to achieve the same charge injection as the lowest amplitude setting on the MB1.

On the MB1, the volt-second product was 17.7 us*3V=53.1 Vus

On the MB2, with the voltage set to 4.35V, the lowest pulse width required is therefore
PWmin=53.1 Vus/4.35V ~=12 us As indicated in the note above, the maximum pulse charge for the MB2 was required to be higher than for the MB1, and a value of 66% higher is used. This equates to $$PW_{max}=V_{max(MB1)}*PW_{MB1}*1.66/V_{MB2}=10.9V*17.7\ us*1.4/4.35V\sim=78\ us$$

In practice, to accommodate for patients that have very high sensitivity, two steps are added below the 12 us level, and the remaining number of steps (15 of) are extended to 78 us, with a slightly exponential curve.

The ETS pulse width can be modified to one of several discrete settings (18 in total, to cover the MB1 range of 18 step), as set out in the table below. Based on feedback from patients using the MB2 device (n=120), in three instances there were situations where the patient could perceive the somatosensory stimulus only weakly even with the level set to maximum. To cater for such patients, an additional 3 steps are included at the top end to extend the range. These additional steps are accommodated by incrementing the pulse voltage (from 4.35V to 4.85V to 5.35V to 5.85V) while keeping the pulse width at the maximum of 78 us. These additional steps are highlighted in bold in the Table 5 below.

The pulse width is under the direct control of the patient. For example, it may be adjusted by pressing stimulus amplitude control buttons e.g. (UP/DOWN button pair) on the Control Device 101.

TABLE 5

Electrical pulse parameters as a function of the global stimulus levels for the MB2 and MB1

| Somatosensory Amplitude Setting | MB2 | | | MB1 | | |
| --- | --- | --- | --- | --- | --- | --- |
| | Pulse Width [us] | Pulse Voltage [V] | Pulse Volt-seconds [Vus] | Pulse Width [us] | Pulse Voltage [V] | Pulse Volt-seconds [Vus] |
| 0 | 0 | 4.35 | 0 | 17.7 | 0 | 0 |
| 1 | 5 | 4.35 | 22 | 17.7 | 3 | 53 |

TABLE 5-continued

Electrical pulse parameters as a function of the global stimulus levels for the MB2 and MB1

| Somatosensory Amplitude Setting | MB2 | | | MB1 | | |
|---|---|---|---|---|---|---|
| | Pulse Width [us] | Pulse Voltage [V] | Pulse Volt-seconds [Vus] | Pulse Width [us] | Pulse Voltage [V] | Pulse Volt-seconds [Vus] |
| 2 | 9 | 4.35 | 39 | 17.7 | 3.5 | 62 |
| 3 | 12 | 4.35 | 52 | 17.7 | 4 | 71 |
| 4 | 15 | 4.35 | 65 | 17.7 | 4.5 | 80 |
| 5 | 18 | 4.35 | 78 | 17.7 | 5 | 89 |
| 6 | 21 | 4.35 | 91 | 17.7 | 5.5 | 97 |
| 7 | 25 | 4.35 | 109 | 17.7 | 6 | 106 |
| 8 | 29 | 4.35 | 126 | 17.7 | 6.5 | 115 |
| 9 | 34 | 4.35 | 148 | 17.7 | 7 | 124 |
| 10 | 39 | 4.35 | 170 | 17.7 | 7.5 | 133 |
| 11 | 44 | 4.35 | 191 | 17.7 | 8 | 142 |
| 12 | 49 | 4.35 | 213 | 17.7 | 8.4 | 149 |
| 13 | 54 | 4.35 | 235 | 17.7 | 9.1 | 161 |
| 14 | 59 | 4.35 | 257 | 17.7 | 9.6 | 170 |
| 15 | 65 | 4.35 | 283 | 17.7 | 9.9 | 175 |
| 16 | 72 | 4.35 | 313 | 17.7 | 10.5 | 186 |
| 17 | 78 | 4.35 | 339 | 17.7 | 10.9 | 193 |
| 19 | 78 | 4.85 | 378 | | | |
| 20 | 78 | 5.35 | 417 | | | |
| 21 | 78 | 5.85 | 456 | | | |

Somatosensory Stimulation Dynamic Amplitude Control

Dynamic amplitude control of the somatosensory stimulation is useable as a means of encoding the relative amplitude of the audio stimulus from which the somatosensory stimulus is derivable. It will be appreciated that this facilitates greatly increasing the information rate of the somatosensory stimulus, so that it can more closely match the information rate of the audio stimulus from which it is derived.

The increase in information rate that can be achieved is essentially limited by the somatosensory perceptual dynamic range of the human tongue.

Previous studies on ETS of the human tongue has shown that the typical perceptual dynamic range is of the order of 17.39 dB+/−2.3 dB from minimum perception threshold to maximum level without discomfort. It was also found that the average Just-Noticeable Difference (JND) for amplitude discrimination is about 2.4 dB (Lozano, Cecil A., Kurt A. Kaczmarek, and Marco Santello. "Electrotactile stimulation on the tongue: Intensity perception, discrimination, and cross-modality estimation." *Somatosensory & motor research* 26.2-3 (2009): 50-63). Therefore about 8 discrete amplitude steps (not including zero) are all that is required to represent the full perceptual dynamic range.

Each of the three methods by which the perceptual amplitude of the tactile stimulation can be modulated are detailed in Table 6.

TABLE 6

| Method of dynamic amplitude control | Suitability | Notes |
|---|---|---|
| Pulse Voltage/Current Modulation | Low | Dynamically adjusting the voltage/current level on a per-pulse basis was ruled out as a viable option in the MB1 and MB2 designs, as it would have increased the complexity and cost of the drive electronic circuit by an order of magnitude. Future incarnations of the technology may utilize this approach however. |
| Pulse Width Modulation | Medium | Dynamically adjusting the pulse width on a per-pulse basis in the MB2 was ruled out because this means of control was reserved for the global amplitude control (to allow the patient to control the stimulation to their level of comfort). |
| Pulse Count Control | High | Dynamically adjusting the pulse count was deemed the most appropriate method of dynamic amplitude control for the following reasons:<br>  The dynamic range of 17.39 dB in 8 discrete steps is feasible, given the frame rate and number of electrodes (see below)<br>  It mitigates the need for expensive, space hungry and power-hungry electronics to drive the electrodes<br>  It retains the ability to adjust the pulse width as a means of global stimulation amplitude (which requires at least 17 discrete steps, see above). |

Method of Pulse Count Control

Pulse count control is achievable in practice by simply varying the number of electrical pulses on any given electrode, in any given frame. This corresponds to a discrete number, or count, of pulses in a burst, where the burst is shorter than the analysis frame length. As long as the duration of the frame is less than or equal to period of sensory integration (period of tactile simultaneity), the pulses are wide enough to depolarize the nerve fibers, and the pulses are spaced far enough apart (i.e., that the neurons can re-polarize in time before the next pulse), the perceived amplitude of the stimulus is proportional to the number of pulses up to and including 6 or 7 pulses (1 Kaczmarek, Kurt, John G. Webster, and Robert G. Radwin. "Maximal dynamic range electrotactile stimulation waveforms." *Biomedical Engineering, IEEE Transactions on* 39.7 (1992): 701-715).

Temporal Transformation of Audio Frequency Components to Somatosensory Stimulus

FIGS. 8 to 14, inclusive, serve to illustrate the transformation between audio and somatosensory stimulation, but is generalized in terms of the number of frequency bins (n) and the number of quantized amplitude levels (q).

These figures illustrate how one of the binaural channels is transformed for use in a split-array stimulator topology. For the unified-array stimulator topology used in the MB1 and MB2, the left and right audio channels are mixed prior to the transformation (with the audio kept as stereo for delivery to the patient via the headphones).

As an example only, the pulse pattern is illustrated for one electrode only (electrode #3 in this case, which corresponds to frequency bin #3).

As per the requirements above, the audio to somatosensory transformation process implementable for both the MB1 and the MB2 is summarized as follows:

The stereo audio signal for the entire treatment session (typically 30 minutes of audio) is first
converted to monaural, by summing the left and right channels and then normalizing for the single array embodiment OR
For the split-array embodiment, the audio is normalized without converting to monaural.
The resulting audio is then divided into overlapping sections of duration $t_w$, corresponding to twice the frame duration, $t_p$
A Blackman tapering (window) function is then applied to each of the audio sections
Then a time->frequency transform is computed on each of the windowed audio sections, to yield frequency domain signals
For the MB1 and MB2, a discrete Fourier transform is useable, however gammatone filters or wavelet transforms can be used in alternative embodiments.
The resulting frequency domain signals are further analyzed according to the pre-determined frequency bins (e.g., as per the Bark scale critical bands as outlined above), to yield an array of n magnitude values such that each magnitude value corresponds to the amplitude of the frequency domain signal for the each of the individual frequency bins.
The array of magnitude values are normalized according to the peak values across the entire set of signals for the whole treatment session, so that for each frequency bin, the magnitude values are normalized to the maximum level.
The resulting normalized magnitude values are further quantized into q discrete levels.
The resulting quantized signals are stored in a way that they can be used to control the number of pulses for each frequency bin (mapped to an individual electrode) within each frame period, $t_p$.

In order to implement this transformation in practice, several parameter values that are used in the MB2 and MB1 must be chosen including:
The frame period, $t_p$
The pulse slot period, $t_{ps}$, which also dictates the maximum ETS pulse width, $t_{pw}$
The audio sample rate, $F_s$
The following sections detail the rationale, constraints and calculations from which these parameter values are defined for the MB1 and MB2 devices.

Optimal Temporal Resolution Calculation

There are several factors to be considered when calculating the optimal temporal resolution of the transformation from audio to tactile stimulation. Many of these factors have already been elucidated in the sections above and are outlined in the following Tables 7 and 8.

TABLE 7

| Parameter | Physiologic Parameter Value | Impact/Constraint on Design of Transformation |
| --- | --- | --- |
| The maximum refractory (re-polarization) period for somatosensory nerve fibers in the dorsal anterior region of the tongue resolution | 2 ms** | The minimum period between pulses on the same electrode must be greater that this period. |
| The perception of tactile simultaneity in humans (the effective window over which our perceptual centers integrates tactile stimulus) | 30 ms* | If the mechanism of action (MOA) is primarily at cortical levels, then the frame period should be longer than this period, so that each somatosensory frame does not blur into adjacent frames. If the MOA is primarily at sub-cortical levels then this need not be an upper limit for the frame period. |

*Geffen, Gina, Virginia Rosa, and Michelle Luciano, "*Sex differences in the perception of tactile simultaneity*." Cortex 36.3 (2000): 323-335.
**Burgess, PR T., and E. R. Perl. "*Cutaneous mechanoreceptors and nociceptors*." Somatosensory system. Springer Berlin Heidelberg, 1973. 29-78,

TABLE 8

| Parameter | MB/MB1 Parameter Value | Impact/Constraint on Design of Transformation |
|---|---|---|
| The number of frequency bins to be represented via somatosensory stimulation | 32 | The frame length should be long enough to accommodate the product of<br>    The number of frequency bins AND<br>    The number of pulses per frame (for dynamic range control)<br>at the maximum pulse width, such that there are no temporally overlapping pulses. |
| The center frequency of the lowest frequency bin to be represented via somatosensory stimulation | 545 Hz | The frame length should be long enough such that there are at least two periods at this frequency (4 periods including the window function), i.e. minimum frame length of 4/545 = 7.4 ms |
| The maximum pulse width required to ensure strong stimulus percept | 17.7 us (MB1)<br>78 us (MB2) | The pulse slots must be long enough to accommodate pulses of these widths |
| The required dynamic range of the tactile stimulus and the number of discrete amplitude steps required within that range | 8 | The frame length should be long enough to accommodate the product of<br>    The number of frequency bins AND<br>    The number of pulses per frame (for dynamic range control)<br>at the maximum pulse width, such that there are no temporally overlapping pulses. |

In addition, several other factors constrain the design of the auditory to somatosensory mapping including:

The nature and design of the electro-tactile stimulation electronics (the IOD electronics).

The maximum pulse energy level that the electrodes can tolerate before significant corrosion sets in due to galvanic action instead of faradic action.

The available voltage, or energy, per pulse (a function of the electronic design topology)

The audio sample rate of the original auditory stimulus from which the somatosensory stimulus is to be derived.

Electrode Topology

In both the MB1 and MB2 configurations the electrode topology is configured in accordance with a number of considerations. In order to reduce the total number of electrodes, and ease the complexity of the drive electronics, the MB2 and MB1 are designed such that the same electrodes also act as the return path electrodes. In other words, a dedicated return electrode is not necessitated, but rather to configure all electrodes apart from the active electrode at a particular point in time to act as joint return electrodes. One consequence of this is that there is less scope for overlapping (simultaneous) pulses—the ideal stimulation paradigm is to have no overlapping pulses, i.e., that only one electrode is ever active at a particular point in time. This ensures that all other electrodes can be configured as the return path for the stimulus current, and with 32 electrodes in total, there will be 31 for the return path. This results in the highest electric field strength directly beneath the active electrode, with a fraction of that field strength under the adjacent (return) electrodes. When the stimulus energy level is set correctly, only nerve fibers within a small spread region surrounding the active electrode will be activated. However, if the stimulus energy level is set too high, then there is the chance of stimulating nerve fibers under adjacent electrodes.

Temporal Resolution Calculations

Pulse Slots

To maintain synchronization with the audio data, one consideration is that the somatosensory pulses should occur at the same timing resolution as the audio samples, i.e., at a resolution of 1/44100s (22.6 uS). To accommodate this, the time axis is divided up into "Pulse Slots" of period $t_{ps}$.

It was determined through validation experiments that a pulse width of 22.6 us was more than enough, even at low drive voltages, to fire the sensory nerves in the tip of the tongue. However, it was also found during validation that that the resulting number of electrotactile pulses gave a very strong, sometimes unpleasant sensation. Another constraint or consideration that places a lower bound on the pulse slot interval is related to the neural repolarization period (2 ms). Allowing for 25% headroom, and since there are 32 electrodes to be serviced, the associated pulse slots can be spread out to cover the entire 2.5 ms repolarization period. Therefore the minimum pulse slot period should be 2.5 ms/32=78 us. The next highest period value that is also a multiple of the audio sample rate is 90.7 us, which results in a pulse slot for every 4 audio samples. So the pulse slot period, $t_{ps}=4/44100=90.7$ us. In practice, there needs to be some dead time between pulse slots, as the microcontroller that generates the pulses will have some overhead. It has been experimentally verified that pulse widths of up to 78 us are possible with a low cost 16 bit MCU running at 0.5 MIPS even when the pulse slot period $t_{ps}=90.7$ us. Therefore, this choice of $t_{ps}$ is suitable for use in the MB2, which requires the MCU in the IOD to be low cost and energy efficient.

Calculating Frame Period

In calculating the minimum frame period the following constraints or considerations are taken into account. Each frame must be able to accommodate 8 pulses (dynamic amplitude), times 32 electrodes times the pulse slot period (90.7 us). Therefore, the frame period $$t_p = n * q * t_{ps} = 32 * 8 * 90.7 \text{ us} = 23.219 \text{ ms}$$

Where
$t_p$ = the frame period.
n is the number of electrodes (32)
q is the number of amplitude bins that the amplitude is quantized to (8)
Since 32 pulses can occur for each pulse slot within a given frame period, the inter-pulse period on any given electrode must be a minimum of $$t_{ipp} = t_{ps} * n = 90.703 \text{ us} * 32 = 2.9 \text{ ms}$$

This is greater than the nominal repolarization period of 2 ms, and so meets the critical requirement that subsequent pulses on any given electrode only occur after the nerve fibers have had sufficient time to repolarize following the previous depolarization.

Pulse Slot Timing

Figure 6:
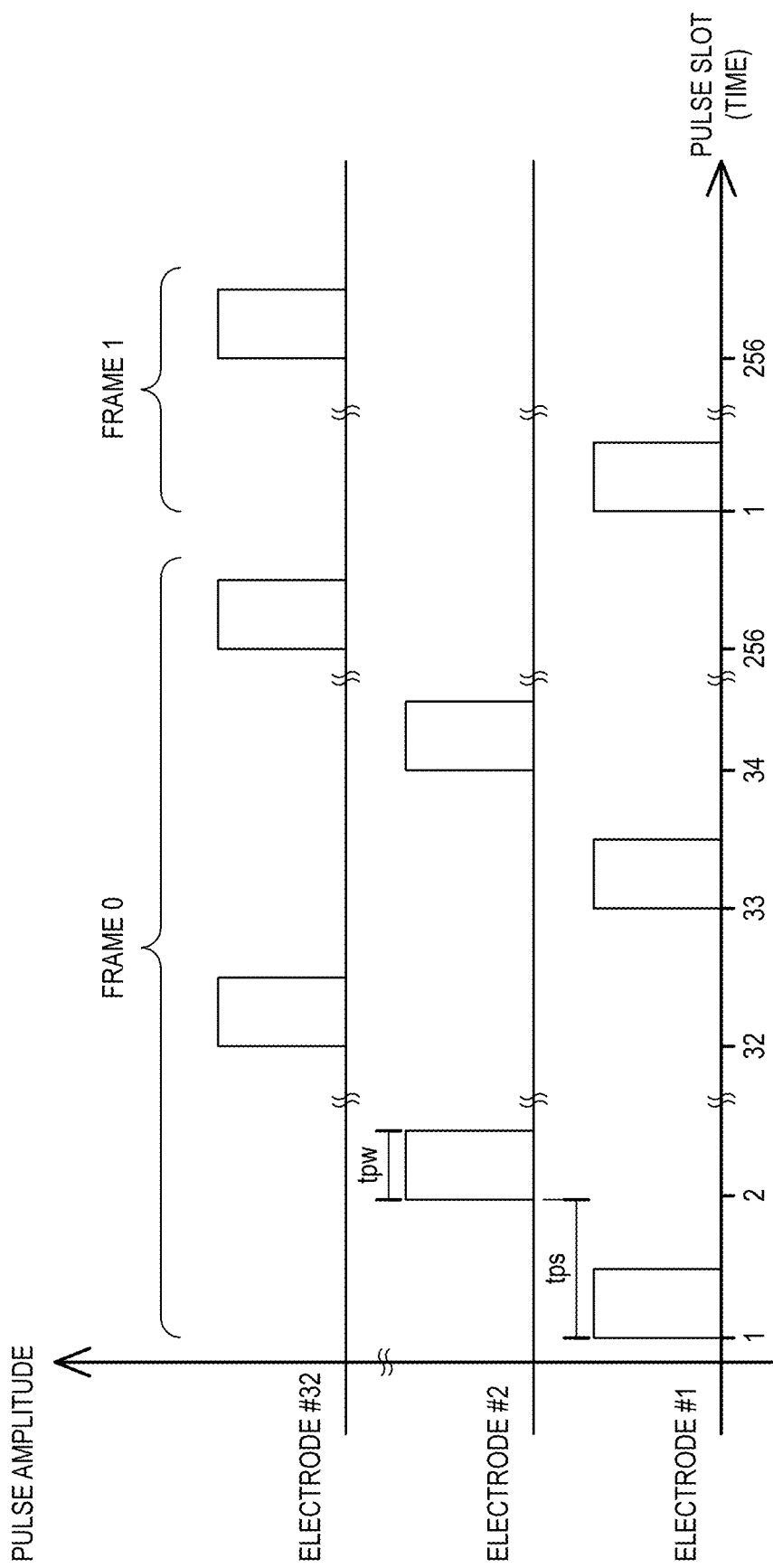
FIG. 6 is an overview of electro-tactile stimulus patterns in accordance with an aspect of the invention.

Based on the parameter values, the time pattern of the tactile pulses is generated. There are a total of 256 pulse slots per frame. Each electrode is assigned a subset of the available time slots as diagrammed in FIG. 6. This figure outlines the pattern of pulse slots for a single frame (frame 0), and a follow-on frame (frame 1).

The total number of slots that an electrode is set active in any given frame is determined by the amplitude of that frequency bin in the frame. For example, if the amplitude level is 2, then the first two slots for the electrode are set active and the remaining are kept de-activated. In the example shown in FIG. 6, there is 8 pulses for each of electrodes #1, #2 and #32 in Frame 0.

ETS Pulse Morphology

Figure 14:
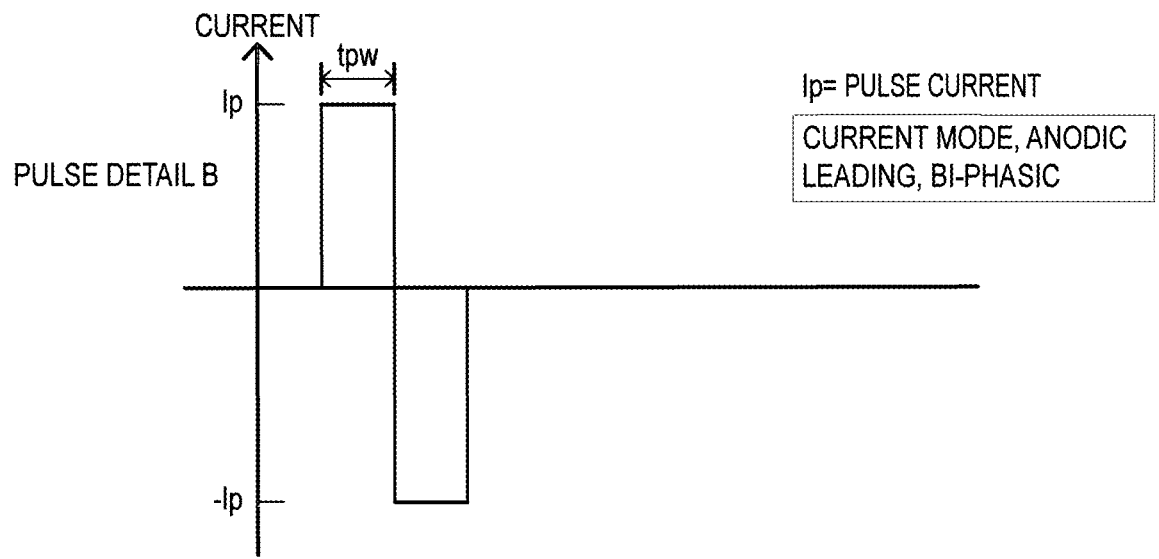

It will be appreciated that the MB1 and MB2 configurations use pseudo-biphasic, anodic (positive leading) pulses, as diagrammed in "Pulse Detail B" of FIG. 14.

Pseudo-biphasic pulses are generated using a rectangular wave voltage source, with a series capacitor to the active electrode. Because the net charge across the capacitor always sums to zero (an ideal capacitor has infinite impedance to direct current), the pulse is effectively bi-phasic. This results in minimal electrolysis products generated at the electrode/mucosal surface interfaces, thereby maintaining the integrity of the electrodes and minimizing the risk of sensitization or iteration to the patient.

Results of in-vivo experiments with anodic pulses demonstrated a significant reduction in the threshold of perception for anodic pulses rather than for cathodic pulses. Accordingly, anodic pulses are implemented in accordance with the embodiments described herein however it is not restricted as such.

ETS Pulse Mode Control

For electro-stimulation there are two principal methods of control, namely
Voltage mode control
Current mode control
The relative advantages and disadvantages of each are outlined in Table 9:

TABLE 9

| Stimulation Source Type | Advantages | Disadvantages |
| --- | --- | --- |
| Voltage sources | Low cost and complexity to implement<br>Less exposure to hazardous energy density in the event that the electrodes become partially disconnected | More difficult to control the injected charge, especially if the contact area and contact electrolytes have a tendency to vary over time |
| Current sources | High degree of control of the delivered charge | Potential for exposure to hazardous energy density in the event that the electrodes become partially disconnected, particularly for transcutaneous stimulation on dry skin using electrodes with large surface area.<br>High cost and complexity to implement |

Even though current mode control is preferable in many scenarios, it will be appreciated that due to the necessity for stimulating the mucosal surface of the tongue, voltage mode control is preferable for the following reasons:

Reduced risk of 'startle' hazards, for example in a scenario where the electrodes temporarily break contact from the mucosal surface, the voltage increases to compensate, and when the electrodes make contact again the higher voltage causes an initial 'shock' before the current-mode control loop re-stabilizes.

The availability of a constant electrolyte (saliva) results in a stable electrical interface, partially offsetting the need for current-mode control.

The cost and complexity of a 32-channel current mode control circuit would be significant compared to a voltage mode control circuit.

Current Mode Control of Stimulation Pulses

In the MB1 and MB2 configurations described herein the stimulation is assumed to be voltage-mode control, however, it will be appreciated that current mode control can also be used. Based on in-vivo tests, at 50 us pulse width, the voltage on a 47 nF series blocking capacitor dropped from increased from 0V to 1.35V on average across all users. The required current is therefore $I=CdV/T, dV\sim=1.35V*47$ nF/50 us=1.27 mA So, if constant current mode control is used instead of voltage mode control, then a constant current of 1.27 mA should be used, with the voltage limited to anywhere between 6V and 12V.

The range of charge delivered in this scenario will be from $Q(min)=I*Tmin=1.27$ mA*5 uS=6.35 nC to $Q(max)=I*Tmax=1.27$ mA*78 uS=99 nC A potential disadvantage with the audio to somatosensory mapping described above in relation to the configurations proposed for the MB2 and MB1 configuration is that there may be significant temporal smearing of auditory events when transformed into the somatosensory signals, particularly at higher frequencies, because:

The analysis windows are fixed at 23.2 ms, for all frequency bands

There is 50% overlap in the analysis windows (to cater for the application of window functions prior to computing the Fourier transforms)

The amplitude of the auditory events is mapped to a train of pulses rather than a single pulse, and therefore the somatosensory event that is derived from an auditory event can be spread over a period of up to 8 pulses at up to 2.9 ms inter-pulse interval (i.e. spread over a temporal window of duration up to 20.5 ms).

In practice, this results in correlates of high frequency auditory events being up to +/−11 ms shifted in time with respect to the first pulse of the corresponding somatosensory events, where the time shift has a truncated normal distribution.

An alternative transformation is outlined below, which breaks away from the temporal-frequency resolution trade-off limitations of standard Fourier analysis, by analyzing each frequency band at a rate that is commensurate with the center frequency of that band, i.e., by analyzing each frequency band at a different rate in order to reduce temporal smearing of the result.

Figure 19:
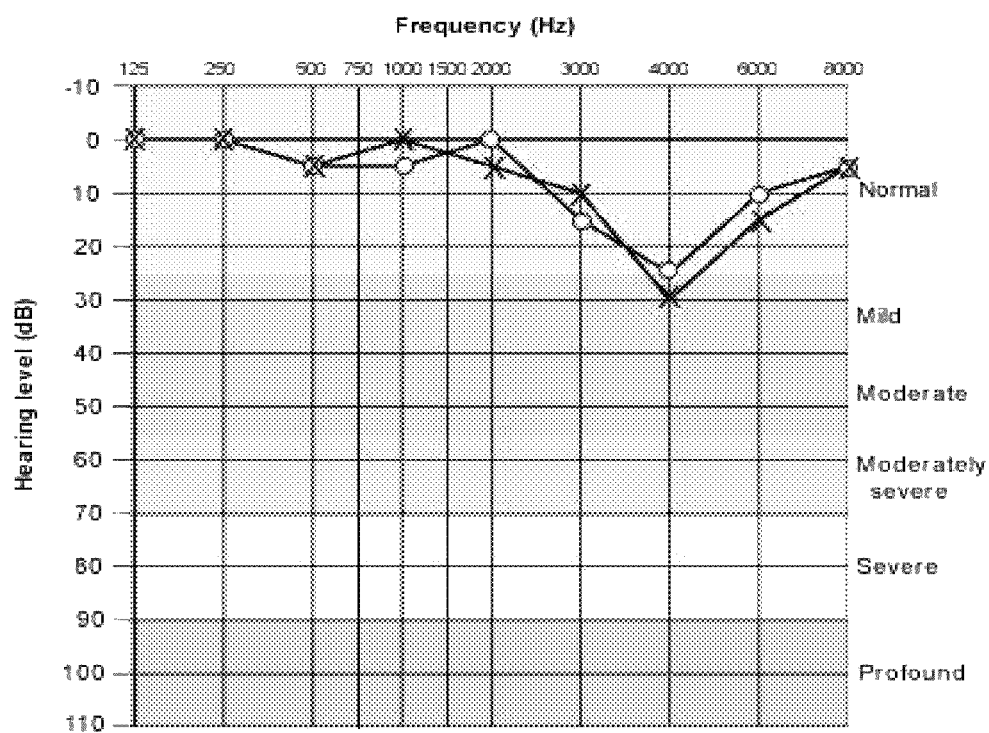
FIG. 19 is a sample audiogram in accordance with the patient of Example 1.

FIGS. 18 and 19 below shows the high level block schematic and timing waveforms of the alternative transformation.

The schematic shows just two of the n frequency channels of the transformation, and for one side of the split-array configuration only. In this regard, only the left audio channel is shown. The auditory stimulus component (including the mechanisms relating to the spectral modifications and amplitude adjustment) is not shown in this schematic, as it is the same for the MB1 and MB2 configurations detailed above.

The timing diagram indicates the typical timing for one of the n channels. Two analysis frames are shown as an example, the first frame indicates a scenario whereby there is sufficient energy in the relevant frequency band to cause a somatosensory pulse to be generated, whereas in the second frame there is insufficient energy and hence a somatosensory pulse is not generated.

The band pass filters are designed such that they have center frequencies and bandwidths as per the Bark scale critical bandwidths. A gammatone filter bank would be suitable in this regard, as the filter response closely matches the response of the basilar membrane in the cochlea.

The algorithm operates as follows:

The audio signal to be transformed is split into n different branches, one branch for each of the somatosensory channels (frequency bins).

The signal passes through a band-pass filter, with center frequencies' preferably at the Bark scale critical band center frequencies.

The signal is then rectified (i.e. the absolute value is computed).

The rectified signal is then integrated over a period, tf[x], in order to calculate the energy of the signal within that period.

The integral signal (Iout[x]) is compared to the threshold level, Threshold[x], in the comparator, where the output of the comparator transitions high once the integral signal magnitude is higher than the threshold value and vice versa.

A D-type flip-flop is used to generate the somatosensory pulse based on the comparator output (Cout[x]) and two pulse slot timing signals, PulseSet[x] and PulseReset[x], where a pulse is generated with the appropriate pulse width if, and only if, the comparator output is high at the instant in time when the pulse slot starts (i.e. at the instant in time when the PulseSet[x] signal transitions high).

The timing signals, IntReset[x], PulseSet[x] and PulseReset[x] are arranged such that There is no overlap in pulse slots associated with electrodes that are topographically adjacent to each other (this is to assure that every pulse presented to an electrode has all adjacent electrodes to said electrode available as the current return path).

In one version of this implementation there is never any overlap in pulse slots (as is the case for the MB1 and MB2), in which case all but one of the electrodes can take the role of the return current paths.

In another version of this implementation, there is overlap in pulse slots but only with respect to pulses that are destined for electrodes that are not topographically adjacent to each other. In practice, a maximum of 2 to 4 simultaneous pulses can be supported without violating this non-adjacent requirement.

The analysis period (frame period $t_{f[x]}$) must be greater than the somatosensory refractory period (which may be of the order of 1 ms to 2.5 ms, the actual value must be elucidated by in-vivo experiments). This is to avoid the possibility of subsequent pulses occurring before the target nerve fibers have repolarized following the previous pulse.

The analysis period (frame period $t_{f[x]}$) should also be greater than the impulse response of the auditory filters. For example, if using gammatone filters, the impulse response can be represented in about 10 cycles of the filter center frequency and therefore the analysis period should be greater than this.

The analysis period (frame period $t_{f[x]}$) should also not be substantially greater than the impulse response of the auditory filters, as this will unnecessarily sacrifice temporal resolution of the transformation. For the higher frequency bands however it is expected that the refractory period will be the limiting factor in relation to this.

To maximize the period of integration within a given analysis window, the PulseSet[x] signal should occur as close to the end of the analysis window as possible (e.g., still leaving enough time for the pulse Q[x] to complete before the next analysis window starts, although it is also feasible for the pulse to continue into the next analysis window period).

The analysis windows can be temporally consecutive, or they can overlap. For the lower frequency bands where the analysis period, $t_{f[x]}$, is greater than twice the refractory period it is preferable that the windows overlap, as this improves the temporal resolution in these bands. At the higher frequency bands were the analysis period is less than twice the refractory period it is preferable that the analysis windows are temporally consecutive. The timing diagram below only shows an example where the analysis windows are temporally consecutive.

The global delay between the auditory and somatosensory stimuli can be configured by setting a delay on the audio signal to the patient (if it is required that the somatosensory stimulus leads the auditory stimulus), or by including a delay line in the somatosensory signal lines (Q[x]) if it is required that the auditory stimulus leads the somatosensory stimulus.

The transformation can be implemented in either the analog or the digital domains, since there are no elements of the system that requires a digital signal processor. However, it will be appreciated that in order to reduce the associated electronics cost, it would be preferable to implement the transformation in the digital domain.

The timing signals, IntReset[x], PulseSet[x] and PulseReset[x], where x∈{0:n−1} must be generated with low jitter, and as such this implementation is more amenable to a digital implementation.

It is possible that this transformation is performed either offline, as would be the case in the MB2 configuration, or online. The advantage of the former is that the implementation is lower power, and will extend the battery life in portable embodiments of the system. The MB2 configuration of the system can be programmed to implement this transformation by software changes alone.

In an exemplary arrangement of this alternative configuration, the optimum analysis window lengths for each listed frequency bin (filter) while meeting the constraints outlined above is shown in Table 10. In this example:

- The repolarizing period is assumed to be 2.5 ms, and so the resulting transformation will not output a subsequent pulse on the same electrode until this time has elapsed.
- The filters chosen are gammatone filters, with center frequencies the same as the Bark scale critical bands as utilized in the MB2 split-array configuration. In this case, the gammatone filters are truncated to a length of 10 periods of the relevant filter center frequency.
- The analysis window length varies according to the filter frequency, however they are set to integer multiples of the minimum repolarization period. This is to ensure that the temporal arrangement of the pulses can be such that the pulse overlapping requirements are met (see above).
- The analysis window shift (i.e., the period that the analysis window shifts for each analysis step) is set such that it is greater than or equal to the refractory period, and greater than 2.5 periods of the filter center frequency.

As can be seen in this example, the temporal resolution of the transformation increases as the audio frequency increases. The temporal resolution is limited only by the minimum repolarization period for the somatosensory modality being utilized, or for the lower frequencies by the length of the impulse response of the filter. In certain circumstances, this repolarization period may be 1 ms or lower, which would facilitate even higher temporal resolution for the higher frequency bands than that achieved in the above example.

TABLE 10

| Channel number | Filter center freq. [Hz] | Filter Center Freq. Period [ms] | Gammatone filter period (10x center frequency period) [ms] | Analysis window length tf[x] [ms] | Refractory period [ms] | Analysis Window Shift Step [ms] | Max # pulses per second |
|---|---|---|---|---|---|---|---|
| 1 | 570 | 1.75 | 17.54 | 20.0 | 2.5 | 5.0 | 200 |
| 2 | 700 | 1.43 | 14.29 | 15.0 | 2.5 | 5.0 | 200 |
| 3 | 840 | 1.19 | 11.90 | 15.0 | 2.5 | 5.0 | 200 |
| 4 | 1000 | 1.00 | 10.00 | 10.0 | 2.5 | 5.0 | 200 |
| 5 | 1170 | 0.85 | 8.55 | 10.0 | 2.5 | 2.5 | 400 |
| 6 | 1370 | 0.73 | 7.30 | 7.5 | 2.5 | 2.5 | 400 |
| 7 | 1600 | 0.63 | 6.25 | 7.5 | 2.5 | 2.5 | 400 |
| 8 | 1850 | 0.54 | 5.41 | 7.5 | 2.5 | 2.5 | 400 |
| 9 | 2150 | 0.47 | 4.65 | 5.0 | 2.5 | 2.5 | 400 |
| 10 | 2500 | 0.40 | 4.00 | 5.0 | 2.5 | 2.5 | 400 |
| 11 | 2900 | 0.34 | 3.45 | 5.0 | 2.5 | 2.5 | 400 |
| 12 | 3400 | 0.29 | 2.94 | 5.0 | 2.5 | 2.5 | 400 |
| 13 | 4000 | 0.25 | 2.50 | 2.5 | 2.5 | 2.5 | 400 |
| 14 | 4800 | 0.21 | 2.08 | 2.5 | 2.5 | 2.5 | 400 |

TABLE 10-continued

| Channel number | Filter center freq. [Hz] | Filter Center Freq. Period [ms] | Gammatone filter period (10x center frequency period) [ms] | Analysis window length tf[x] [ms] | Refractory period [ms] | Analysis Window Shift Step [ms] | Max # pulses per second |
|---|---|---|---|---|---|---|---|
| 15 | 5800 | 0.17 | 1.72 | 2.5 | 2.5 | 2.5 | 400 |
| 16 | 7000 | 0.14 | 1.43 | 2.5 | 2.5 | 2.5 | 400 |

System Overview

Figure 7:
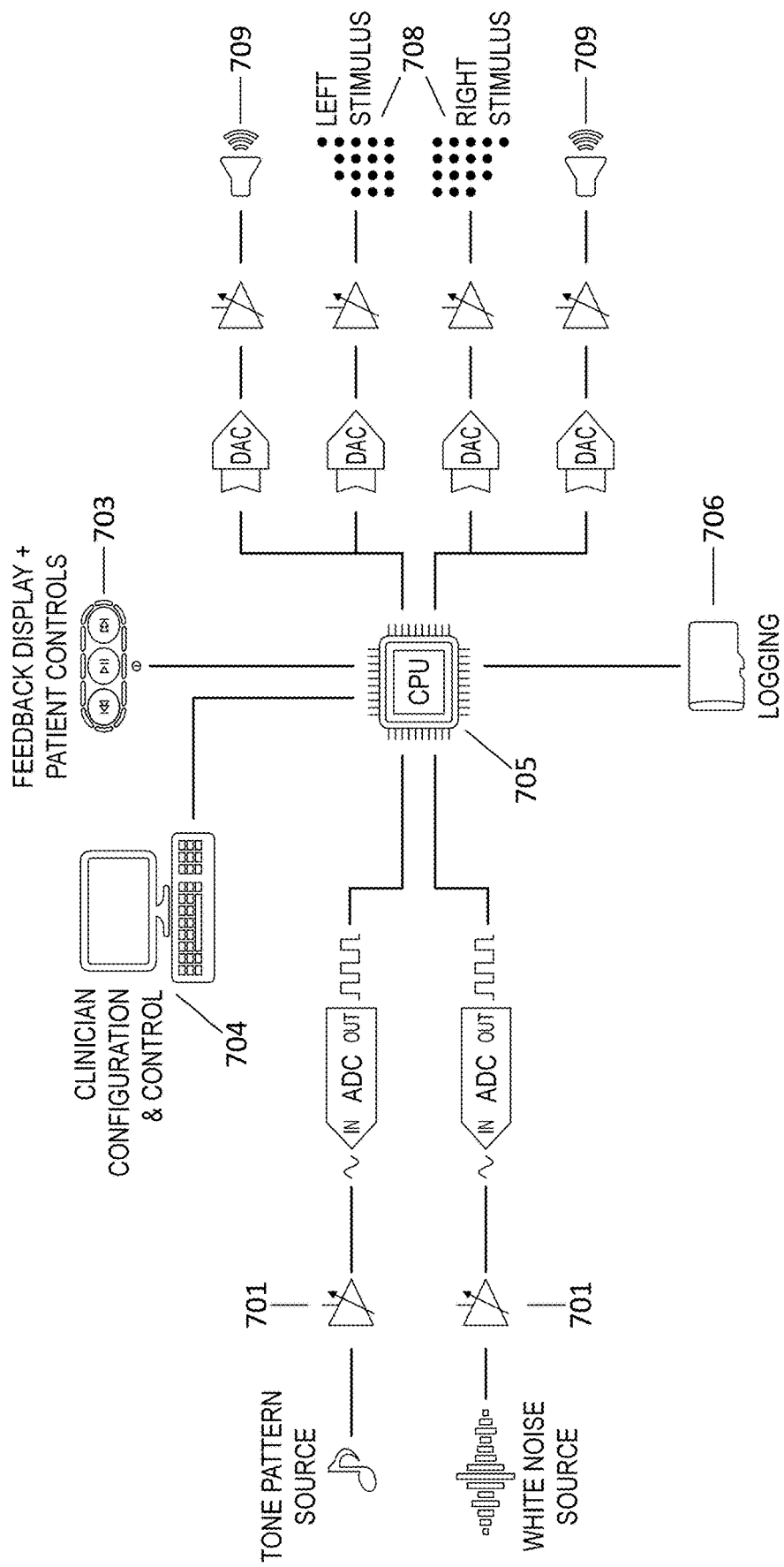
FIG. 7 is a sample diagram of a microcontroller implemented system in accordance with an embodiment of the invention.
Figure 8:
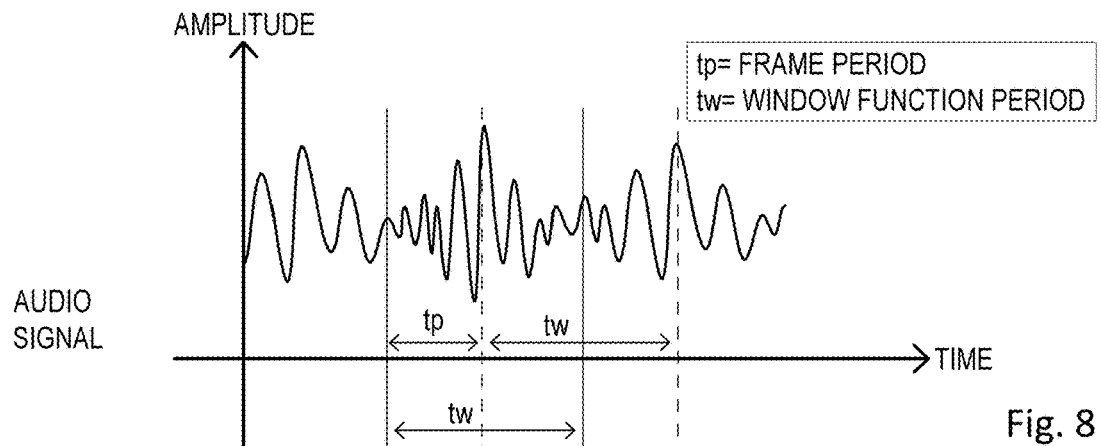
FIGS. 8 to 14 illustrate the transformation between audio and somatosensory stimulation and illustrate how one of the binaural channels is transformed for use in a split-array stimulator topology in accordance with an embodiment of the present invention.
Figure 9:
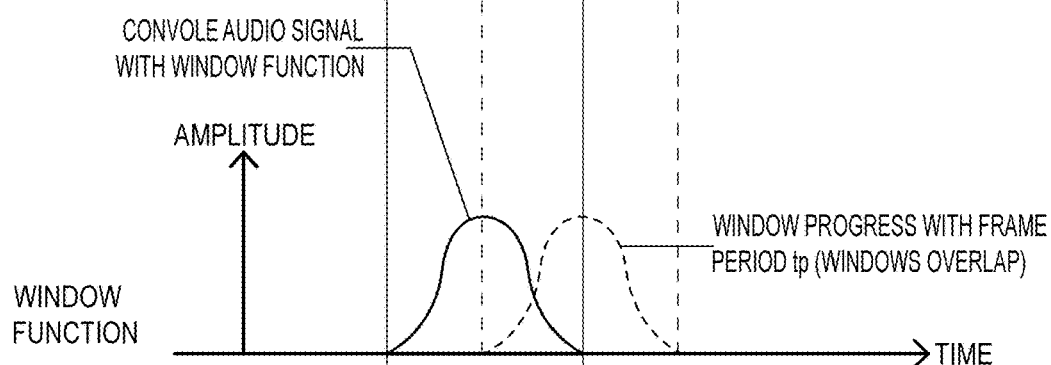
Figure 10:
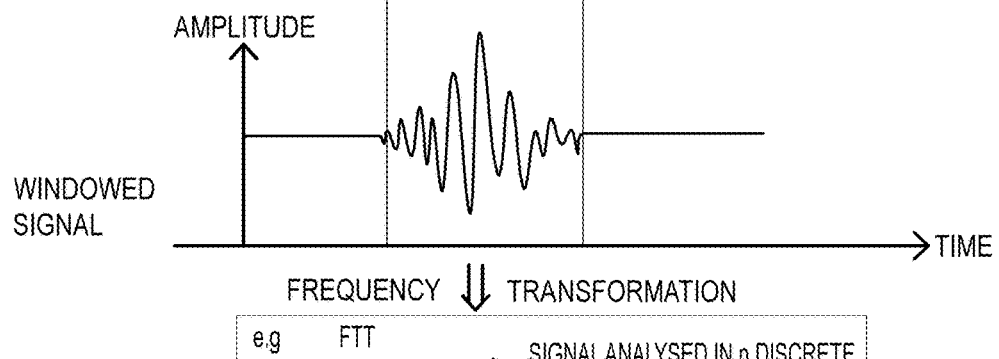
Figure 11:
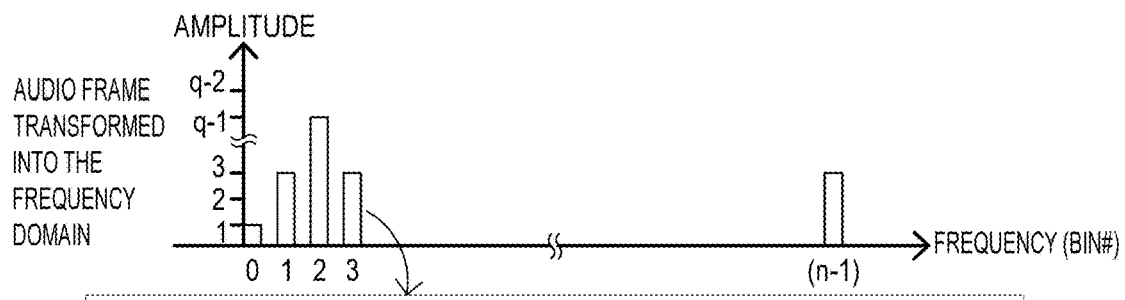
Figure 12:
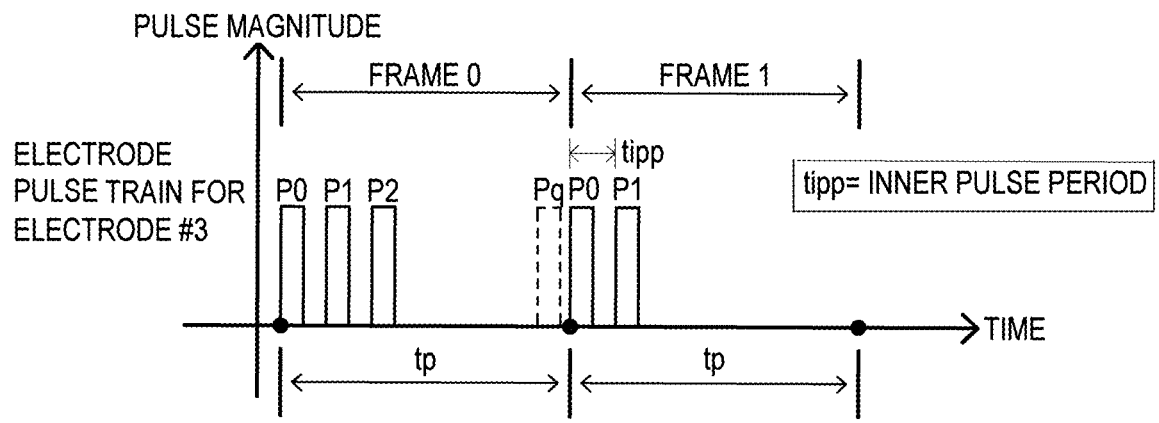
Figure 13:
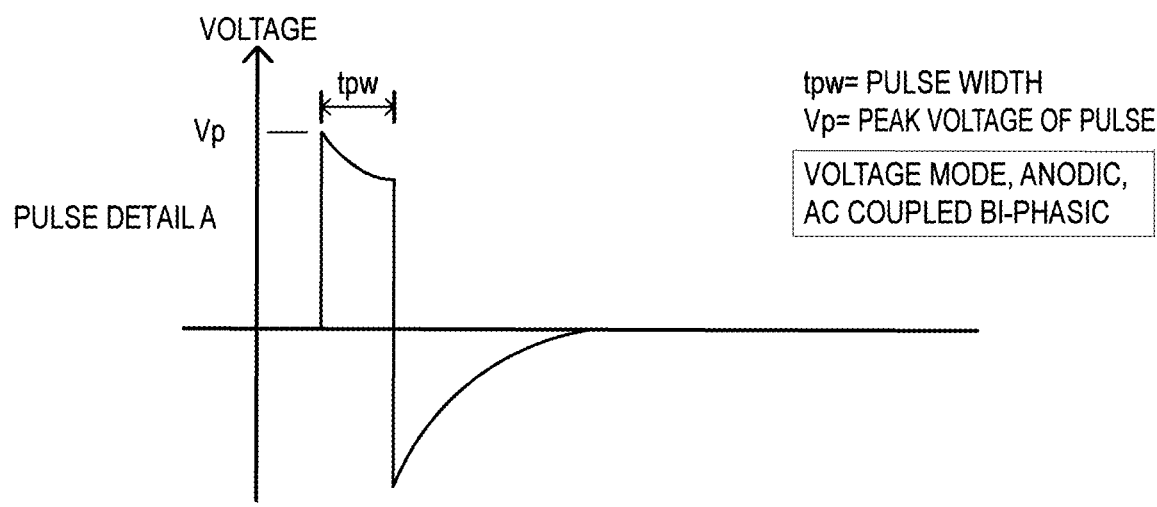

An overview of a system in accordance with the invention is shown in FIG. 7. The dual audio inputs as described above sampled by the central processing unit, CPU, 705, wherein said audio inputs can be mixed digitally and further spectrally modified for output to the auditory stimulation unit, and one or more of the audio inputs are transformed to the somatosensory stimuli as described above. It will be appreciated that this CPU may be any computing device such as an embedded microcontroller, an FPGA, a personal computing device (phone, tablet, PC, etc.). Once the transformation is complete, the resulting data can be stored to the local memory, for example the micro SD card, 706, to save energy of having to re-transform the audio for subsequent treatment sessions. It will be appreciated that other memory devices may be used. The CPU transforms the audio into the required somatosensory stimulus, and displays this stimulus on the somatosensory stimulus arrays 708 in substantially synchronous with the audio, 709, which is delivered through a set of headphones (though bone conduction transducer, loudspeakers, hearing aids or cochlear implants or other audio transducers can also be used as described above). Key parameters relating to the delivery of the stimulus to the patient are recorded to file and stored on the memory, such as the card 706. These parameters include, but are not limited to, the following:

Duration of use
Time and date of use
Identification data (hardware serial number, software versions) for tracing results to unique patients
Stimulus parameters
Energy measurement of stimulation
Audio stimulation level settings
Somatosensory stimulation level settings
Audio track selection (for multi-track systems)

Also provided is a user interface for providing feedback to the patient, 704, such as a keyboard, touch screen interface, mobile computing device interface, computer application or the like which would facilitate a clinician interacting with the system so as to configure key parameters, such as:

Filter settings, as per the patients audiogram or tinnitus match frequency
Audio volume pan control, as per the patient's audiogram.

In addition to this clinician interface, a patient interface 703, is also provided to allow the patient to adjust the stimulus levels and the start and end of the treatment sessions. Events such as low power or low battery may also be reported to the patient. Again this may be any visual or haptic display and may include visual display units, mobile computing devices and applications run thereon or the like.

In the systems described herein the electrode device circuit may be located remote from or local to the Intra-Oral device as outlined in the MB2 and MB1 configurations described above. The principle change in migration between MB1 and MB2 is that a global stimulus level control is preferably controlled by varying the pulse width of the stimulus in the MB2 configuration versus varying the pulse peak voltage level in the MB1 configuration. In the MB2 configuration, the drive voltage may also be lower than that in the MB1 configuration. For example, in the local or MB2 configuration the drive voltage level may be fixed at between 4.2V and 5.8V, whereas in a remote or MB1 configuration the drive voltage may be adjustable from 3V to 11V. This requires that the range of pulse widths in the local implementation will have to be increased to compensate for the change in range of the stimulus voltage.

It will be appreciated that the MB2 configuration wherein the control is located local to the stimulator array provides an efficient hardware design it is further reliable. For example, in such a configuration it is possible to use a 4 pole connector (e.g., a micro-USB connector) to connect to the signal processing controller rather than a 32-pole connector where the stimuli are generated remote from the array. Low cost microcontrollers can also be used to avoid the expense and complexity required of the high voltage drive circuitry in a remote configuration.

It will be appreciated that in any configuration, the stimulus generation unit, the auditory stimulation unit and the stimulus array can communicate wirelessly with each other rather than by wired connections. In the MB1 configuration, all components are wired together, in the MB2 configuration the auditory stimulation device communicates wirelessly with the stimulus generation unit.

Additional Embodiments

The embodiments described above incorporate a device, for the treatment of tinnitus and/or hyperacusis, misophonia, phonophobia where:

Auditory stimulus is given to the patient
  Audio composition
    Simplex tone bursts of periods between 2 ms and 500 ms across critical bands from between 500 Hz and 16 kHz, and repeated pseudo-randomly or as complex patterns (this could, for example, be monophonic music)
    Preferably complex tone bursts of periods between 2 ms and 500 ms across critical bands from between 500 Hz and 16 kHz, and repeated pseudo-randomly or as complex patterns (this could, for example, be polyphonic music)
    More preferably a broadband noise signal
    More preferably said broadband noise including a mixture of speech, to further improve attention to the stimulus during treatment and enhance compliance, where said speech is a topic of interest to the patient
    Documentary podcasts
    Audio-magazines
    Fiction or non-fiction audio books Even more preferable a mix of broadband noise and complex tone bursts (or music)
Of composition such that the same stimulus segment is not repeated within a particular timeframe
  Repeated no more than once per month
  Preferably repeated no more than once every 6 months
Of composition such that the music or speech component can be selected by the patient, and in one embodiment said music can be streamed from their own music playback device (e.g. phone, laptop, tablet computer)
Of composition such that it instils a sense of calm into the patient (to promote relaxation).
Of an amplitude (volume) that
  Is set to a comfortable level by the patient
  Preferably set to a level that does not over-mask the patient's tinnitus, where the patient's maskability level is determined by a Minimum Masking Level (MML) or Tinnitus Loudness Matching (TLM) audiological assessment
  Most preferably is set to a level where their tinnitus is still marginally audible.
With amplitude (volume) modulation that
  Ramps up to nominal amplitude within 5 to 10 seconds and then is constant throughout the remainder of the treatment session
  As above, but also ramps down (decrescendo) the amplitude from the nominal level to a level commensurate with the subject's hearing level for between 2 minutes and 5 minutes before the treatment session finishes
Is spectrally modified
  Set with a band boost filter
    Of center frequency set to the subject's tinnitus match frequency OR that matches the steepest roll-off of the patient's audiogram
    With half-power bandwidth of between 0.5 and 1.5 octaves normalized to the center frequency
    With boost magnitude of at least 12 dB
  Set with a plurality of band notch filters
    One notch filter of center frequency set to the subject's tinnitus match frequency, and with a half-power bandwidth between 0.25 and 1 octave normalized to the center frequency, and with a notch depth of at least 36 dB.
    Two notch filters with depth of 36 dB and with half-power bandwidth between 0.25 and 1 octave, centered between 0.5 and 1.5 octave above and below the tinnitus match frequency.
  To compensate for the deficit in the patient's audiogram (i.e., an inverse audiogram response)
Has audio channels
  Single channel (monoaural) stimulus delivered to both ears
  Preferably dual channels (binaural) delivered to both ears
  Most preferably dual channels (binaural) with each channel additionally modified both in amplitude and spectrally to match the audio profile of the ipsilateral ear, where said modification in amplitude is dynamically adjusted to track the patient's tinnitus loudness (MML)
Is delivered (transduced) by
  Bone conduction transducers
  Cochlear implants
  Loudspeakers located within the same space as the patient
    Sound from ultrasound technology https://en.wikipedia.org/wiki/Sound_from_ultrasound
  Preferably by in-ear audio transducers
    In-ear phones
    Hearing aids
  Most-preferably by over-ear audio transducers (headphones)
AND/OR
Somatosensory stimulus given to the patient,
  Stimulus delivered as plurality of parallel channels:
    Therapeutic stimulus
      At least one stimulation channel/site and up to 64 channels/sites
      Preferably between at least 4 and 32 stimulation channels/sites
      Most preferably at least 16 stimulation channels/sites
    Indicator stimulus
      Additional stimulus channels that are designed to provide a sensation of an effect to the patient, but are not part of the therapeutic stimulus:
      Purpose:
        In cases where the primary stimulus channels deliver a somatosensory stimulus that is not perceptible, or weakly perceptible to the patient (e.g., the optimum stimulus amplitude is below the threshold of perception of the subject, but it is essential that the patient is aware that the stimulation is active so that they are more likely to comply with the treatment regimen)
        To facilitate conducting clinical investigations where a sham-treatment arm is required (e.g., for a double blinded RCT)
      Number of channels:
        At least one pseudo-stimulus channel
        Preferably at least two pseudo-stimulus channels (for bilateral stimulation) so that they can be arrange symmetrically with respect to the stimulator array OR
        Time multiplexing the pseudo stimulus with the treatment stimulus, such that the pseudo stimulus can be delivered via the treatment stimulus electrodes, with the pseudo to treatment stimulus mark:space ratio no more than 10%.
      Stimulation Properties:
        Stimulation to be asynchronous to any auditory stimulus
        Stimulation to have a low duty cycle relative to the therapeutic stimulus
        Stimulation to be blocking in nature, i.e. the stimulation comprises a periodic pulse train of period less than the relevant nerve fiber repolarization period, thereby maintaining the nerve fiber in a constant state of depolarization, which usually elicits at tingling (paraesthesia) sensation in the subject, and with said stimulus not synchronized in any way to the audio stimulus.

Stimulus type is any of:
  Random stimulation
    Inter-pulse period ($t_{ipp}$):
      randomized to between 5 ms and 105 ms (Gaussian distribution, mean inter-pulse period 55 ms) OR
      Preferably randomized to between 5 ms and 55 ms (Gaussian distribution, mean inter-pulse period 30 ms) OR
      Most preferably randomized to between 5 ms and 25 ms (Gaussian distribution, mean inter-pulse period 15 ms)
    Channel synchronicity/asynchronicity
      All stimulus channels acting as independent actuators and displaying independent randomized patterns
      All stimulus channels displaying the same random pulse pattern
      Preferably all stimulus channels displaying unique random patterns
    Duty cycle:
      Stimulus always active during the treatment session
      Stimulus delivered in bursts during the treatment session to reduce habituation and increase patient awareness and attentiveness
      Mark-space of 1 second to 1 second
      Preferably mark-space of 1 second to 0.1 second
      Most preferably mark-space of 5 second to 0.5 second
      Even more preferably with a mark-space values that vary randomly (mark varying in the range 0.5s to 5s, space varying in the range 0.1s to 1s) over the course of the treatment
  Periodic patterned (deterministic) stimulation
    Inter-pulse period ($t_{ipp}$):
      of between 1 ms and 20 ms
      Preferably of between 2 ms and 3 ms for over-stimulation (blocking) or between 15 ms and 20 ms for non-blocking stimulation
    Burst pattern
      At least 4 pulses per frame, number of pulses varying as a pattern with mean of 2 pulses per frame
      Preferably at most 8 pulses per frame, number of pulses varying as a pattern with mean of 4 pulses per frame
    Frame rate
      of between 20 and 100 frames per second
      preferably 43 frames per second
  Most preferably synchronous stimulation (synchronized to the audio stimulus)
    Where the audio input to the transformation to somatosensory is
      one or more of the components of the audio stimulus delivered to the subject, for example the complex tone burst pattern component or the music component OR
      the audio stimulus delivered to the subject pre-spectral modification OR
      Preferably the audio stimulus delivered to the patient post-spectral modification
    With audio to tactile delay
      Fixed delay between audio and somatosensory (up to +/−50 ms)
      Random variation in delay between audio and somatosensory (with rectangular probability density function with limits up to +/−50 ms, or with Gaussian probability density function of standard deviation up to 20 ms), to cover a wide range of latencies over the course of a treatment session
      Fixed delay, where the delay is different for each of the stimulus channels (in the multi-frequency embodiment), with a delay variable between −500 and +500 ms, so as to selectively inhibit or enhance activity in the desired frequency bands.
  With number of somatosensory stimulation channels (stimulation electrodes)
    At least one stimulation channel
    Preferably at least 8 channels to cover Bark scale critical bands from 2 kHz to 8 kHz
    More preferably at least 16 stimulation channels per side (to cover Bark scale critical bands from 500 Hz to 8 kHz or Bark Scale critical bands from 1 kHz to
    Most preferably at least 24 stimulation channels per side (to cover Bark scale critical bands from 60 Hz to 13.5 kHz)
    Alternatively with a small number of channels (between 4 and 8) such that the channels cover critical bands that
      Correspond to the frequency regions where the tinnitus is dominant AND/OR
      Correspond to the frequency regions of highest hearing loss in the patient (within the range 250 Hz to 13.5 kHz)
  With transformation between audio and tactile
    Somatosensory pulses occur when audio amplitude rises above a predetermined fraction of the normalized peak amplitude (single channel) wherein said predetermined fraction is between 0.05 and 0.95
    Preferably somatosensory pulses occur when the amplitude within each critical band rises above a predetermined fraction of the normalized peak amplitude within the same critical band (for multi-channel stimulation) wherein said predetermined fraction is between 0.05 and 0.95
    Most preferably a number of tactile pulses occur in proportion to the amplitude within each critical band (for multi-channel stimulation)
    where the analysis window has a period (frame period, $t_p$)
      Fixed frame period
        Audio signal is analyzed in overlapping (by between 10% and 50%) frames of between 2 ms and 100 ms duration (preferably 23.2 ms), where the frame period is the same for all frequency bins
        2 ms is the lower limit as frequencies below 500 Hz cannot be analyzed for shorter audio frames
        100 ms is the upper limit, such that there would be a maximum of +/−50 ms of temporal smearing of the tactile stimulus relative to the audio stimulus
      Variable frame period
        Audio signal is analyzed in overlapping frame periods where said frame periods are different for each frequency bin, such that the transformation to the frequency domain retains high temporal resolution
  Frame period set to no more than 20 periods of the corresponding frequency bin
  Preferably the frame period set to no more than 10 periods of the corresponding frequency bin
  Most preferably the frame period set to no more than 4 periods of the corresponding frequency bin
  Amplitude binning is at least 8 discrete levels
Stimulus site is
  Trans-cutaneous
    Cheek (maxillary branch of trigeminal nerve)
    Jaw (mandibular branch of trigeminal nerve)
    Forehead (ophthalmic branch of trigeminal nerve)
    Neck (sub-mandibular branch of trigeminal nerve)
    Ear/Pinna (vagus nerve)
    Lips (mandibular branch of trigeminal nerve)
    Shoulders and Neck (Accessory Nerve, cervical spine nerves C1 and C2)
  Trans-mucosal
    Dorsal-anterior region of the tongue (lingual mandibular branch of trigeminal nerve)
    Ventral-anterior region of the tongue (hypoglossal nerve)
    Gums (maxillary branch of trigeminal nerve)
  Non-contact (Electro-magnetic only, e.g., rTMS)
    As above (both trans-cutaneous and trans-mucosal sites) OR
    Trigeminal nuclei
    Cochlear nuclei
    Auditory cortex
  Implantable
    As above (both trans-cutaneous and trans-mucosal sites) OR
    Cochlear/auditory nerve
    Cochlear nuclei
    Trigeminal nuclei
    Auditory cortex
    Vagus nerve
Stimulus modality is
  Electrical
    Of pulse type
      Anodic—AC coupled
      More preferably Cathodic—AC coupled
      Even more preferably bi-Phasic, Anodic leading
      Most preferably bi-Phasic, Cathodic leading
    Of pulse energy
      For tongue mucosa (dorsal anterior region)
      For voltage mode control (AC or DC coupled)
      Adjustable between 50 Volt-microseconds and 500 Volt-microseconds
      Preferably adjustable between 15 Volt-microseconds and 1000 Volt-microseconds
      For current mode control (AC or DC coupled)
      Adjustable between 10 nC (nano-Coloumbs) to 100 nC
      Preferably Adjustable between 5 nC (nano-Coloumbs) to 200 nC
      AND with voltage limiting of between 4V and 12V
      Pulse width adjustable between 3 us and 78 us
      For trans-cutaneous mandibular trans-cutaneous stimulation
      For voltage mode control (AC or DC coupled)
      Adjustable between 500 Volt-microseconds and 5000 Volt-microseconds
      Preferably adjustable between 100 Volt-microseconds and 10000 Volt-microseconds
      For current mode control (AC or DC coupled)
      Adjustable between 100 nC (nano-Coloumbs) to 1000 nC
      Preferably Adjustable between 50 nC (nano-Coloumbs) to 2500 nC
      AND with voltage limiting of between 40V and 80V
      Pulse width adjustable between 10 us and 250u
    Contact Area
      Tongue mucosa
      At least 0.5 mm$^2$
      Preferably at least 1 mm$^2$
      Transcutaneous (Mandibular region)
      At least 5 mm$^2$
      Preferably at least 10 mm$^2$
    Spatial Arrangement—Array Topology
      Centered (for random stimulation, or for in conjunction with single channel and monaural audio)
      Preferably split along medial line with ipsilateral mapping of auditory to tactile (for synchronous-with-audio stimulation)
      (for tongue mucosa) Most preferably split along medial line with ipsilateral mapping of auditory to tactile but with a dead band along the medial line to reduce the need for exact centering of array on tongue—two symmetrical sides of the array should be physically separated by a gap, where the width of the gap is determined by a function of tongue mechanoreceptor density (which is in the tongue is in the order of 1 neuron per 0.5-1 mm) and stimulation spread of twice the inter-electrode spacing to avoid somatic side channel recruitment of parallel fibers.
      A tactile feature, such as a groove or ridge, can be situated along this medial line to aid the patient to center the device on their tongue
    Spatial Arrangement—Individual Stimulator Channels
      The Euclidian distance of adjacent stimulator elements shall be at least the distance of the JND of tactile perception in adult population at the site of stimulator contact, which is approx. 0.5-1 mm)
      Preferably the Euclidian distance of adjacent stimulator elements shall be at least the 1.5 times the distance of the JND of tactile perception in adult population at the site of stimulator contact"
    Spatial Arrangement—Array element arrangement
      Random arrangement of array elements
      More preferably arranged in raster pattern, in order from lowest frequency bin to highest frequency bin
  Preferably arranged in spiral pattern, from lowest frequency bin on the inside to highest frequency bin on the outside, akin to the tonotopical mapping in the cochlea
    Most preferably arranged such that the frequency bins of highest deficit are situated at locations of highest sensitivity.

Mechanical
  Vibration
    Vibration frequency
      Between 10 Hz and 500 Hz
      Preferably between 50 Hz and 150 Hz
      Most preferably 125 Hz
    Vibration Amplitude
      Amplitude variable such that there are amplitude bins equally spaced between the threshold of perception and 50% of the threshold of discomfort
    Vibration Amplitude Modulation
      Amplitude varied over at least the number of amplitude bins, at the system frame rate
    Contact Area
      Tongue mucosa
        At least 0.5 mm$^2$
        Preferably at least 1 mm$^2$
      Transcutaneous (Mandibular region)
        At least 5 mm$^2$
        Preferably at least 10 mm$^2$
    Spatial arrangement (as per Electrical spatial arrangement sections below)
  Force (pressure)
    As per Vibration, except
    No vibration component
    Force amplitude levels to be calibrated per subject
    Force amplitude modulation to be calibrated per subject
  Electro-Magnetic (trans-cutaneous and/or transcranial magnetic stimulation)
    Magnetic field strength 1 mT to 10 mT
    Magnetic field pulse duration 10 us to 100 us
    Pulse period 10 ms to 200 ms (non-synchronous with audio)
    Synchronous with audio (Tactile pulses occur when audio amplitude rises above a predetermined fraction of the normalized peak amplitude (single channel)) wherein said predetermined fraction is between 0.05 and 0.95
    Stimulation site
      Mastoids
      Mandibular nerve sites
      Maxillary nerve sites
      Opthalmic nerve sites
  Stimulus symmetry is
    Symmetrical (same stimulus is imparted to both sides)
    Preferably asymmetrical (stimulus is imparted to match the audio on the ipsilateral side)
  Stimulus duration is
    Between 5 minutes and 240 minutes per day
    Preferably between 15 minutes and 60 minutes per day
    Most preferably at least 20 minutes per day
  Treatment duration is
    Every day for at least 4 weeks
    Preferably every day for at least 10 weeks
    Most preferably every day for at least 6 months
And also in connection with
A system for recording the parameters of, and measurement during treatment including
  Duration of use
  Time and date of use
  Identification data (hardware serial number, software versions) for tracing results to unique patients
  Stimulus parameters/measurements
    Audio stimulation level settings
    Somatosensory stimulation level settings
    Audio track selection (for multi-track systems)
  Audio parameters/measurements
    Audio filtering (spectral modifications)

Example 1

In a first example, the patient presents with a suspected hearing loss and/or tinnitus, and pure tone audiometry is carried out to quantify the type, degree and configuration of hearing (as described above). Psychoacoustic assessment, including Tinnitus Matching (TM), Tinnitus Loudness Matching (TLM) and Minimum Masking Levels (MML) are determined (as described above).

The results of the audiogram for the patient can be seen in FIG. 19 (x=left ear, o=right ear), illustrating bilateral noise induced sensorineural hearing loss displaying a rather simple hearing loss profile. The right ear demonstrates a 25 dB loss at 4 kHz, and the left demonstrates a 30 dB loss at 4 kHz. The results of the psychoacoustic assessment of the patient for tinnitus (not shown in FIG. 19) results in tinnitus matched at a pure tone of 20 dB @ 4 kHz for the left ear and no tinnitus for the right ear.

Figure 20:
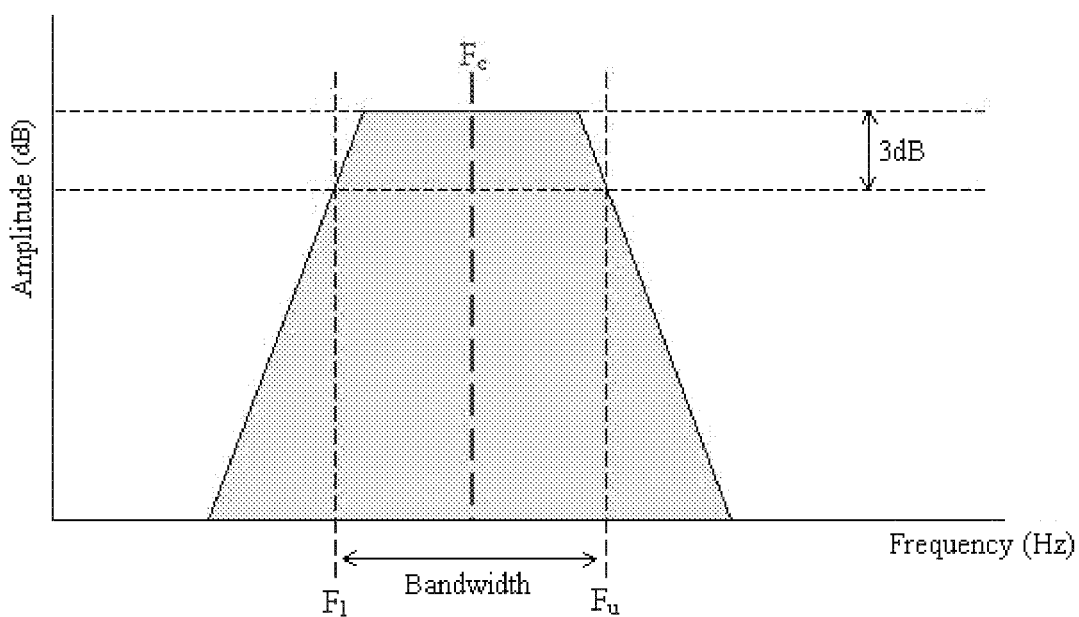
FIG. 20 is an illustrative example of a band boost band boost filter produced in accordance with one embodiment of the invention.

In accordance with an embodiment of the invention, a band boost filter is calibrated to boost certain frequencies (as exemplified in FIG. 20) based on the above hearing loss and tinnitus assessment and applied to an audio signal that is in turn then delivered to the ear. As each ear may have a different hearing loss profile, a different customized signal may be generated for each ear. In this example, a customized signal is only generated for the left ear because no tinnitus has been diagnosed for the right ear. Based on the audiogram, the boost ratio and center frequency (Fc) may be calculated, and these may be used in the design of the band boost filter. In this example, the boost ratio is set in order to boost by +25 dB, the center frequency (Fc) identified as 4 kHz (which in this case is also the tinnitus matching frequency). The bandwidth for the filter is determined as one octave up and down from the center frequency—in this case the bandwidth between the upper and lower cut off frequencies for boosting by the filter is between 2 kHz and 8 kHz (i.e., 6 kHz in range). The slope of the filter is determined as 25 dB/octave (on both the down rising and falling edges). Application of a filter of this type to a patient suffering from this particular hearing loss profile has the effect of normalizing the spectral intensity of the noise that is perceived by the patient. In the event pure white noise is delivered to the patient through this filter, the patient would perceive the noise as pure white noise.

Example 2

In a second example, a patient presents with a suspected hearing loss and/or tinnitus, and pure tone audiometry is carried out to quantify the type, degree and configuration of hearing (as described above). Psychoacoustic assessment, including Tinnitus Matching (TM), Tinnitus Loudness Matching (TLM) and Minimum Masking Levels (MML) are determined (as described above).

Figure 21:
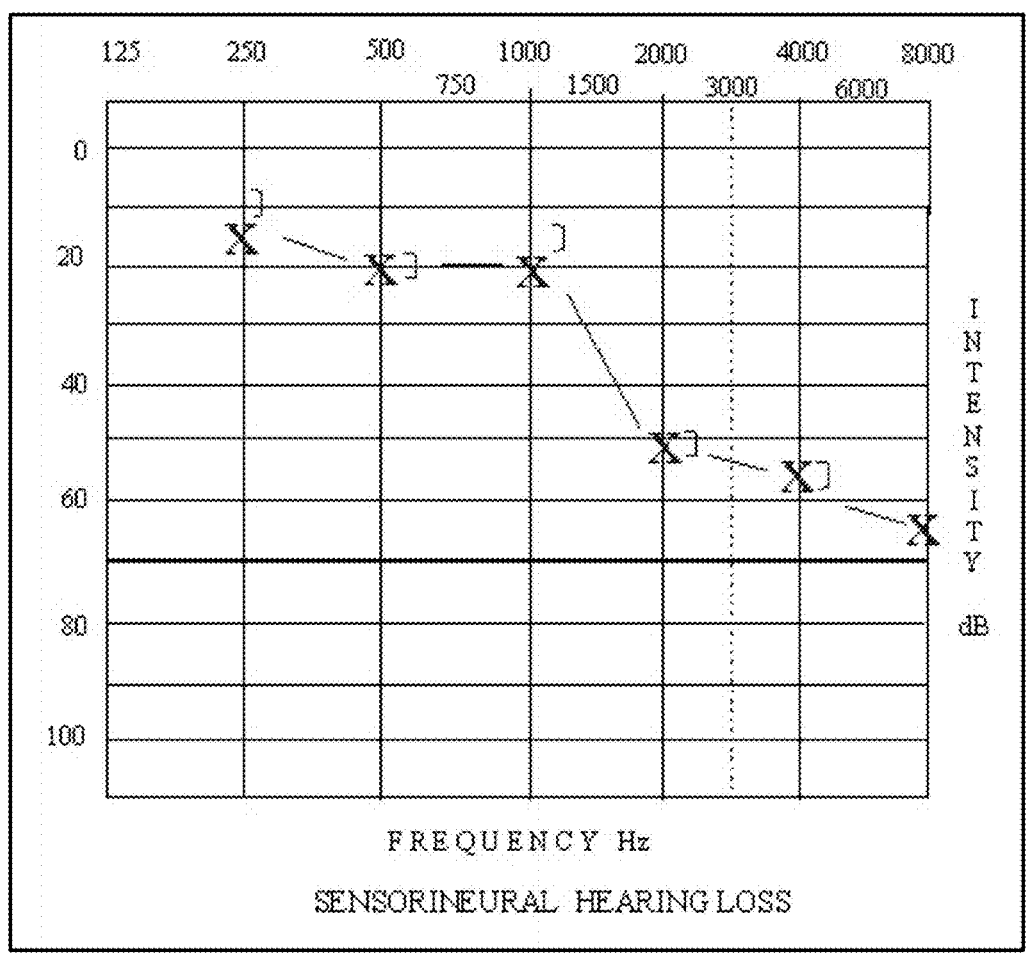
FIG. 21 is a sample audiogram in accordance with the patient of Example 2.

The results of the audiogram for this patient can be seen in FIG. 21, illustrating unilateral high frequency sensorineural hearing loss. The left ear exhibits hearing loss as follows: 2 kHz @ 50 dB, 4 kHz @ 55 dB, and 6 kHz @dB60. The right ear exhibits normal hearing (and is not shown in the audiogram of FIG. 21). The results of the psychoacoustic assessment for tinnitus (not shown in FIG. 21) results in tinnitus matched at a pure tone of 40 dB @ 5 kHz on the left ear, and no tinnitus in the right ear.

Figure 22:
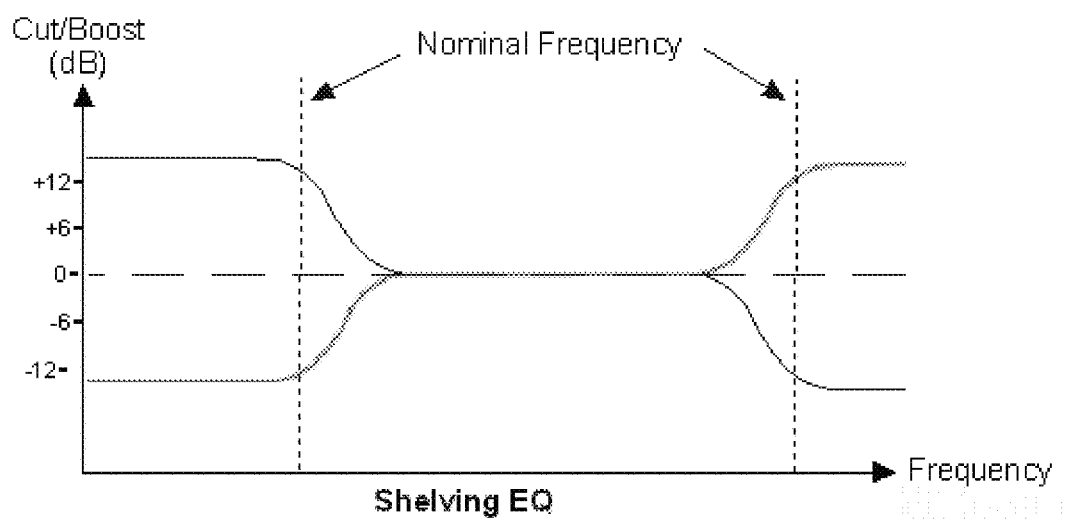
FIG. 22 is an illustrative example of a band boost filter configured to function as a shelf filter produced in accordance with one embodiment of the invention.

In accordance with an embodiment of the invention, a band boost filter is calibrated to function as a high frequency shelf filter (an illustration of which that is not specific to this example is depicted in FIG. 22) based on the above hearing loss and tinnitus assessment. Because the patient exhibits unilateral high frequency hearing loss, in this instance the center frequency is determined as the 3 dB corner frequency—the first point where hearing loss rolls off by 3 dB. The boost ratio is determined in order to boost by a max of +45 dB, the center frequency (Fc) (taken to be as the 3 dB corner frequency) is identified as 1 kHz, and the bandwidth is determined as extending from 1 kHz to the limit of human hearing (approximately 20 kHz). The slope of the filter from the center frequency is determined as 45 dB over 3 octaves (average of the hearing loss between 1 kHz and 8 kHz), equating to 15 dB/octave. Application of a filter of this type to a patient suffering from this particular hearing loss profile has the effect of normalizing the spectral intensity of the noise that is perceived by the patient. In the event pure white noise is delivered to the patient through this filter, the patient would perceive the noise as pure white noise.

Example 3

In a third example, a patient presents with a suspected hearing loss and/or tinnitus, and pure tone audiometry is carried out to quantify the type, degree and configuration of hearing (as described above). Psychoacoustic assessment, including Tinnitus Matching (TM), Tinnitus Loudness Matching (TLM) and Minimum Masking Levels (MML) are determined (as described above).

Figure 23:
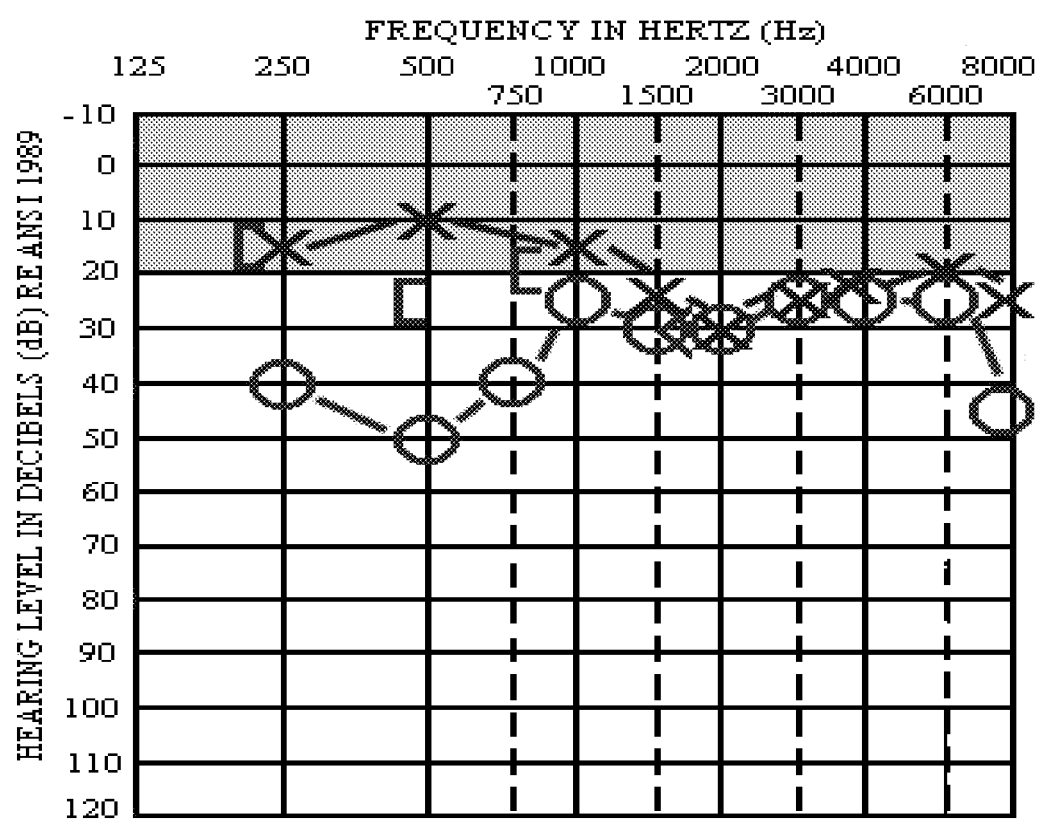
FIG. 23 is a sample audiogram in accordance with the patient of Example 3

The results of the audiogram for this patient can be seen in FIG. 23 (x=left ear, o=right ear), illustrating bilateral mixed loss—sensorineural loss on the left and mixed loss on the right. The left ear exhibits hearing loss as follows: 8 kHz @ 25 dB, 2 kHz @ 20 dB, 250 Hz @ 15 dB. The right ear exhibits hearing loss as follows: 8 kHz @ 45 dB, 2 kHz @ 30 dB, 500 Hz @ 50 dB, 250 Hz @ 40 dB. The results of the psychoacoustic assessment for tinnitus (not shown in FIG. 23) results in tinnitus matched at a pure tone of 15 dB @ 4 kHz on the left ear, and 25 dB @ 2 kHz on the right ear.

In accordance with an embodiment of the invention, a first band boost filter is calibrated to boost certain frequencies of the audio signal to be delivered to the left ear and a second band boost filter is calibrated to function as a hi-lo shelf filter (not shown) for the audio signal to be delivered to the right ear based on the above hearing loss and tinnitus assessment. Based on the audiogram of the left ear, the boost ratio and center frequency (Fc) may be calculated for the left ear band boost filter. In this example, the boost ratio is set in order to boost by +30 dB, the center frequency (Fc) identified as 4 kHz (which in this case is also the tinnitus matching frequency). For the right ear, a first Fc (set as 3 dB Corner Frequency) is identified as 1 kHz (this is the first point where hearing loss rolls off by more than 3 dB for low frequencies) and a second Fc (set as another 3 dB Corner Frequency) is identified as 6 kHz (this is the first point where hearing loss rolls off by more than 3 dB for high frequencies). The slope of the low frequency shelf filter is determined as 15 dB/2 octaves (average of the hearing loss between 1 kHz and 250 Hz)=7.5 dB/octave, and the slope of high frequency shelf filter is determined as 20 dB/half octaves (average of the hearing loss between 6 kHz and 8 kHz)=40 dB/octave. Accordingly, at a frequency of 2 kHz, a boost of +15 dB will be applied. Application of a filter of this type to a patient suffering from this particular hearing loss profile has the effect of normalizing the spectral intensity of the noise that is perceived by the patient in both ears. In the event pure white noise is delivered to the patient through this filter, the patient would perceive the noise as pure white noise.

Example 4

A clinical pilot study into the impact of using a method and device in accordance with an embodiment of the invention for the treatment and symptomatic relief from permanent intractable tinnitus, was conducted, and the findings are discussed below.

Materials and Methods

The objective of the study was to determine the impact of acoustic and tactile multi-modal neuromodulation on objective and subjective measures of permanent intractable tinnitus. This was a 16 week study. Participants were screened for 4 weeks, received treatment for 10 weeks and were followed up at 2 weeks post-treatment. The trial was designed to establish baseline figures for the 4-week run-in period, to compare treatment outcomes over 10 weeks with baseline figures and to assess usage and tolerance of the device over the duration of trial.

The study was conducted by a Clinical Audiologist who is registered with the Irish Society of Hearing Aid Audiologists (ISHAA) and the Irish Academy of Audiology (IAA), under the clinical supervision of a Senior Consultant Otolaryngologist Head & Neck Surgeon who is a member of the Association for Research in Otolaryngology, European Academy of Otology and Neurotology, Royal Society of Medicine: Otology, Laryngology & Rhinology, Prosper Meniere Society, Irish Otolaryngology Society and the American Auditory Society.

Eligibility of study participants was determined by the inclusion and exclusion criteria, as listed below. Patients were deemed eligible if they complied with the following; the minimum total use of the device should be 30 minutes per day, i.e., 3.5 hours per week; the level of stimulus should be greater than zero; acceptable timing for visit dates: Baseline interview had to be conducted within 4 weeks from the start of the new treatment.

Inclusion Criteria: Aged <65; Suffering from intractable subjective tinnitus for more than 6 months; Tinnitus associated with an age or noise related sensorineural hearing loss; Have English reading, comprehension and written skills; Able and willing to participate in the study for the full 16 weeks duration, Informed consent.

Exclusion Criteria: Ulceration of oral cavity or tongue; oral mucosa or significant intra-oral disease—to mitigate risk of further aggravation of these symptoms; Meniere's Disease—due to the fluctuating hearing loss patients normally present with Hyperacusis—to avoid further aggravation of sensitivity of sound; Current medical legal cases regarding tinnitus or hearing—in order to avoid any conflict of interest; Undergoing any treatment for tinnitus—in order to accurately measure the independent effect of the intervention; Pacemakers—due to potential magnetic interference.

Non-Eligibility and Withdrawals

Participants who were not deemed eligible at prescreen to take part in this particular study were referred back to their GP and received a formal letter of refusal. Participants who withdrew after commencement of this study were analyzed according to the intention-to-treat (ITT) method. Patients were informed that participation in the study was entirely voluntary, and they were free to withdraw from the study at any time without having to give a reason. The recruitment process allowed patients adequate time to fully consider participation.

Minimizing Bias

Bias was minimized through anonymized participation and the use of objective and subjective gold standard outcome measures.

Treatment

The Pre-Treatment Phase consisted of a four-week run-in period prior to commencement of treatment where baseline measures were obtained and sampled every 2 weeks at Week 0, Week 2 and Week 4. The Treatment Phase consisted of a 10-week period where participants used the device for a recommended 60 minutes per day in their home. All participants' usage of the device was logged on an internal SD reader card. Objective and subjective tests as described above were carried out at the enrolment visit and every two weeks for the duration of study.

Assessment of Outcome Measures and Compliance

Primary outcome measures were assessed across the duration of the study in the clinical environment at 'review' visits. Participants' compliance was measured using data logging methodology and tolerability assessed on completion of the study through a questionnaire.

Subjective Outcome Measures

The Tinnitus Handicap Inventory (THI) is a 25-item self-reporting questionnaire for the measurement of tinnitus. Patients completed THI questionnaires every two weeks, immediately prior to review visits. THI scores are categorized into five grades of severity that range from 'slight' to 'catastrophic'.

Objective Outcome Measures

Tinnitus Matching (TM) is a psychoacoustic assessment, which determines the frequency pitch of the tinnitus. Tinnitus Loudness Matching (TLM) is a psychoacoustic assessment, which determines the intensity of the tinnitus Minimum Masking Level (MML) is a psychoacoustic assessment, which determines the lowest level of noise required to mask the tinnitus. Patients underwent TM, TLM and MML assessments every two weeks at review visits.

Materials

An auditory and tactile stimulation device in accordance with an embodiment of the invention was used in the study. The non-invasive device was capable of simultaneously delivering auditory stimuli to the ears through hi-fidelity headphones and tactile patterns through an array of thirty-two transcutaneous electrical stimulators on the tongue.

In this study, the device was used to deliver an auditory stimulus that included broad-spectrum sound (referred to herein as "colored noise") and relaxing music that were band-boost filtered to match the patient's audiogram. Simultaneous to the auditory stimulus, the device presented transcutaneous electrical stimulation of the anterio-dorsal surface of the tongue, where the electrical stimulus was a spatio-temporal encoded pattern that represented the instantaneous frequency-domain coefficients of the auditory stimulus.

Results and Analysis

Analysis Population and Compliance

Statistical analysis was carried out on data from the Intent-To-Treat population. Participant data was deemed eligible if they met the following compliance and minimum appliance requirements: Minimum total use of 30 mins per day or 3.5 hours per week; Minimum level of stimulus; greater than zero; Review visits within one week of scheduled dates.

Demographics and Baseline Characteristics

Baseline measures and basic demographic data (age/gender) were obtained during the pre-treatment phase.

Summary tables and figures are presented below for each characteristic:

TABLE 11

| Age-summary statistics | | | | |
|---|---|---|---|---|
| | N | Mean | Std. Dev. | Min | Max |
| Age | 54 | 47 | 11 | 21 | 64 |

TABLE 12

| Age distribution | | | |
|---|---|---|---|
| Age Category | Frequency | Percentage | Cum. Percentage |
| <30 | 4 | 7.41 | 7.41 |
| 30-39 | 11 | 20.37 | 27.78 |
| 40-49 | 16 | 29.63 | 57.41 |
| 50-59 | 15 | 27.78 | 85.19 |
| 60-69 | 8 | 14.91 | 100.00 |
| Total | 54 | 100.00 | |

Average age of the group was 47. The youngest patient was 21 and the eldest was 64. Over half of the patients (57%) were under the age of 50. 34 (63%) patients were male and 20 (37%) patients were female.

Hearing Loss Profile

Hearing loss profile was measured for left and right ear individually using GN Otometrics Madsen Astera Clinical Audiometer, calibrated in accordance with BS EN 60645-1 (IEC 60645-1) and the relevant BS EN ISO 389 (ISO 389) series standards. Hearing loss was classified according to severity: Normal, Mild, Mild to Moderate, Moderate, Moderate to Severe, Severe. The distribution of severity is summarized in the following tables.

TABLE 13

Hearing Loss Profile at Screening-Left Ear

| Grade | Freq | Percentage | Cum. Percentage |
|---|---|---|---|
| Normal | 4 | 7.41 | 7.41 |
| Mild | 19 | 35.19 | 42.59 |
| Mild to Moderate | 25 | 46.30 | 88.89 |
| Moderate | 4 | 7.41 | 96.30 |
| Moderate to Severe | 1 | 1.85 | 98.15 |
| Severe | 1 | 1.85 | 100.00 |
| Total | 52 | 100.00 | |

TABLE 14

Hearing Loss Profile at Screening-Right Ear

| Grade | Freq | Percentage | Cum. Percentage |
|---|---|---|---|
| Normal | 2 | 3.77 | 3.77 |
| Mild | 20 | 37.74 | 41.51 |
| Mild to Moderate | 27 | 50.94 | 92.45 |
| Moderate | 4 | 7.55 | 100.00 |
| Moderate to Severe | 0 | 0.00 | |
| Severe | 0 | 0.00 | |
| Total | 50 | 100.00 | |

In the majority of cases the severity of hearing loss at screening ranged between mild and moderate. Very few cases were diagnosed as severe.

Tinnitus Profile

The tinnitus profiles of patients were measured at screening using the following scores: THI, MML, TLM and TM Summary statistics are shown in the following table.

TABLE 15

Tinnitus Scores at Screening-Summary Statistics

| Score | N | Mean | Std. dev. | Min | Max |
|---|---|---|---|---|---|
| THI | 54 | 40.1 | 22.4 | 6 | 94 |
| MML | 54 | 50.8 | 17.1 | 15 | 85 |
| TM | 54 | 6518 | 3387 | 250 | 12500 |
| TML | 54 | 42.9 | 19.7 | 10 | 85 |

Analysis

The Impact of acoustic and tactile multi-modal neuromodulation on objective and subjective measures of permanent intractable tinnitus was determined by measuring the change in the THI, MML, TLM and TM scores over time. Scores were obtained at screening V0 and Baseline V2 and every 2 weeks for duration of study. Comparisons were made between Baselines V2 (Week 4/1st Week of treatment) and V7 (Week 14/10 weeks of treatment) for main effect and between Baseline V2 and V4 (Week 8/4 weeks of treatment) for interim effect. A placebo/context effect was explored as a comparison between screening visit V0 and baseline V2, where participants have not yet received treatment. Short term effects of treatment were measured as comparison between last week of treatment V7 (Week 14/10 Weeks of treatment) and V8 (Week 16/2 weeks post treatment).

Boxplots and repeated ANOVA were run for all sampled measures to determine statistical significance. Paired t-tests were carried out to compare main effect (change between baseline V2 and V7 (Week 14/10 Weeks of treatment)) and interim effect (change between baseline V2 and V4 (Week 8/4 Weeks of treatment).

The potential placebo/context effect was analyzed in an exploratory manner comparing measures at V0 and Baseline V2. This was a 4 week run-in period in which intervention is not administered, but some beneficial effect may have been observed due to the subjective nature of tinnitus. Paired t-tests compared Screening visit V0 and Baseline V2 to test evidence of potential placebo/context effect.

Minimum Masking Level (MML)

Figure 24:
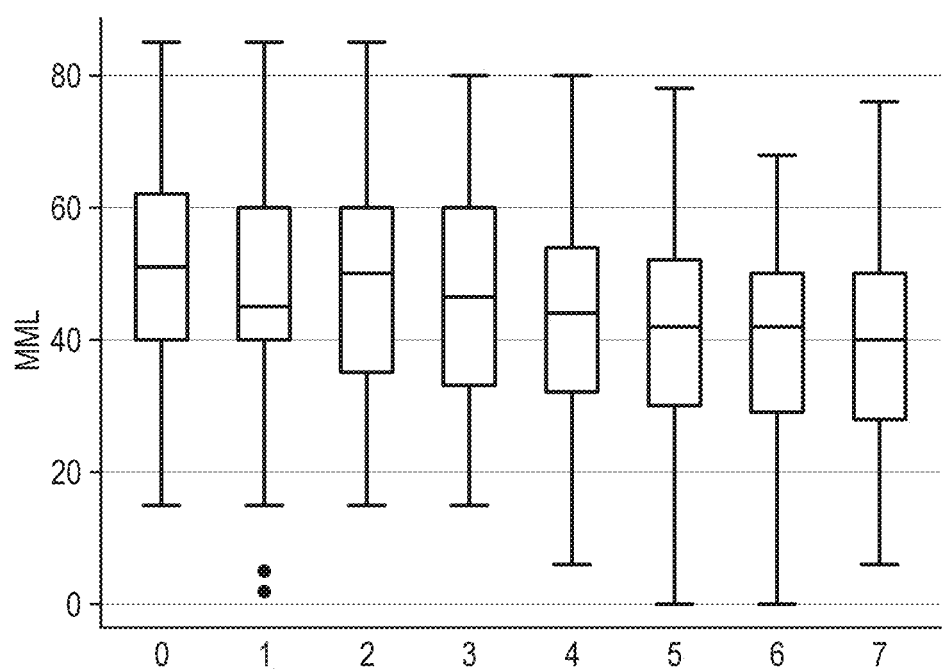
FIG. 24 is a boxplot of MML from Screening Visit (V0/Week 0) to End of Treatment Visit (V7/Week 14) in accordance with the study described in Example 4.

Change in MML score over time was shown in FIG. 24. Overall repeated ANOVA was statistically significant (p-value <0.001). Paired t-test comparison between Baseline V0 and V7 (Week 14/10 Weeks of treatment) was also significant (p-value <0.001). MML score decreased from an average value of 47.4 (SD=2.54, 95% CI: 42.3-52.6, N=39) at Baseline V2 to 38.8 (SD=2.7, 95% CI: 33.4-43.34, N=39) at V7 (Week 14/10 Weeks of treatment). Interim effect, (average change in MML from baseline V2 to V4 (Week 8/4 Weeks of treatment), was also significant (p-value=0.0088), it decreased from 48.15 (SD=2.69, 95% CI: 42.66-53.64, N=33) at Baseline V0 to 43.79 (SD=3.13, 95% CI: 37.4-50.16, N=33) at V4 (Week 8). There was some evidence of a placebo/context effect for the MML score, but it was not significant (p-value=0.01). Between screening visit V0 and baseline V2 the average MML score changed from 50.8 (SD 2.3) V0 to 46.7 (SD 2.2) (N=54) V2.

Tinnitus Loudness Matching (TML)

Figure 25:
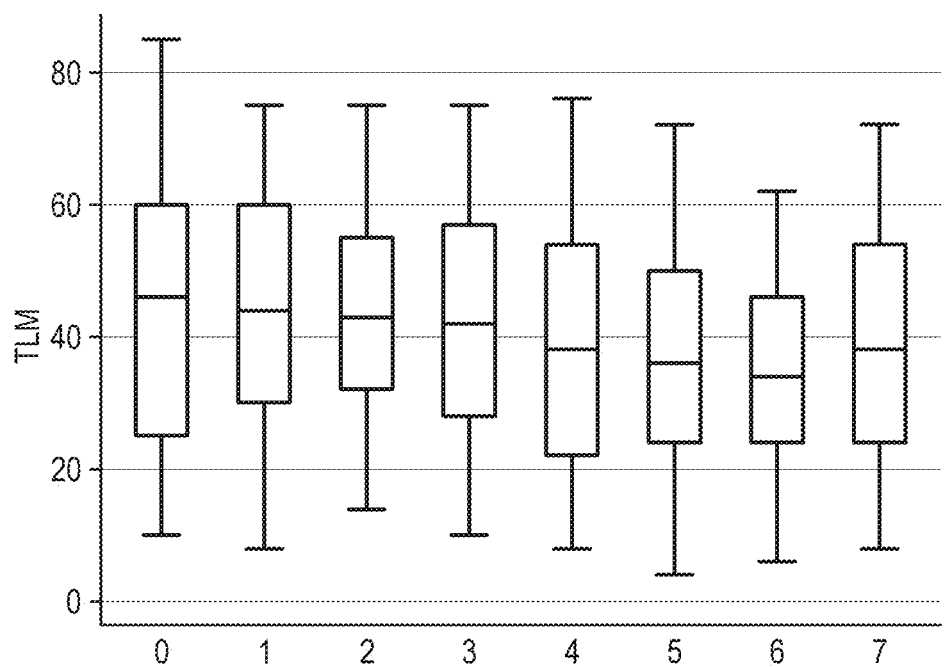
FIG. 25 is a boxplot of TLM from Screening Visit (V0/Week 0) to End of Treatment Visits (V7/Week 14) in accordance with the study described in Example 4.

The change of TLM score over time is shown in FIG. 25. The overall repeated ANOVA is statistically significant (p-value <0.001). The paired t-test comparison between V2 Baseline and V7 (Week 14/10 Weeks of treatment) was also significant (p-value=0.001). The TLM score decreased from an average value of 45.3 (SD=2.5, 95% CI: 40.2-50.4, N=39) at Baseline (V2) to 38.1 (SD=2.75, 95% CI: 32.5-43.6, N=33) at V7 (Week 14/10 Weeks of treatment). Interim effect, (average change in TML from baseline V2 to V4 (Week 8/4 Weeks of treatment)), was also significant (p-value=0.045), it decreased from 44.63 (SD=2.61, 95% CI: 39.31-50, N=33) at Baseline V2 to 40.18 (SD=3.28, 95% CI: 33.5-46.85, N=33) V4 (Week 8/4 Weeks of treatment). There was no evidence of a placebo/context effect for TLM score. Average change between screening visit V0 and Baseline V2 was less than 1 point, changing from 42.9 (SD 2.68) to 43.4 (SD 2.1), and was not significant.

Tinnitus Handicap Inventory (THI)

Figure 26:
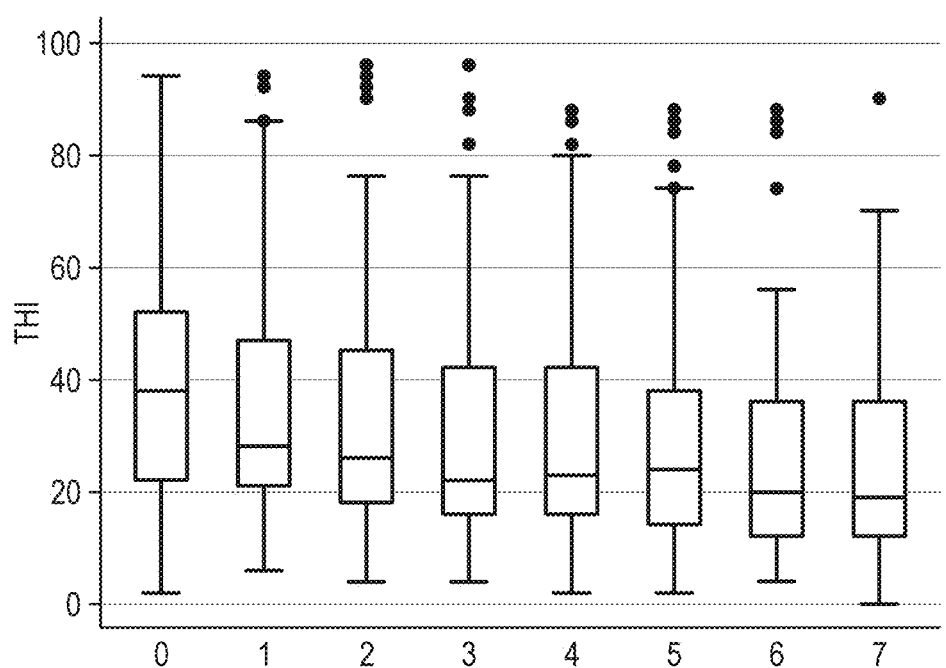
FIG. 26 is a boxplot of THI from Screening Visit (V0/Week 0) to End of Treatment Visit (V7/Week 14) in accordance with the study described in Example 4.

Change in THI score over time is shown in FIG. 26. Overall repeated ANOVA was statistically significant (p-value <0.001). Paired t-test comparison between Baseline V2 and V7 (Week 14/10 Weeks of treatment) was also determined to be significant (p-value <0.001). THI score decreased from an average value of 34.3 (95% CI: 27.3-41.2, N=46) at Baseline V0 to 24.9 (95% CI: 19.8-30.7, N=42) at V7 (Week 14/10 Weeks of treatment). Interim effect (average change in THI from baseline V2 to V4 (Week 8/4 Weeks of treatment), was also significant (p-value=0.0052), decreased from 34.42 (95% CI: 27.5-41.3, N=50) at Baseline V2 to 31.12 (95% CI: 24.2-38.1, N=50) at V4 (Week 8/4 Weeks of treatment). Significant placebo/context effect was determined for THI score. Average THI score dropped from 41.1 (SD 3.04) to 34.2 (SD 3.2) (N=54) from V0 screening visit to V2 baseline visit and the change was statistically significant (p-value <0.001).

Tinnitus Matching

Figure 27:
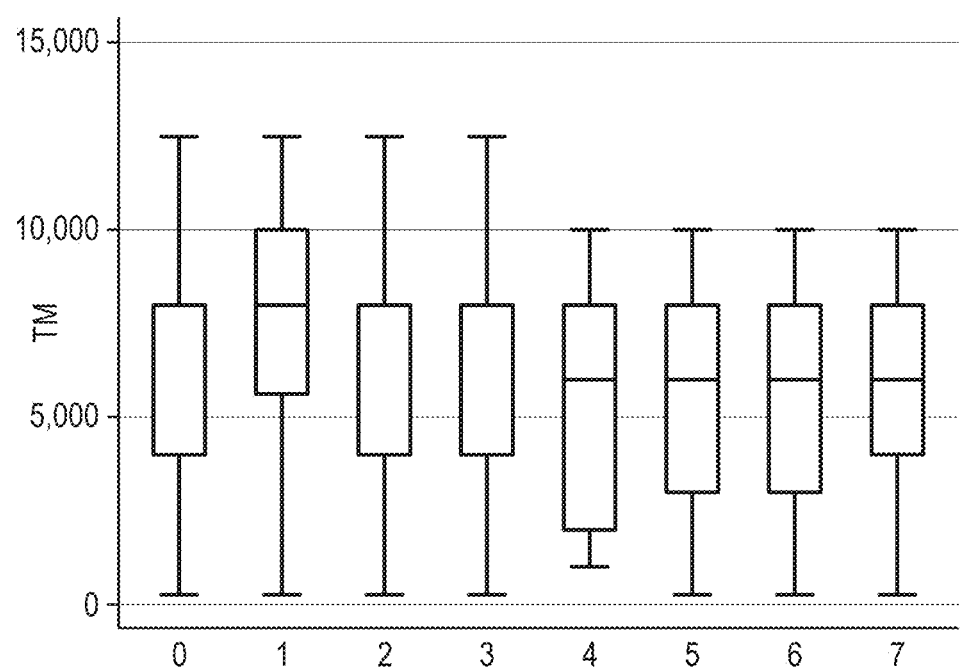
FIG. 27 is a boxplot of TM from Screening Visit (V0/Week 0) to End of Treatment Visit (V7/Week 14) in accordance with the study described in Example 4.

Change of TM score over time is shown in FIG. 27. Overall repeated ANOVA showed some trend of decreasing values, but was not significant Summary values for each visit are presented in the following table.

TABLE 16

TM Score-Summary Statistics

| Visit | N | Mean | Std. Dev. | Min | Max |
|---|---|---|---|---|---|
| 0 | 54 | 6518 | 3387 | 250 | 12500 |
| 1 | 42 | 7395 | 3437 | 250 | 12500 |
| 2 | 54 | 6199 | 3319 | 250 | 12500 |
| 3 | 40 | 6343 | 3380.1 | 250 | 12500 |
| 4 | 33 | 5454 | 3327 | 1000 | 10000 |
| 5 | 37 | 5574 | 3155 | 250 | 10000 |
| 6 | 40 | 5756 | 3105.8 | 250 | 10000 |
| 7 | 39 | 5814 | 3093 | 250 | 10000 |

Discussion

This study demonstrates early evidence of tangible efficacy and suggests that this novel intervention is a promising development in the treatment of tinnitus. The patient group demonstrated a statistically significant mean improvement in objective measures, exhibiting a reduction of 8.6 dB in Minimum Masking Level and 7.2 dB in Tinnitus Loudness Matching between Baseline Visit (V2/Week 4) and End of Treatment Visit (V7/Week 14). These results compare favorably to other studies using similar objective measures [neuromonics 7.68 dB reduction @ 2 months]. Similarly, the patient group demonstrated a statistically significant improvement in the THI subjective measure. This is a particularly significant outcome, given that, unlike other treatments, the intervention being assessed here does not include psychological counseling. This compares favorably to studies involving other stand-alone (without counseling) technologies.

Example 5

This example describes the reduction to practice investigation (clinical trial) of MB1 configuration of the tinnitus treatment device with a therapy designed to alleviate tinnitus symptoms via sensory stimulation. The trial was carried out in a clinical setting with participants suffering from tinnitus.

Subjects

This prospective single arm pilot study was conducted with approval from the Research Ethics Committee of the National University of Ireland, Maynooth and The Hermitage Medical Clinic, Dublin. Self-referred patients that met inclusion/exclusion criteria (see below) were recruited in the order that they presented at the clinic and not pre-selected in any way. Sixty-four participants were screened for eligibility and written informed consent was obtained from 54 suitable participants (19 female; mean=45 yrs, range 28-64 yrs, 35 male; mean=47 yrs, range 21-64 yrs) with subjective, chronic tinnitus. The exact definition of chronic tinnitus varies in the literature but generally refers to tinnitus that has not self-resolved in the short to medium term, i.e. six months, and persistent tinnitus refers to tinnitus that is present every day. Participants were informed that participation in the study was entirely voluntary, and they were free to withdraw from the study at any time without having to give a reason. The recruitment process allowed participants adequate time to fully consider participation. Participation was anonymous. The eligibility of study participants was determined by the following inclusion and exclusion criteria:

Inclusion Criteria:
 Aged <65
 Suffering from persistent, subjective tinnitus for at least the previous 6 months
 Age or noise related sensorineural hearing loss (>25 dBHL in at least one ear).
 Have English reading, comprehension and written skills
 Able and willing to participate in the study for the full 14 week duration
 Informed consent Exclusion Criteria:
 Ulceration of oral cavity or tongue, oral mucosa or significant intra-oral disease—to mitigate risk of further aggravation of these symptoms
 Meniere's Disease—due to the fluctuating hearing loss normally associated with the condition
 Current medical legal cases regarding tinnitus or hearing—in order to avoid any conflict of interest
 Currently undergoing any pharmacological or electrical stimulation-based treatment for tinnitus—in order to accurately measure the independent effect of the intervention
 Pacemakers—due to potential electromagnetic interference Participants who were not deemed eligible at pre-screen to take part in this particular study were referred back to their general practitioner (i.e., primary care physician) and received a formal letter of refusal.

Study Design

This was a 14-week single-arm pilot study to assess the feasibility of auditory and somatosensory bi-modal stimulation and its effect on tinnitus outcome measures. The study population was not powered for significance as this was an observational study. Participants visited the clinic every two weeks for the duration of the study, i.e. 14 weeks (V0 at Week 0, V1 at Week 2, etc.). Participants were screened without any intervention in a clinical setting for the first 3 screening visits, two weeks between each, to establish baseline clinical measures of tinnitus severity (pre-treatment). The participant was not required to perform any tasks in-between these visits. Participants were assessed by employing the most commonly used psychoacoustic and psychometric tinnitus measures including—Minimum Masking Level (MML), Tinnitus Loudness Matching (TLM) and Tinnitus Handicap Inventory (THI). The screening assessments were carried out during periods without any stimulation from the device.

There are several factors outside of the treatment of the condition that can affect the perceived benefit from any treatment of tinnitus. Hesser et al (The effect of waiting: A meta-analysis of wait-list control groups in trials for tinnitus distress. J Psychosom Res. 2011 April; 70(4):378-84) reviewed the response rates of participants on a waitlist for tinnitus treatments and found that participant's distress can reduce over short wait periods. This improvement can be attributed to the attention and reassurance the participant receives from the investigator and/or a knowledgeable professional, factors known to contribute to alleviation of tinnitus symptoms. The screening phase in this study was employed to address improvements in symptom severity achieved due to this anticipatory effect from study participation. Assessment scores from the third screening visit were set as baseline values. It was expected that any improvement from the therapeutic effect of study participation would be mitigated by the third visit.

At the third visit participants were provided with the neuromodulation device to take home for the remainder of the study and asked to use it for between 30 and 60 minutes every day for the next 10 weeks. Participants were shown how to use the device and told to set the audio and tongue stimulation to the most comfortable levels for them. Participants were asked to return to the clinic every two weeks in order to repeat the assessments carried out in the screening period. Where it was not possible for participants to return to the clinic, they completed the paper version of the THI remotely and sent the copy to the investigator site. Participants were advised to terminate device use and to contact the investigator if they experienced any side-effects or adverse events. They were also instructed to contact a member of the research team regarding any device malfunction.

The study was conducted by a clinical audiologist who is registered with the Irish Society of Hearing Aid Audiologists and the Irish Academy of Audiology, under the clinical supervision of a senior consultant otolaryngologist head & neck surgeon who is a member of the Association for Research in Otolaryngology, European Academy of Otology and Neurotology, Royal Society of Medicine: Otology, Laryngology & Rhinology, Prosper Meniere Society, Irish Otolaryngology Society and the American Auditory Society. The same audiologist performed all assessments. Assessment scores were recorded in a paper-based system, meaning the audiologist was not blinded from previous results. However, the audiologist did not refer to previous assessment scores during evaluation.

Compliance Monitoring and Data Inclusion Criteria

Participant compliance with treatment administration was determined technologically using the data logging function on the device. The following events, along with their date and time, were recorded in non-volatile memory:
  Power on/off and treatment start/pause/resume events
  Audio volume and somatosensory stimulus intensity settings
  Electrical current magnitude delivered via the electrodes (used to determine participant contact)
  Battery voltage level
  Error events
  Participant safety was assessed at each clinical visit.

While there is no definitive prescription for treatment duration, the 10 weeks of treatment employed in this study was based on a similar study of neuromodulation by Tyler et al. (Tyler, R., Haskell, G., Preece, J. and Bergan, C. (2001) Nurturing patient expectations to enhance the treatment of tinnitus. Seminars in Hearing, 22, 15-21). In the event that participants did not complete the final assessment, scores from the penultimate assessment were used.

The protocol required participants to use the device for between 30 and 60 minutes a day, 7 days a week. Compliance in this context refers to the number of days over the course of the treatment where the session duration, i.e. how long the device was used continuously, was at least 30 minutes. In clinical studies of pharmaceuticals, participants are considered compliant if their adherence is greater than 80%. The exact durational properties of this treatment are still under investigation and so a somewhat more generous cut off for compliance was employed, i.e. 66%; the cohort was divided into those that are considered 'compliant' and those that are considered 'non-compliant' according to this threshold.

Analysis

The data set for this study consisted of THI, TLM and MML data from 44 participants over 10 weeks of treatment. Data on compliance to study protocol as well as audio and somatosensory stimulation settings used by the participants over the ten weeks was also collected. Participant data was included in the analysis if tinnitus symptom scores were available for baseline (V2) and at least the penultimate visit, and if they had access to the device for at least 8 weeks, i.e., did not return the device early. The analysis in this paper investigates whether any statistical improvement in the three assessments of tinnitus symptoms was observed after 10 weeks of treatment with the device.

THI scores are not normally distributed, so the Wilcoxon signed rank test was employed to test for statistical significance between baseline (V2) and final visit. TLM and MML datasets were found to be normally distributed and a paired t-test was employed to test for statistically significant differences between baseline (V2) and V7. In addition to analysis of statistical difference, the proportion of participants achieving clinically significant differences was assessed. Jastreboff et al. (Jastreboff P J, Hazell J W, Graham R L. Neurophysiological model of tinnitus: dependence of the minimal masking level on treatment outcome. Hear Res. 1994 November; 80(2):216-32) reported that a decrease in 5.3 dB on the MML scale significantly correlated to patients reporting improvements in their tinnitus. While Zeman et al (Zeman F, Koller M, Figueiredo R, Aazevedo A, Rates M, Coelho C, Kleinjung T, de Ridder D, Langguth B, Landgrebe M. Tinnitus handicap inventory for evaluating treatment effects: which changes are clinically relevant? Otolaryngol Head Neck Surg. 2011 August; 145(2):282-7) demonstrated that a 7 point drop in THI score also reflects a clinically significant improvement. No clinically significant reduction for TLM could be found in the literature so the 5.3 dB for the MML was employed. The participants were classed as improvers or non-improvers based on the differences in their symptom scores from baseline (V2) to V7 in reference to these values for clinical significance.

The log files provided information on device usage as well as stimulus levels over the course of treatment for both auditory and somatosensory stimuli. Secondary analysis examined patterns of auditory and somatosensory stimulus to investigate any insights into participant's usage of the device.

Study Registration

The Research Ethics Committee of the National University of Ireland, Maynooth or the Hermitage Medical Center did not require registration to a clinical trials registry prior to approval. The study was considered a feasibility study, and is therefore exempted from registration under FDAAA 801.

Results

As detailed above, the impact of auditory and somatosensory multi-modal stimulation, on outcome measures of chronic tinnitus, was determined by measuring the change in the THI, MML and TLM scores over time. A cohort of 54 participants was recruited as part of this trial, each participant was required to complete 3 intervention free screening assessments and 5 subsequent assessments while using the device.

Two participants dropped out of their own accord. The log files from the devices of six additional participants showed very little use of the device over the study period, <10% compliance. Two additional participants were excluded from analysis; while their corresponding log files showed active use of the device, they did not return for any assessment visits after the V3 assessment. In total ten participants were excluded from the final analysis.

Figure 15:
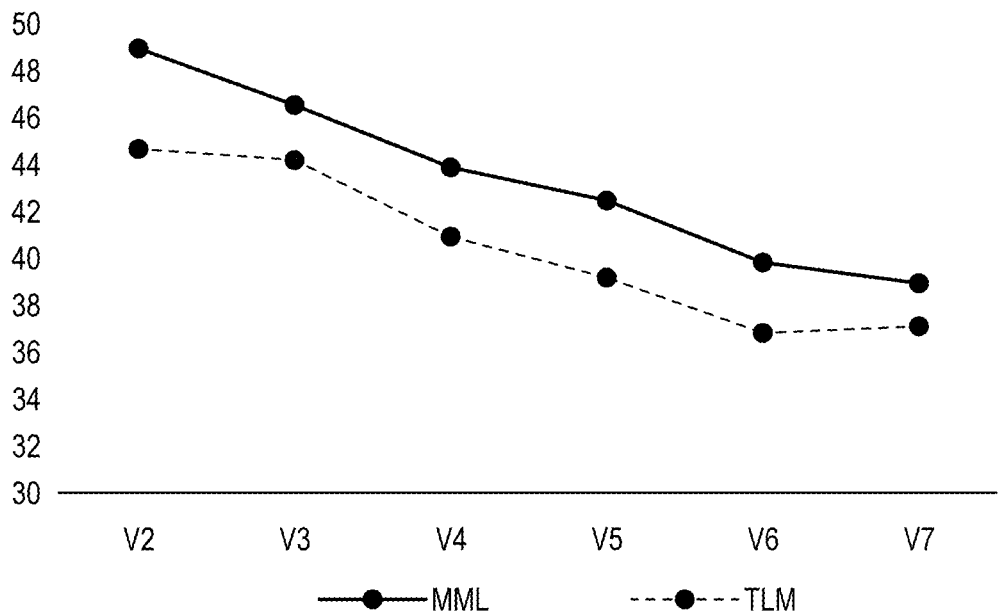
FIG. 15 illustrates performance in response to treatment over a 10 week treatment period in response to clinical trials carried out in accordance with an embodiment of the present invention.
Figure 15:
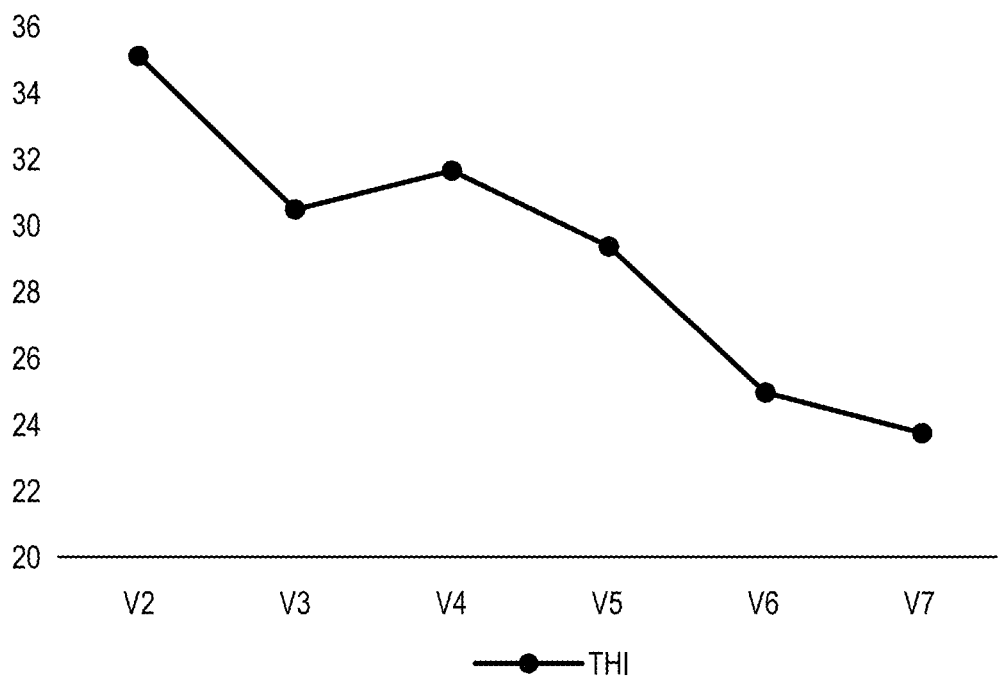
Figure 16:
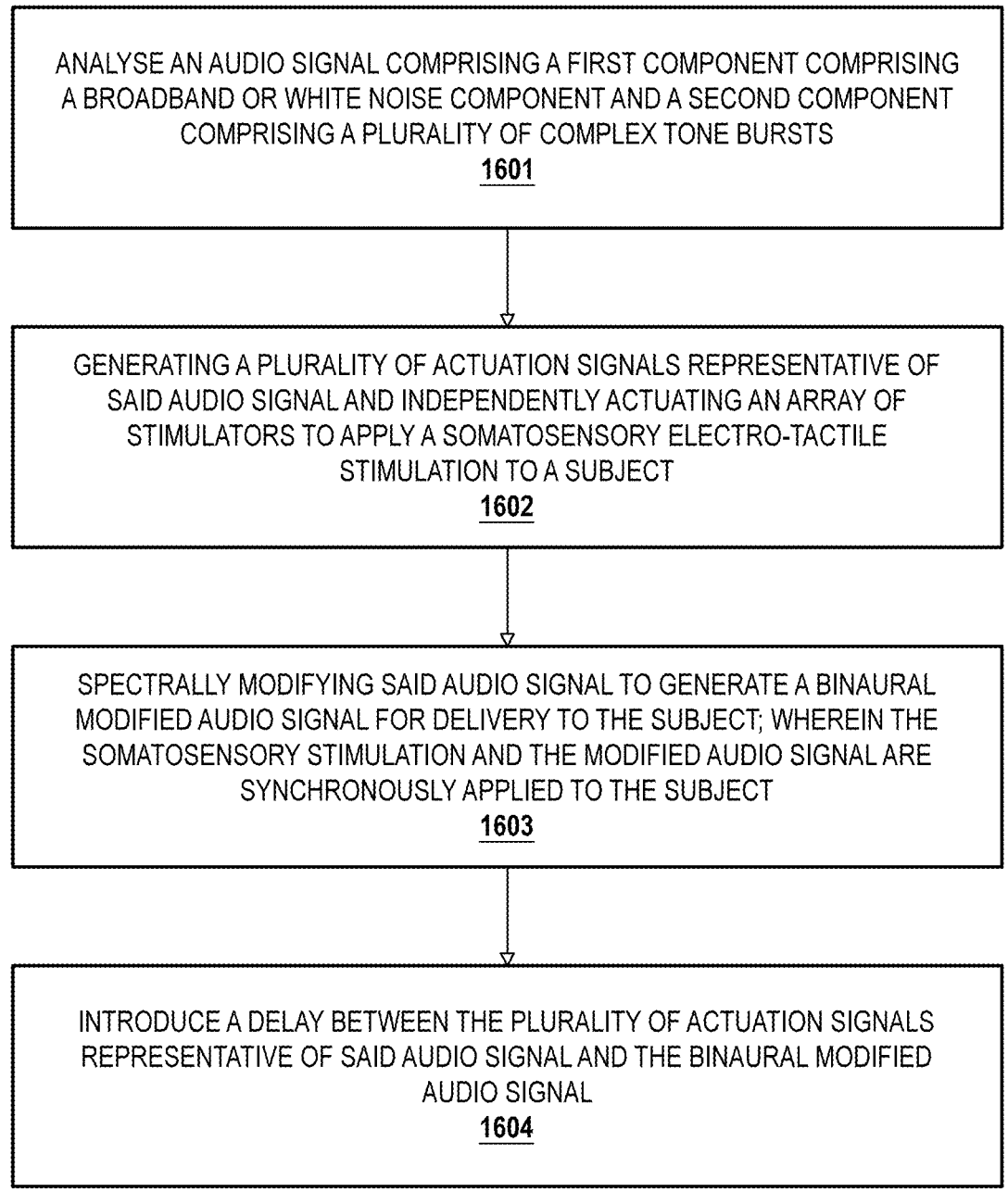
FIG. 16 is a method of treatment in accordance with an embodiment of the present invention.

The symptom scores assessed without intervention at V0, V1 and V2, are employed to better understand variability and improvements in symptoms that may be attributed to non-interventional influences. The average intra-subject coefficient of variance, COV, for the THI, TLM and MML scores over the 3 screening visits, i.e. non interventional monitoring, are 21%, 16% and 13% respectively. Baseline values for analysis were taken from the 3rd screening visit, i.e. V2, average and standard variation can be seen in Table 19. Changes in the average THI, TLM and MML scores, for the full cohort over time, are presented in FIG. 15.

Included in analysis, N=54

TABLE 17

Demographic profile of participants

| Age | 47.5 ± 11 |
|---|---|
| Men | 34 (63%) |
| Tinnitus type: pure tonal/narrowband | 31 (66%)/16 (34%) |
| Persistence of tinnitus: >2 years/<2 years | 36 (78%)/10 (22%) |
| Tinnitus presence: one ear/both ears | 12 (26%)/34 (74%) |
| Tinnitus severity, (VAS)$^x$ | 6.5 ± 2.2 |
| Tinnitus pitch, (VAS) | 7.1 ± 2.4 |
| Hyperacusis: yes/no | 13 (28%)/41 (72%) |
| Tinnitus type: constant/fluctuate/other | 31 (57%)/15 (28%)/8 (15%) |
| Taking anti-depressant medications | 5 (11%) |

$^x$Self-rated Visual Analog Scale, scale 1-10

Table 18 presents the number of participants who achieved clinically significant improvements, as discussed in the analysis section, per symptom, for those that are considered compliant and non-compliant. The highest proportion of improvers are seen on the MML scale, 73% of the 30 participants demonstrating a clinically significant improvement in MML.

TABLE 18

The number of improvers/non-improvers for each tinnitus symptom in each compliance class

|  | Improvers: THI* | Improvers: TLM§ | Improvers: MML ? |
|---|---|---|---|
| Full Cohort (44) | 20 (45%) | 21 (48%) | 28 (64%) |
| Compliant (30) | 17 (57%) | 15 (50%) | 22 (73%) |
| Non-Compliant (14) | 3 (21%) | 6 (43%) | 6 (43%) |

*Improvers achieve a minimum drop of 7 points on THI scale
§Improvers achieve a minimum drop of 5.3 dB on TLM scale
?Improvers achieve a minimum drop of 5.3 dB on MML scale Table 19 presents the average THI, TLM and MML scores for baseline (V2) and V7 for the full cohort and when the cohort is divided into two classes; compliant and non-compliant.

TABLE 19

Average tinnitus symptom values for baseline and final visit,

|  | THI (pts) | | TLM (dB) | | MML (dB) | |
|---|---|---|---|---|---|---|
|  | V2 (SD) | V7 (SD) | V2 (SD) | V7 (SD) | V2 (SD) | V7 (SD) |
| Full Cohort (44) | 33.7 (24) | 25.1 (20)*** | 42.9 (15) | 37.5 (17) | 47.3 (15) | 39.2 (17)*** |
| Compliant (30) | 35.8 (25) | 24.1 (20)*** | 44.8 (16) | 37.3 (16)*** | 49.0 (15) | 39.2 (18)*** |
| Non-compliant (14) | 29.3 (24) | 27.4 (23) | 38.6 (14) | 37.7 (19) | 43.8 (17) | 39.1 (18) |

*$p < 0.05$,
**$p < 0.01$,
***$p < 0.001$

The log files from the device provided information on the usage patterns for stimulation parameters used by the participants. Data from three participants was excluded from this analysis due to errors in the electronic logging system. On the days the device was used, the average session duration for all participants was 47 mins (SD=20 mins) Table 20 presents the usage statistics.

TABLE 20

|  | Average number of compliant days (SD) | Average session duration on day the device used, mins (SD) |
|---|---|---|
| Compliant (30) (* > 44 days with session duration > 30 mins per day) | 59 (12.3) | 52 (18) |
| Non-Compliant (14) (* < 44 days with session duration > 30 mins per day) | 33 (9.4) | 33 (17) |

*The average treatment duration across the whole group (N = 44)** was 67 days. Hence a 66% compliance threshold corresponds to 44 days.
**Total number of subjects: 54; Excluded from analysis (10): did not use device (3), drop outs before intervention (3), did not complete assessments schedule (4)

The average somatosensory and audio stimulus settings after the first week of use were 6pt (SD=4.2) (min 0 and max 17) and −8.5 dB (SD=8.1 dB) respectively. The average somatosensory and audio stimulus setting extracted from log files for the final week were 7.4 pts (SD=5.4) and −16 dB (SD=6.6 dB) respectively. There was no statistical difference between the stimulus setting at the beginning and end of treatment. Participants were able to modify the volume of the audio and the intensity of the somatosensory stimulus over the 10 weeks of treatment. From the log data it was observed that participants varied the somatosensory stimulus much more than the audio stimulus; the coefficient of variation was calculated for each participant across the 10 weeks of intervention, the COV across the full cohort was 35% and 15% for somatosensory and auditory stimulus settings, respectively. There was no significant relationship established between stimulus settings and changes in symptom scores for either improvers or non-improvers. While no specific assessments of ease of use and tolerability was carried out, no participants reported significant discomfort during assessments at the investigator site.

Example 6

In order to validate required pulse width range to achieve similar stimulus intensity in the MB2 compare to the MB1, in-vivo testing of the MB2 ETS were carried out with Vpeak=4.35V, the series DC blocking capacitor Cs=47 nF and with circular cross section 316L electrodes of 1 mm diameter. With these settings, the voltage across Cs would increase by 1.35V on average across subjects by the end of the pulse period. Therefore, the charge delivered, q, =CV=47 nF*1.35V=63.5 nC. These tests were conducted on 10 adults (5 male, 5 female, average age 42 years) and the results were:
  The minimum pulse width perceivable was 10 us (range 5 us to 15 us)
  The minimum pulse width required to elicit a strong sensation was 50 us (range 35 us to 65 us)
These results are consistent with the ranges for stimulus amplitude adjustment used in the MB2 design.

Example 7

A study was conducted on tinnitus patients to determine the effect of the audio and somatosensory stimulation therapy described above on a subject's anxiety level independent of any concomitant changes in levels of tinnitus. The audio stimuli and somatosensory stimuli were applied to the subjects via headphones and tongue stimulus devices, as described with respect to FIGS. 1-5 above. Trial participants were all diagnosed with tinnitus. They were grouped into study arms and subjected to audio and somatosensory stimuli as follows:

ARM1 patients were provided with the stimulus protocol PS1 shown in FIG. 28A with audio input intensities adapted to each patient's audiometric threshold as determined by an audiogram and somatosensory stimulus intensities based on a calibration to the patient's threshold of perception. PS1 consisted of broadband noise mixed with frequency tones within a range of 500-8000 Hz that were presented every ~80 ms (~12.5 Hz), and each tone stimulus was synchronized in time with a burst of electrical pulses sent to a specific location on the tongue array. The pulse train consisted of 5 or 6 biphasic pulses, where each pulse had a constant amplitude, but pulse duration was adjusted during the fitting procedure to achieve comfortable sensations on the tongue (5 to 210 μs; inter-pulse period of ~3 ms; ~12-15 ms duration of burst of electrical pulses). The tones spanned the sixteen Bark Scale critical bands of hearing. The tones were presented to both ears simultaneously. Each tone was mapped to a specific location on the tongue array, and both sides of the tongue were stimulated at the same time for each tone stimulus (i.e., two electrodes in symmetric locations on the tongue array corresponding to the same tone). The background noise was almost uniform spectral density in the range from ~100 Hz to ~8000 Hz (white noise).

ARM2 patients were provided with the stimulus protocol PS2 shown in FIG. 28B with audio input intensities adapted to each patient's audiometric threshold as determined by an audiogram and somatosensory stimulus intensities based on a calibration to the patient's threshold of perception. PS2 was similar to PS1 (also at ~12.5 Hz rate), except the burst of electrical pulses was presented to the tongue with short varying delays (30-50 ms, uniform distribution) relative to the onset of the tone stimulus and the location of stimulation on the tongue array varied in a random order independent of the tone frequency. Once again, the background noise was almost uniform spectral density in the range from ~100 Hz to ~8000 Hz (white noise).

Figure 28C:
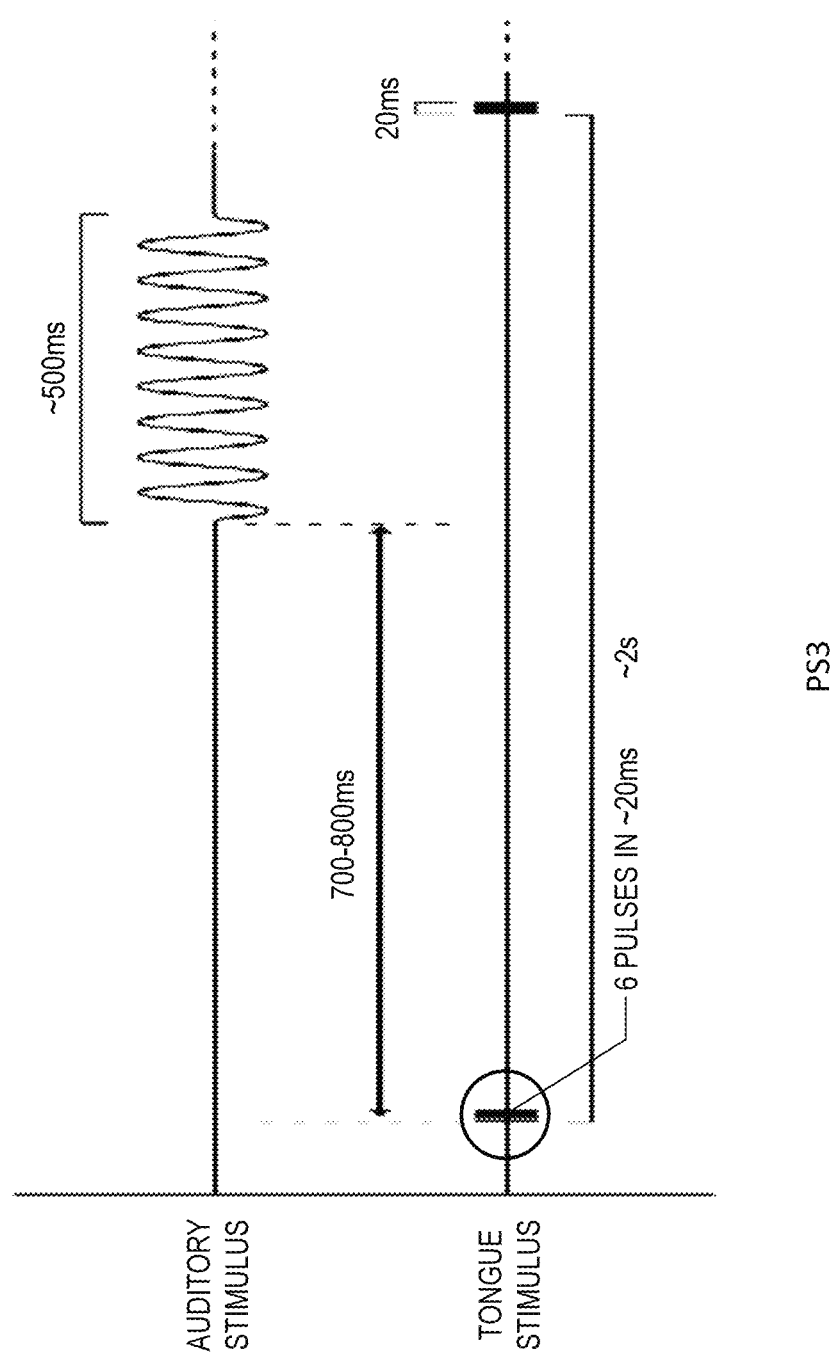

ARM3 patients were provided with the stimulus protocol PS3 shown in FIG. 28C with audio input intensities adapted to each patient's audiometric threshold as determined by an audiogram and somatosensory stimulus intensities based on a calibration to the patient's threshold of perception. PS3 consisted of a slower repetition rate (0.5 Hz), lower frequency tones (100-500 Hz) and longer delays (i.e., less synchrony; 550-950 ms, uniform distribution) between auditory and tongue stimulation compared to PS1 and PS2. PS3 also consisted of background noise that contained low frequencies (100-500 Hz). The location of stimulation on the tongue array varied in a random order independent of the tone frequency. The tongue stimulus consisted of 6 electrical pulses.

Patients in all three arms received the audio and sensory stimuli for two daily 30-minute sessions over a 12-week period.

Figures 29A, 29B:
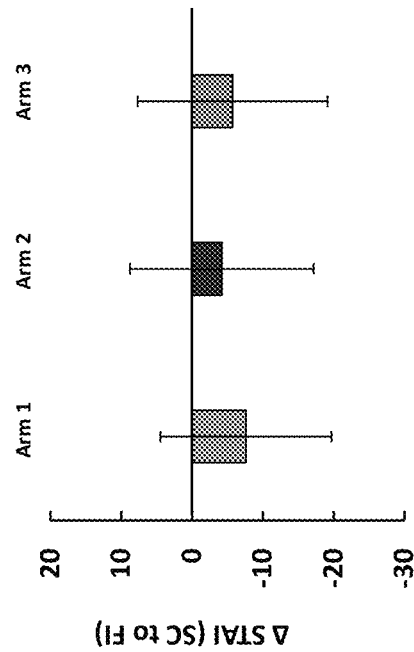
FIGS. 29A-B show changes in STAI by treatment ARM in Example 7.
Figure 30A:
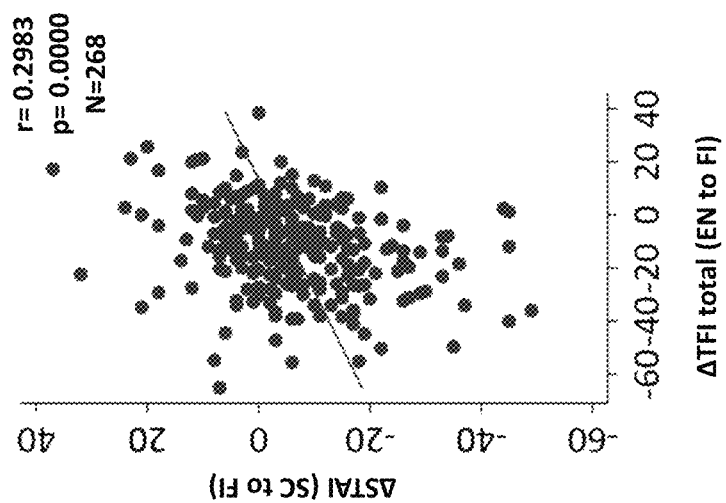
FIGS. 30A-B show the relationship of changes in STAI over the course of a 12-week therapy to changes in THI and TFI, respectively, in Example 7.
Figure 30B:
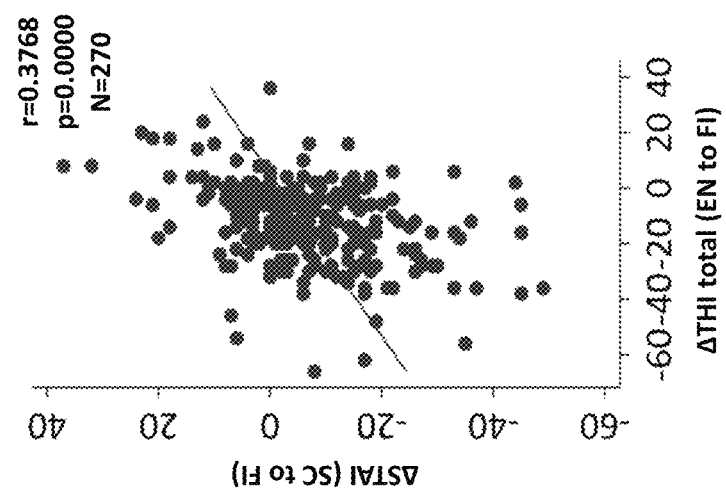

FIGS. 29A-B and FIGS. 30A-B show that the therapy reduces anxiety (as measured by the State-Trait Anxiety Inventory (STAI), a commonly used measure of trait and state anxiety) in addition to reducing tinnitus (as measured by the Tinnitus Handicap Inventory (THI) and the Tinnitus Functional Index (TFI)). FIG. 29A tabulates the mean changes in STAI for patients in ARM1, ARM2, and ARM3 as well as the baseline score for those patients. (Baseline is an average of the STAI scores for the patients at screening and at enrollment.) FIG. 29B shows the differences in STAI changes for the three treatment groups. FIGS. 30A and 30B show changes in THI and TFI, respectively, from screening to the end of the study for all three treatment groups. In order to determine whether the patients' anxiety levels were reduced to a degree greater than an anxiety reduction caused by the reduction of tinnitus alone, we examined (1) the correlation of anxiety improvements with baseline THI or TFI scores before the treatment started and (2) the correlation of anxiety improvements with the change of tinnitus loudness from before to after the treatment as measured by minimal masking level (MML).

Figure 31B:
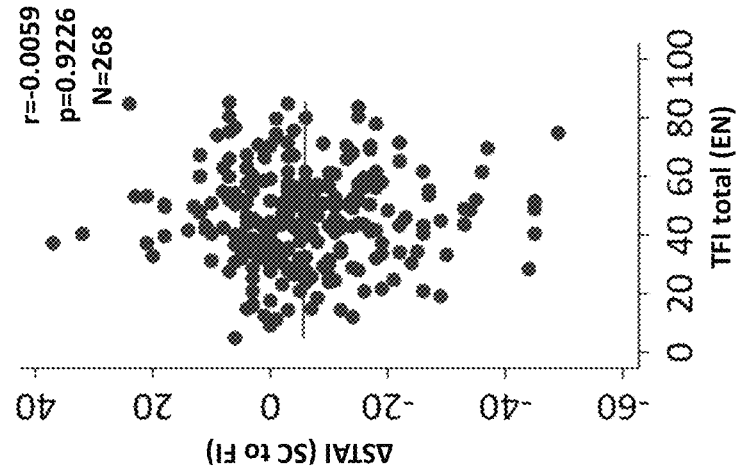
FIGS. 31A-B show changes in STAI over the course of a 12-week therapy with respect to baseline THI and TFI at enrollment, respectively, in Example 7.
Figure 31A:
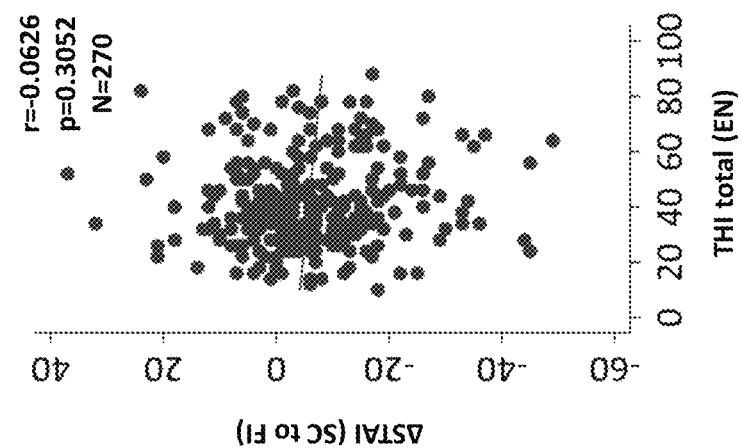
Figure 31C:
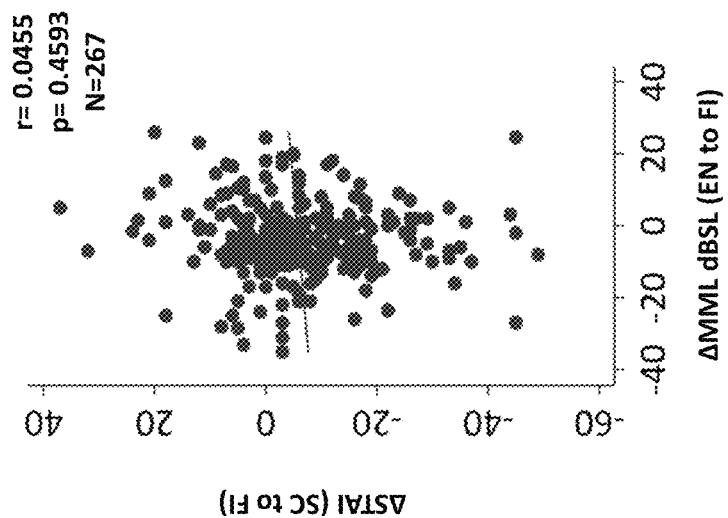
FIG. 31C shows changes in STAI over the course of a 12-week therapy with respect to changes in MML dBSL in Example 7.

FIGS. 31A-B show that anxiety reduction for the patients in all three arms is not correlated with baseline tinnitus as measured by THI and TFI. FIG. 31C shows that the reduction in tinnitus loudness over the course of the study is not correlated with the reduction in anxiety.

These data show that some bimodal audio and somatosensory stimulation protocols can reduce anxiety to a degree greater than any correlated reduction in tinnitus. This study suggests that such bimodal stimulation can reduce anxiety in a subject who does not suffer from tinnitus.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of reducing anxiety in a subject, the method comprising:
providing an audio input to the subject, the audio input comprising a sequence of tones in a frequency range comprising about 100 Hz to about 8000 Hz;
adapting intensities of the audio input to audiometric parameters of the subject;
producing a plurality of actuation signals correlated with the audio input, wherein an onset of the plurality of actuation signals has a delay in the range of −500 ms to +500 ms relative to an onset of the correlated audio input;
delivering an actuation signal of the plurality of actuation signals to each of a plurality of electrodes in contact with a tissue surface of the subject's body to provide tactile stimuli to the tissue surface; and
reducing anxiety in the subject.

2. The method of claim 1, wherein the tissue surface is a tissue surface of the subject's head.

3. The method of claim 1, wherein the tissue surface is the subject's tongue.

4. The method of claim 1, wherein the sequence of tones further comprises at least one tone that has a frequency of about 100 Hz, at least one other tone in the sequence of tones has a frequency of about 500 Hz, and other tones in the plurality of tones have frequencies in a range of about 100 Hz to about 500 Hz.

5. The method of claim 1, wherein tones within the sequence of tones are separated by an inter-tone time of about 80 milliseconds to about 2 seconds.

6. The method of claim 5, wherein each tone in the sequence of tones is presented about every 80 milliseconds.

7. The method of claim 5, wherein each tone in the sequence of tones is presented about every 2 seconds.

8. The method of claim 1, wherein each tone in the sequence of tones has a duration of about 15 milliseconds to about 500 milliseconds.

9. The method of claim 8, wherein each tone in the sequence of tones has a duration of about 15 milliseconds.

10. The method of claim 8, wherein each tone in the sequence of tones has a duration of about 500 milliseconds.

11. The method of claim 1, wherein each tone in the sequence of tones fades out as the tone ends.

12. The method of claim 1, wherein the audio input further comprises noise.

13. The method of claim 12, wherein the noise comprises broadband noise having a range of about 100 Hz to about 8000 Hz.

14. The method of claim 12, wherein the noise comprises low frequency noise having a range of about 100 Hz to about 500 Hz.

15. The method of claim 1, wherein each actuation signal comprises a pulse train.

16. The method of claim 15, where the pulse train has a duration of about 12-15 milliseconds.

17. The method of claim 15, wherein each pulse in the pulse train has a duration of about 5-210 microseconds.

18. The method of claim 1, further comprising adjusting the actuation signals to a level of sensory perception of the subject.

19. The method of claim 1, wherein the plurality of electrodes are disposed in a fixed array, and wherein the step of delivering an actuation signal comprises delivering an actuation signal to an electrode at a position in the array corresponding to a frequency of the correlated audio input.

20. The method of claim 1, wherein each electrode in the plurality of electrodes corresponds to a frequency bin within the frequency range of the audio input, the step of delivering an actuation signal further comprising delivering each actuation signal to an electrode of the plurality of electrodes having a frequency bin corresponding to a frequency of the correlated audio input simultaneous with providing the correlated audio input to the subject at such frequency.

21. The method of claim 20, wherein the step of delivering an actuation signal further comprises delivering the actuation signal simultaneously to two electrodes of the plurality of electrodes, each having a frequency bin corresponding to the frequency of the correlated audio input and simultaneous with providing the correlated audio input to the subject at the frequency.

22. The method of claim 21, wherein at least some of the plurality of electrodes are disposed in a fixed array, and wherein the two electrodes of the plurality of electrodes are symmetrically disposed in corresponding opposite sides of the fixed array.

23. The method of claim 1, wherein the step of delivering an actuation signal comprises beginning to deliver the actuation signal to each electrode after the delay relative to an onset of the correlated audio input to the subject.

24. The method of claim 23, wherein the delay is the same throughout the sequence of tones.

25. The method of claim 23, wherein the delay varies from 30 milliseconds to 950 milliseconds.

26. The method of claim 25, wherein the delay varies from 30 milliseconds to 50 milliseconds.

27. The method of claim 25, wherein the delay varies from 550 milliseconds to 950 milliseconds.

28. The method of claim 25, wherein the plurality of actuation signals have intensities based on a threshold of sensory perception of the subject.

* * * * *